(12) United States Patent
Harris et al.

(10) Patent No.: US 8,791,328 B2
(45) Date of Patent: Jul. 29, 2014

(54) POLYPEPTIDES HAVING ENDOGLUCANASE ACTIVITY AND POLYNUCLEOTIDES ENCODING SAME

(75) Inventors: Paul Harris, Carnation, WA (US); Elena Vlasenko, Davis, CA (US); Marcus Sakari Kauppinnen, Smorum (DK); Elizabeth Zaretsky, Reno, NV (US); Sarah Teter, Menlo Park, CA (US); Kimberly Brown, Elk Grove, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/562,899

(22) Filed: Jul. 31, 2012

(65) Prior Publication Data

US 2012/0309059 A1  Dec. 6, 2012

Related U.S. Application Data

(62) Division of application No. 13/253,586, filed on Oct. 5, 2011, now Pat. No. 8,258,370, which is a division of application No. 12/294,573, filed as application No. PCT/US2007/065682 on Mar. 30, 2007, now Pat. No. 8,063,267.

(60) Provisional application No. 60/788,389, filed on Mar. 30, 2006.

(51) Int. Cl.
  *C12N 15/82* (2006.01)
  *C12N 15/00* (2006.01)
  *C12N 15/10* (2006.01)

(52) U.S. Cl.
  USPC ........ 800/284; 800/278; 800/295; 435/320.1; 435/468; 435/183; 536/23.1; 536/23.7

(58) Field of Classification Search
  None
  See application file for complete search history.

(56) References Cited

U.S. PATENT DOCUMENTS

| 5,686,593 | A | 11/1997 | Woldike et al. |
| 6,190,890 | B1 * | 2/2001 | Van Den Broeck et al. .... 435/99 |
| 6,501,008 | B1 * | 12/2002 | Nevins et al. ................ 800/298 |
| 6,562,340 | B1 | 5/2003 | Bedford et al. |
| 7,005,128 | B1 | 2/2006 | Bedford et al. |
| 2005/0233423 | A1 | 10/2005 | Berka et al. |

FOREIGN PATENT DOCUMENTS

| WO | 9117244 A1 | 11/1991 |
| WO | 9714804 A1 | 4/1997 |
| WO | 0170998 A1 | 9/2001 |
| WO | 03000941 A2 | 1/2003 |
| WO | 2005074647 A2 | 8/2005 |
| WO | 2006116682 A2 | 11/2006 |
| WO | 2008151043 A1 | 12/2008 |

OTHER PUBLICATIONS

Breuil 1986, Biotechn Lett 8, 673-676.
Gilbert 1992, Bioresource Techn 39, 147-153.
Kleywegt 1997, J Mol Biol 272, 383-397.
Kumar 2000, Bioresource Technology 75, 95-97.
Kvesitadze 1995, Appl Biochem Biotechn 50, 137-144.
Rey et al, 2003, Appl Biochem Biotechnol 111(3), 153-166.

* cited by examiner

*Primary Examiner* — Brent T Page
(74) *Attorney, Agent, or Firm* — Robert L. Starnes

(57) ABSTRACT

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

31 Claims, 19 Drawing Sheets

```
GCCGTTGTCAAGATGGGCCAGAAGACGCTGCACGGATTCGCCGCCACGGCTTTGCCCGTTCTCCCCTTTGTGAAGGCTC
           M  G  Q  K  T  L  H  G  F  A  A  T  A  L  A  V  L  P  F  V  K  A
AGCAGCCCGGCAACTTCACGCCGGAGTGCACCCGCAACTGCCAACGTGGAAGTGCAGACCGCCGGCGCGCTGCTTCA
 Q  Q  P  G  N  F  T  P  E  V  H  P  Q  L  P  T  W  K  C  T  T  A  G  C  V  Q
GCAGGACACTTCGGTGGTGCTCGACTGGAACTACCGTTGGATCCACAATGCCGACGGCACCGCCTCGTGCACGACGTCC
 Q  D  T  S  V  V  L  D  W  N  Y  R  W  I  H  N  A  D  G  T  A  S  C  T  T  S
AGCGGGGTCGACCACACCCTGTGTCCAGATGAGGCGACCTGCGCGAAGAACTGCTTCGTGGAAGGCGTCAACTACACGA
 S  G  V  D  H  T  L  C  P  D  E  A  T  C  A  K  N  C  F  V  E  G  V  N  Y  T
GCAGCGGTGTCACCACATCCGGCAGTTCGCTGACGATGAGGCAGTATTTCAAGGGGAGCAACGGCCAGACCAACAGCGT
 S  S  G  V  T  T  S  G  S  S  L  T  M  R  Q  Y  F  K  G  S  N  G  Q  T  N  S  V
TTCGCCCTCGTCTCTACCTGCTCGGGCTCCGGGTCCGAGAATGGAAACTACGTAATGCTCAAGCTGCTGAGCTTCGAT
 S  P  R  L  Y  L  L  G  S  D  G  N  Y  V  M  L  K  L  L  G  Q  E  L  S  F  D
GTCGATCTCTCCACGCTCCCCTGCGGCGAGAACGGCGCCCTGTACCTGTGACGCGCCAGTGTCCCCAGGAACC
 V  D  L  S  T  L  P  C  G  E  N  G  A  L  Y  L  S  E  M  D  A  T  G  G  R  N
AGTACAACACCGGCGCCAACGGGCAGGGCTACTGCTGCAACGAGATGGACATCTCGAGGCCAACTCCCGCGCCAACGCGATGACA
 Q  Y  N  T  G  A  N  Y  G  S  G  Y  C  D  A  Q  C  P  V  Q  T  W  M  N  G  T
GCTGAACACCAACGGGCAGGGCTACTGCTGCAACGAGATGGACATCTCGAGGCCAACTCCCGCGCCAACGCGATGACA
 L  N  T  N  G  Q  G  Y  C  C  N  E  M  D  I  L  E  A  N  S  R  A  N  A  M  T
CCTCACCCCTGCGCCAACGGCAGCTGCGACAAGTCGAAGCCCTTCACCCATCATTACCGGCTTCATCACCGACGACGGCAG
 P  H  P  C  A  N  G  S  C  D  K  S  K  P  F  T  I  T  R  F  I  T  D  D  G  T  T  S
ACGGACCGGGGGCCTCACCGTTGACACGTCCAGCGGATCTATGTGCAGAATGGCAAGACCGTCGCGTCGCCGAGGCGACATC
 Y  G  P  G  L  T  V  D  T  S  K  P  F  T  I  T  R  F  I  T  D  D  G  T  T  S
CGGCACCCTCAACCAGATCCAGCGGATCTATGTGCAGAATGGCAAGACCGTCGCGTCGGCGGAGGCGACATCGG
 G  T  L  N  Q  I  Q  R  I  Y  V  Q  N  G  K  T  V  A  S  A  A  S  G  G  D  I
ATCACGGCCATCCCGGCTGCACCTCCGCCCAAGCGGTCCAACATGGGCGGCCTGGCCAACATGGGCGCGGCCCTCGGACGGGGCATGG
 I  T  A  S  G  C  T  S  A  Q  A  F  G  G  L  A  N  M  G  A  A  L  G  R  G  M
TGCTGACCTTCAGCATCTGGAACGATGCTGGGGGCTACATGAACTGGCTCGACAGCGGCAACAACGGCCCGTGCAGCAG
 V  L  T  F  S  I  W  N  D  A  G  G  Y  M  N  W  L  D  S  G  N  N  G  P  C  S  S
```

Fig. 5A

```
CACCGAGGGCAACCCGTCCAACATCCTGGCCAACTACCCGGACACCCACGTGGTCTTCTCCAACATCCGCTGGGGAGAC
 T  E  G  N  P  S  N  I  L  A  N  Y  P  D  T  H  V  V  F  S  N  I  R  W  G  D
ATCGGCTCGACGGTCCAGGTCTCCGGGAGCGGCAACGGCGGCTCGACGTCGACCACCACGCTGAGGACCT
 I  G  S  T  V  Q  V  S  G  G  N  G  G  S  T  T  T  S  T  T  T  L  R  T
CGACCACGACCACCGCCCCGACCGCCACGGCCACTGCCACGCACTGGGGACAATGCGGCGGAATGCGGGGTACGTCAACC
 T  T  T  T  A  P  T  A  T  A  T  H  W  G  Q  C  G  G  I  G
GCCTCCTGCATTCTGTTGAGGAAGTTAACTAAGTGGCCTACGCAGTGGACTGACGTCTGCGAATCGCCGTAC
                                      W  T  G  P  T  V  C  E  S  P  Y
GCATGCAAGGAGCTGAACCCCCTGGTACTACCAGTGCCTCTAAAGTATTGCAGTGAAGCCATACTCCGTGCTCGGCATGG
 A  C  K  E  L  N  P  W  Y  Y  Q  C  L  .
```

```
GATCCGGGCGGCTGTACGTGCAGGACGGCGTGGTGATCCAGAACCACGCGGTCACGGCGGGCGGCGACGTACGAC
 I  R  R  L  Y  V  Q  D  G  V  V  I  Q  N  H  A  V  T  A  G  G  A  T  Y  D
AGCATCACGGACGGCTTCTGCAACGCGACGGCCACCTGGACGCAGCGGGGCCTCGCGCGGATGGGCGAGG
 S  I  T  D  G  F  C  N  A  T  A  T  W  T  Q  R  G  L  A  R  M  G  E
CCATCGGCCGGGCATGGTGCTCATCTTCAGCCTGTGGGTTGACAACGGGGGCTTCATGAACTGGCTCGACAGCGG
 A  I  G  R  G  M  V  L  I  F  S  L  W  V  D  N  G  G  F  M  N  W  L  D  S  G
CAACGCGGGCCCTGCAACGCCGAGGGCGACCCGGCCCTGATCCTGCAGCACCCGGACGCCAGCGTCACC
 N  A  G  P  C  N  A  T  E  G  D  P  A  L  I  L  Q  H  P  D  A  S  V  T
TTCTCCAACATCCGATGGGGCGAGATCGGCAGCACCTACAAGAGCGAGTGCAGCCACTAGAGTAGAGCTTGTAATT
 F  S  N  I  R  W  G  E  I  G  S  T  Y  K  S  E  C  S  H  .
```

```
TACAGCACGGACTCGGTGAGCACCGAGTTCTGCGAGAAGACTGCTTCTTTCACCATGCAGCGCGGTGGTCTCAA
 Y  S  T  D  S  V  S  T  E  F  C  E  K  T  A  S  F  T  M  Q  R  G  G  L  K
GGCGATGGGCGAGGCTATCGGTCGTGGTATGGTGCTGGTTTTCAGCATCTGGGCGGATGATTCGGGTTTTATGA
 A  M  G  E  A  I  G  R  G  M  V  L  V  F  S  I  W  A  D  D  S  G  F  M
ACTGGTTGGATGCGGAGGGTAATGGCCCTTGCAGCGGGATCCGAAGGAGATTGTCAAGAATAAG
 N  W  L  D  A  E  G  N  G  P  C  S  A  T  E  G  D  P  K  E  I  V  K  N  K
CCGGATGCTAGGGTTACGTTCTCAAACATTAGGATTGGTGAGGTTGGTAGCACGTATGCTCCCGGTGGGAAGTG
 P  D  A  R  V  T  F  S  N  I  R  I  G  E  V  G  S  T  Y  A  P  G  G  K  C
CGGTGTTAAGAGCCAGGGTTGCTAGGGCTTACTGCTTCTTAAGGGGTGTGAAGAGAGGAGGAGGTGTTGTT
 G  V  K  S  R  V  A  R  G  L  T  A  S  .
GGGGGTTGGAGATGATAATTGGGCGAGATGGTGTAGAGCGGGTTGGTTGGATATGAATACGTTGAATTGGATGT
```

Fig. 13B

SEQUENCE LISTING

<160> NUMBER OF SEQ ID NOS: 26

<210> SEQ ID NO 1
<211> LENGTH: 1501
<212> TYPE: DNA
<213> ORGANISM: Thielavia terrestris

<400> SEQUENCE: 1

```
gccgttgtca agatgggcca gaagacgctg cacggattcg ccgccacggc tttggccgtt      60
ctcccctttg tgaaggctca gcagcccggc aacttcacgc cggaggtgca cccgcaactg     120
ccaacgtgga agtgcacgac cgccggcggc tgcgttcagc aggacacttc ggtggtgctc     180
gactggaact accgttggat ccacaatgcc gacggcaccg cctcgtgcac gacgtccagc     240
ggggtcgacc acacgctgtg tccagatgag gcgacctgcg cgaagaactg cttcgtggaa     300
ggcgtcaact acacgagcag cggtgtcacc acatccggca gttcgctgac gatgaggcag     360
tatttcaagg ggagcaacgg gcagaccaac agcgtttcgc ctcgtctcta cctgctcggc     420
tcggatggaa actacgtaat gctcaagctg ctcggccagg agctgagctt cgatgtcgat     480
ctctccacgc tcccctgcgg cgagaacggc gcgctgtacc tgtccgagat ggacgcgacc     540
ggtggcagga accagtacaa caccggcggt gccaactacg gctcgggcta ctgtgacgcc     600
cagtgtcccg tgcagacgtg gatgaacggc acgctgaaca ccaacgggca gggctactgc     660
tgcaacgaga tggacatcct cgaggccaac tcccgcgcca acgcgatgac acctcacccc     720
tgcgccaacg gcagctgcga caagagcggg tgcggactca acccctacgc cgagggctac     780
aagagctact acggaccggg cctcacggtt gacacgtcga agcccttcac catcattacc     840
cgcttcatca ccgacgacgg cacgaccagc ggcaccctca accagatcca gcggatctat     900
gtgcagaatg gcaagacggt cgcgtcggct gcgtccggag gcgacatcat cacggcatcc     960
ggctgcacct cggcccaggc gttcggcggg ctggccaaca tgggcgcggc gcttggacgg    1020
ggcatggtgc tgaccttcag catctggaac gacgctgggg gctacatgaa ctggctcgac    1080
agcggcaaca acggcccgtg cagcagcacc gagggcaacc cgtccaacat cctggccaac    1140
tacccggaca cccacgtggt cttctccaac atccgctggg gagacatcgg ctcgacggtc    1200
caggtctcgg gaggcggcaa cggcggctcg accaccacca cgtcgaccac cacgctgagg    1260
acctcgacca cgaccaccac caccgccccg acggccactg ccacgcactg gggacaatgc    1320
ggcggaatcg gggtacgtca accgcctcct gcattctgtt gaggaagtta actaacgtgg    1380
cctacgcagt ggactggacc gaccgtctgc gaatcgccgt acgcatgcaa ggagctgaac    1440
ccctggtact accagtgcct ctaaagtatt gcagtgaagc catactccgt gctcggcatg    1500
g                                                                    1501
```

```
<210> SEQ ID NO 2
<211> LENGTH: 464
<212> TYPE: PRT
<213> ORGANISM: Thielavia terrestris

<400> SEQUENCE: 2

Met Gly Gln Lys Thr Leu His Gly Phe Ala Thr Ala Leu Ala Val
 1               5                  10                  15

Leu Pro Phe Val Lys Ala Gln Gln Pro Gly Asn Phe Thr Pro Glu Val
             20                  25                  30

His Pro Gln Leu Pro Thr Trp Lys Cys Thr Thr Ala Gly Gly Cys Val
             35                  40                  45

Gln Gln Asp Thr Ser Val Val Leu Asp Trp Asn Tyr Arg Trp Ile His
 50                  55                  60

Asn Ala Asp Gly Thr Ala Ser Cys Thr Thr Ser Ser Gly Val Asp His
65                   70                  75                  80

Thr Leu Cys Pro Asp Glu Ala Thr Cys Ala Lys Asn Cys Phe Val Glu
                 85                  90                  95

Gly Val Asn Tyr Thr Ser Ser Gly Val Thr Thr Ser Gly Ser Ser Leu
            100                 105                 110

Thr Met Arg Gln Tyr Phe Lys Gly Ser Asn Gly Gln Thr Asn Ser Val
            115                 120                 125

Ser Pro Arg Leu Tyr Leu Leu Gly Ser Asp Gly Asn Tyr Val Met Leu
        130                 135                 140

Lys Leu Leu Gly Gln Glu Leu Ser Phe Asp Val Asp Leu Ser Thr Leu
145                 150                 155                 160

Pro Cys Gly Glu Asn Gly Ala Leu Tyr Leu Ser Glu Met Asp Ala Thr
                165                 170                 175

Gly Gly Arg Asn Gln Tyr Asn Thr Gly Gly Ala Asn Tyr Gly Ser Gly
            180                 185                 190

Tyr Cys Asp Ala Gln Cys Pro Val Gln Thr Trp Met Asn Gly Thr Leu
        195                 200                 205

Asn Thr Asn Gly Gln Gly Tyr Cys Cys Asn Glu Met Asp Ile Leu Glu
    210                 215                 220

Ala Asn Ser Arg Ala Asn Ala Met Thr Pro His Pro Cys Ala Asn Gly
225                 230                 235                 240

Ser Cys Asp Lys Ser Gly Cys Gly Leu Asn Pro Tyr Ala Glu Gly Tyr
                245                 250                 255

Lys Ser Tyr Tyr Gly Pro Gly Leu Thr Val Asp Thr Ser Lys Pro Phe
            260                 265                 270

Thr Ile Ile Thr Arg Phe Ile Thr Asp Asp Gly Thr Thr Ser Gly Thr
        275                 280                 285

Leu Asn Gln Ile Gln Arg Ile Tyr Val Gln Asn Gly Lys Thr Val Ala
    290                 295                 300

Ser Ala Ala Ser Gly Gly Asp Ile Ile Thr Ala Ser Gly Cys Thr Ser
305                 310                 315                 320

Ala Gln Ala Phe Gly Gly Leu Ala Asn Met Gly Ala Ala Leu Gly Arg
                325                 330                 335

Gly Met Val Leu Thr Phe Ser Ile Trp Asn Asp Ala Gly Gly Tyr Met
            340                 345                 350

Asn Trp Leu Asp Ser Gly Asn Gly Pro Cys Ser Ser Thr Glu Gly
        355                 360                 365

Asn Pro Ser Asn Ile Leu Ala Asn Tyr Pro Asp Thr His Val Val Phe
    370                 375                 380
```

```
Ser Asn Ile Arg Trp Gly Asp Ile Gly Ser Thr Val Gln Val Ser Gly
385                 390                 395                 400

Gly Gly Asn Gly Gly Ser Thr Thr Thr Ser Thr Thr Thr Leu Arg
            405                 410                 415

Thr Ser Thr Thr Thr Thr Thr Thr Ala Pro Thr Ala Thr Ala Thr His
            420                 425                 430

Trp Gly Gln Cys Gly Gly Ile Gly Trp Thr Gly Pro Thr Val Cys Glu
            435                 440                 445

Ser Pro Tyr Ala Cys Lys Glu Leu Asn Pro Trp Tyr Tyr Gln Cys Leu
            450                 455                 460

<210> SEQ ID NO 3
<211> LENGTH: 1368
<212> TYPE: DNA
<213> ORGANISM: Thielavia terrestris

<400> SEQUENCE: 3
accgatccgc tcgaagatgg cgcccaagtc tacagttctg gccgcctggc tgctctcctc     60
gctggccgcg gcccagcaga tcggcaaagc cgtgcccgag gtccacccca aactgacaac    120
gcagaagtgc actctccgcg gcgggtgcaa gcctgtccgc acctcggtcg tgctcgactc    180
gtccgcgcgc tcgctgcaca aggtcgggga ccccaacacc agctgcagcg tcggcggcga    240
cctgtgctcg gacgcgaagt cgtgcggcaa gaactgcgcg ctcgagggcg tcgactacgc    300
ggcccacggc gtggcgacca agggcgacgc cctcacgctg caccagtggc tcaagggggc    360
cgacggcacc tacaggaccg tctcgccgcg cgtatacctc ctgggcgagg acgggaagaa    420
ctacgaggac ttcaagctgc tcaacgccga gctcagcttc gacgtcgacg tgtcccagct    480
cgtctgcggc atgaacggcg ccctgtactt ctccgagatg gagatggacg gcggccgcag    540
cccgctgaac ccggcgggcg ccacgtacgg cacgggctac tgcgacgcgc agtgccccaa    600
gttggacttt atcaacggcg aggtatttct tctctcttct gttttctttt tccatcgctt    660
tttctgaccg gaatccgccc tcttagctca acaccaacca cacgtacggg gcgtgctgca    720
acgagatgga catctgggag ccaacgcgc tggcgcaggc gctcacgccg cacccgtgca    780
acgcgacgcg ggtgtacaag tgcgacacgg cggacgagtg cgggcagccg gtgggcgtgt    840
gcgacgaatg ggggtgctcg tacaacccgt ccaacttcgg ggtcaaggac tactacgggc    900
gcaacctgac ggtggacacg aaccgcaagt tcacggtgac gacgcagttc gtgacgtcca    960 acggcgggc ggacggcgag ctgaccgaga tccggcggct gtacgtgcag gacggcgtgg   1020
tgatccagaa ccacgcggtc acggcggggcg gggcgacgta cgacagcatc acggacggct   1080
tctgcaacgc gacggccacc tggacgcagc agcggggcgg gctcgcgcgc atgggcgagg   1140
ccatcggccg cggcatggtg ctcatcttca gcctgtgggt tgacaacggc ggcttcatga   1200
actggctcga cagcggcaac gccgggccct gcaacgccac cgagggcgac ccggccctga   1260
tcctgcagca gcaccggac gccagcgtca ccttctccaa catccgatgg ggcgagatcg   1320
gcagcacgta caagagcgag tgcagccact agagtagagc ttgtaatt                1368

<210> SEQ ID NO 4
<211> LENGTH: 423
<212> TYPE: PRT
<213> ORGANISM: Thielavia terrestris

<400> SEQUENCE: 4

Met Ala Pro Lys Ser Thr Val Leu Ala Ala Trp Leu Leu Ser Ser Leu
1               5                   10                  15
```

Ala Ala Ala Gln Gln Ile Gly Lys Ala Val Pro Glu Val His Pro Lys
            20                  25                  30

Leu Thr Thr Gln Lys Cys Thr Leu Arg Gly Gly Cys Lys Pro Val Arg
        35                  40                  45

Thr Ser Val Val Leu Asp Ser Ala Arg Ser Leu His Lys Val Gly
    50                  55                  60

Asp Pro Asn Thr Ser Cys Ser Val Gly Gly Asp Leu Cys Ser Asp Ala
65                  70                  75                  80

Lys Ser Cys Gly Lys Asn Cys Ala Leu Glu Gly Val Asp Tyr Ala Ala
                85                  90                  95

His Gly Val Ala Thr Lys Gly Asp Ala Leu Thr Leu His Gln Trp Leu
                100                 105                 110

Lys Gly Ala Asp Gly Thr Tyr Arg Thr Val Ser Pro Arg Val Tyr Leu
            115                 120                 125

Leu Gly Glu Asp Gly Lys Asn Tyr Glu Asp Phe Lys Leu Leu Asn Ala
    130                 135                 140

Glu Leu Ser Phe Asp Val Asp Val Ser Gln Leu Val Cys Gly Met Asn
145                 150                 155                 160

Gly Ala Leu Tyr Phe Ser Glu Met Glu Met Asp Gly Gly Arg Ser Pro
                165                 170                 175

Leu Asn Pro Ala Gly Ala Thr Tyr Gly Thr Gly Tyr Cys Asp Ala Gln
                180                 185                 190

Cys Pro Lys Leu Asp Phe Ile Asn Gly Glu Leu Asn Thr Asn His Thr
            195                 200                 205

Tyr Gly Ala Cys Cys Asn Glu Met Asp Ile Trp Glu Ala Asn Ala Leu
    210                 215                 220

Ala Gln Ala Leu Thr Pro His Pro Cys Asn Ala Thr Arg Val Tyr Lys
225                 230                 235                 240

Cys Asp Thr Ala Asp Glu Cys Gly Gln Pro Val Gly Val Cys Asp Glu
                245                 250                 255

Trp Gly Cys Ser Tyr Asn Pro Ser Asn Phe Gly Val Lys Asp Tyr Tyr
                260                 265                 270

Gly Arg Asn Leu Thr Val Asp Thr Asn Arg Lys Phe Thr Val Thr Thr
            275                 280                 285

Gln Phe Val Thr Ser Asn Gly Arg Ala Asp Gly Glu Leu Thr Glu Ile
    290                 295                 300

Arg Arg Leu Tyr Val Gln Asp Gly Val Val Ile Gln Asn His Ala Val
305                 310                 315                 320

Thr Ala Gly Gly Ala Thr Tyr Asp Ser Ile Thr Asp Gly Phe Cys Asn
                325                 330                 335

Ala Thr Ala Thr Trp Thr Gln Gln Arg Gly Gly Leu Ala Arg Met Gly
            340                 345                 350

Glu Ala Ile Gly Arg Gly Met Val Leu Ile Phe Ser Leu Trp Val Asp
    355                 360                 365

Asn Gly Gly Phe Met Asn Trp Leu Asp Ser Gly Asn Ala Gly Pro Cys
    370                 375                 380

Asn Ala Thr Glu Gly Asp Pro Ala Leu Ile Leu Gln Gln His Pro Asp
385                 390                 395                 400

Ala Ser Val Thr Phe Ser Asn Ile Arg Trp Gly Glu Ile Gly Ser Thr
                405                 410                 415

Tyr Lys Ser Glu Cys Ser His
            420

<210> SEQ ID NO 5
<211> LENGTH: 1480
<212> TYPE: DNA
<213> ORGANISM: Cladorrhinum foecundissimum

<400> SEQUENCE: 5

```
gatccgaatt cctcctctcg ttctttagtc acagaccaga catctgccca cgatggttca      60
caagttcgcc ctcctcaccg gcctcgccgc ctccctcgca tctgcccagc agatcggcac     120
cgtcgtcccc gagtctcacc ccaagcttcc caccaagcgc tgcactctcg ccggtggctg     180
ccagaccgtc gacacctcca tcgtcatcga cgccttccag cgtcccctcc acaagatcgg     240
cgacccttcc actccttgcg tcgtcggcgg ccctctctgc cccgacgcca gtcctgcgc     300
tgagaactgc gcgctcgagg gtgtcgacta tgcctcctgg ggcatcaaga ccgagggcga     360
cgccctaact ctcaaccagt ggatgcccga cccggcgaac cctggccagt acaagacgac     420
tactccccgt acttaccttg ttgctgagga cggcaagaac tacgaggatg tgaagctcct     480
ggctaaggag atctcgtttg atgccgatgt cagcaacctt ccctgcggca tgaacggtgc     540
tttctacttg tctgagatgt tgatggatgg tggacgtggc gacctcaacc ctgctggtgc     600
cgagtatggt accggttact gtgatgcgca gtgcttcaag ttggatttca tcaacggcga     660
ggccaacatc gaccaaaagc acggcgcctg ctgcaacgaa atggacattt tcgaatccaa     720
ctcgcgcgcc aagaccttcg tcccccaccc ctgcaacatc acgcaggtct acaagtgcga     780
aggcgaagac gagtgcggcc agcccgtcgg cgtgtgcgac aagtggggt gcggcttcaa     840
cgagtacaaa tggggcgtcg agtccttcta cggccggggc tcgcagttcg ccatcgactc     900
ctccaagaag ttcaccgtca ccacgcagtt cctgaccgac aacggcaagg aggacggcgt     960
cctcgtcgag atccgccgct gtggcacca ggatggcaag ctgatcaaga acaccgctat    1020
ccaggttgag gagaactaca gcacggactc ggtgagcacc gagttctgcg agaagactgc    1080
ttctttcacc atgcagcgcg gtggtctcaa ggcgatgggc gaggctatcg gtcgtggtat    1140
ggtgctggtt ttcagcatct gggcggatga ttcgggtttt atgaactggt tggatgcgga    1200
gggtaatggc ccttgcagcg cgactgaggg cgatccgaag gagattgtca agaataagcc    1260
ggatgctagg gttacgttct caaacattag gattggtgag gttggtagca cgtatgctcc    1320
gggtgggaag tgcggtgtta agagcagggt tgctagggg cttactgctt cttaaggggg    1380
gtgtgaagag aggaggaggt gttgttgggg gttggagatg ataattgggc gagatggtgt    1440
agagcgggtt ggttggatat gaatacgttg aattggatgt                         1480
```

<210> SEQ ID NO 6
<211> LENGTH: 440
<212> TYPE: PRT
<213> ORGANISM: Cladorrhinum foecundissimum

<400> SEQUENCE: 6

```
Met Val His Lys Phe Ala Leu Leu Thr Gly Leu Ala Ala Ser Leu Ala
1               5                   10                  15

Ser Ala Gln Gln Ile Gly Thr Val Val Pro Glu Ser His Pro Lys Leu
            20                  25                  30

Pro Thr Lys Arg Cys Thr Leu Ala Gly Gly Cys Gln Thr Val Asp Thr
        35                  40                  45

Ser Ile Val Ile Asp Ala Phe Gln Arg Pro Leu His Lys Ile Gly Asp
    50                  55                  60

Pro Ser Thr Pro Cys Val Val Gly Gly Pro Leu Cys Pro Asp Ala Lys
```

```
            65                  70                  75                  80
Ser Cys Ala Glu Asn Cys Ala Leu Glu Gly Val Asp Tyr Ala Ser Trp
                    85                  90                  95

Gly Ile Lys Thr Glu Gly Asp Ala Leu Thr Leu Asn Gln Trp Met Pro
            100                 105                 110

Asp Pro Ala Asn Pro Gly Gln Tyr Lys Thr Thr Pro Arg Thr Tyr
            115                 120                 125

Leu Val Ala Glu Asp Gly Lys Asn Tyr Glu Asp Val Lys Leu Leu Ala
        130                 135                 140

Lys Glu Ile Ser Phe Asp Ala Asp Val Ser Asn Leu Pro Cys Gly Met
145                 150                 155                 160

Asn Gly Ala Phe Tyr Leu Ser Glu Met Leu Met Asp Gly Arg Gly
                165                 170                 175

Asp Leu Asn Pro Ala Gly Ala Glu Tyr Gly Thr Gly Tyr Cys Asp Ala
                180                 185                 190

Gln Cys Phe Lys Leu Asp Phe Ile Asn Gly Glu Ala Asn Ile Asp Gln
            195                 200                 205

Lys His Gly Ala Cys Cys Asn Glu Met Asp Ile Phe Glu Ser Asn Ser
        210                 215                 220

Arg Ala Lys Thr Phe Val Pro His Pro Cys Asn Ile Thr Gln Val Tyr
225                 230                 235                 240

Lys Cys Glu Gly Glu Asp Glu Cys Gly Gln Pro Val Gly Val Cys Asp
                245                 250                 255

Lys Trp Gly Cys Gly Phe Asn Glu Tyr Lys Trp Gly Val Glu Ser Phe
            260                 265                 270

Tyr Gly Arg Gly Ser Gln Phe Ala Ile Asp Ser Ser Lys Lys Phe Thr
        275                 280                 285

Val Thr Thr Gln Phe Leu Thr Asp Asn Gly Lys Glu Asp Gly Val Leu
            290                 295                 300

Val Glu Ile Arg Arg Leu Trp His Gln Asp Gly Lys Leu Ile Lys Asn
305                 310                 315                 320

Thr Ala Ile Gln Val Glu Glu Asn Tyr Ser Thr Asp Ser Val Ser Thr
                325                 330                 335

Glu Phe Cys Glu Lys Thr Ala Ser Phe Thr Met Gln Arg Gly Gly Leu
            340                 345                 350

Lys Ala Met Gly Glu Ala Ile Gly Arg Gly Met Val Leu Val Phe Ser
        355                 360                 365

Ile Trp Ala Asp Asp Ser Gly Phe Met Asn Trp Leu Asp Ala Glu Gly
370                 375                 380

Asn Gly Pro Cys Ser Ala Thr Glu Gly Asp Pro Lys Glu Ile Val Lys
385                 390                 395                 400

Asn Lys Pro Asp Ala Arg Val Thr Phe Ser Asn Ile Arg Ile Gly Glu
                405                 410                 415

Val Gly Ser Thr Tyr Ala Pro Gly Gly Lys Cys Gly Val Lys Ser Arg
                420                 425                 430

Val Ala Arg Gly Leu Thr Ala Ser
            435                 440

<210> SEQ ID NO 7
<211> LENGTH: 26
<212> TYPE: DNA
<213> ORGANISM: Thielavia terrestris
<220> FEATURE:
<221> NAME/KEY: misc_feature
<222> LOCATION: (15)..(15)
```

```
<223> OTHER INFORMATION: N=A,C,G,OR T
<220> FEATURE:
<221> NAME/KEY: misc_feature
<222> LOCATION: (18)..(18)
<223> OTHER INFORMATION: N=A,C,G, OR T
<220> FEATURE:
<221> NAME/KEY: misc_feature
<222> LOCATION: (21)..(21)
<223> OTHER INFORMATION: R=A OR G
<220> FEATURE:
<221> NAME/KEY: misc_feature
<222> LOCATION: (24)..(24)
<223> OTHER INFORMATION: R=A OR G

<400> SEQUENCE: 7
agggtgccgc tggtngtncc rtcrtc                                    26

<210> SEQ ID NO 8
<211> LENGTH: 33
<212> TYPE: DNA
<213> ORGANISM: Thielavia terrestris
<220> FEATURE:
<221> NAME/KEY: misc_feature
<222> LOCATION: (25)..(25)
<223> OTHER INFORMATION: N= A,C,G, OR T
<220> FEATURE:
<221> NAME/KEY: misc_feature
<222> LOCATION: (28)..(28)
<223> OTHER INFORMATION: Y=T OR C
<220> FEATURE:
<221> NAME/KEY: misc_feature
<222> LOCATION: (31)..(31)
<223> OTHER INFORMATION: Y=T OR C

<400> SEQUENCE: 8
agctggtgct aaatatggta ctggntaytg yga                            33

<210> SEQ ID NO 9
<211> LENGTH: 25
<212> TYPE: DNA
<213> ORGANISM: Thielavia terrestris
<220> FEATURE:
<221> NAME/KEY: misc_feature
<222> LOCATION: (18)..(18)
<223> OTHER INFORMATION: R=A OR G
<220> FEATURE:
<221> NAME/KEY: misc_feature
<222> LOCATION: (21)..(21)
<223> OTHER INFORMATION: Y=T OR C
<220> FEATURE:
<221> NAME/KEY: misc_feature
<222> LOCATION: (23)..(23)
<223> OTHER INFORMATION: N=A,C,G, OR T

<400> SEQUENCE: 9
ggctactgcg acgcccartg ycnaa                                     25

<210> SEQ ID NO 10
<211> LENGTH: 28
<212> TYPE: DNA
<213> ORGANISM: Thielavia terrestris
<220> FEATURE:
<221> NAME/KEY: misc_feature
<222> LOCATION: (11)..(11)
<223> OTHER INFORMATION: R=A OR G
<220> FEATURE:
<221> NAME/KEY: misc_feature
<222> LOCATION: (17)..(17)
<223> OTHER INFORMATION: Y=T OR C
<220> FEATURE:
<221> NAME/KEY: misc_feature
<222> LOCATION: (23)..(23)
<223> OTHER INFORMATION: R=A OR G
```

```
<220> FEATURE:
<221> NAME/KEY: misc_feature
<222> LOCATION: (26)..(26)
<223> OTHER INFORMATION: R=A OR G

<400> SEQUENCE: 10
cctcccagat rtccatytcg ttrcarca                                         28

<210> SEQ ID NO 11
<211> LENGTH: 25
<212> TYPE: DNA
<213> ORGANISM: Thielavia terrestris

<400> SEQUENCE: 11
cttggtaccg agctcggatc cacta                                            25

<210> SEQ ID NO 12
<211> LENGTH: 25
<212> TYPE: DNA
<213> ORGANISM: Thielavia terrestris

<400> SEQUENCE: 12
atagggcgaa ttgggccctc tagat                                            25

<210> SEQ ID NO 13
<211> LENGTH: 22
<212> TYPE: DNA
<213> ORGANISM: Aspergillus nidulans

<400> SEQUENCE: 13
gtgccccatg atacgcctcc gg                                               22

<210> SEQ ID NO 14
<211> LENGTH: 26
<212> TYPE: DNA
<213> ORGANISM: Aspergillus nidulans

<400> SEQUENCE: 14
gagtcgtatt tccaaggctc ctgacc                                           26

<210> SEQ ID NO 15
<211> LENGTH: 24
<212> TYPE: DNA
<213> ORGANISM: Aspergillus nidulans

<400> SEQUENCE: 15
ggaggccatg aagtggacca acgg                                             24

<210> SEQ ID NO 16
<211> LENGTH: 45
<212> TYPE: DNA
<213> ORGANISM: Aspergillus niger

<400> SEQUENCE: 16
caccgtgaaa gccatgctct tccttcgtg tagaagacca gacag                       45

<210> SEQ ID NO 17
<211> LENGTH: 45
<212> TYPE: DNA
<213> ORGANISM: Aspergillus niger

<400> SEQUENCE: 17
ctggtcttct acacgaagga aagagcatgg ctttcacggt gtctg                      45
```

```
<210> SEQ ID NO 18
<211> LENGTH: 44
<212> TYPE: DNA
<213> ORGANISM: Aspergillus niger

<400> SEQUENCE: 18
ctatatacac aactggattt accatgggcc cgcggccgca gatc            44

<210> SEQ ID NO 19
<211> LENGTH: 44
<212> TYPE: DNA
<213> ORGANISM: Aspergillus niger

<400> SEQUENCE: 19
gatctgcggc cgcgggccca tggtaaatcc agttgtgtat atag            44

<210> SEQ ID NO 20
<211> LENGTH: 29
<212> TYPE: DNA
<213> ORGANISM: Aspergillus oryzae

<400> SEQUENCE: 20
actggattac catgggccag aagacgctg                             29

<210> SEQ ID NO 21
<211> LENGTH: 31
<212> TYPE: DNA
<213> ORGANISM: Aspergillus oryzae

<400> SEQUENCE: 21
agtcacctct agttagaggc actggtagta c                          31

<210> SEQ ID NO 22
<211> LENGTH: 36
<212> TYPE: DNA
<213> ORGANISM: Thielavia terrestris

<400> SEQUENCE: 22
actggattac catggcgccc aagtctacag ttctgg                     36

<210> SEQ ID NO 23
<211> LENGTH: 38
<212> TYPE: DNA
<213> ORGANISM: Thielavia terrestris

<400> SEQUENCE: 23
tcacctctag ttaattaact agtggctgca ctcgctct                   38

<210> SEQ ID NO 24
<211> LENGTH: 12
<212> TYPE: DNA
<213> ORGANISM: Cladorrhinum foecundissimum

<400> SEQUENCE: 24
ctttccagca ca                                               12

<210> SEQ ID NO 25
<211> LENGTH: 21
<212> TYPE: DNA
<213> ORGANISM: Cladorrhinum foecundissimum

<400> SEQUENCE: 25
ccacacttct cttccttcct c                                     21
```

```
<210> SEQ ID NO 26
<211> LENGTH: 21
<212> TYPE: DNA
<213> ORGANISM: Cladorrhinum foecundissimum

<400> SEQUENCE: 26
ccccatcctt taactatagc g                                             21
```

POLYPEPTIDES HAVING ENDOGLUCANASE ACTIVITY AND POLYNUCLEOTIDES ENCODING SAME

CROSS-REFERENCE TO RELATED APPLICATIONS

This application is a divisional of U.S. patent application Ser. No., 13/253,586 filed Oct. 5, 2011, now U.S. Pat. No. 8,258,370, which is a divisional of U.S. patent application Ser. No. 12/294,573 filed Mar. 9, 2009, now U.S. Pat. No. 8,063,267, which is a 35 U.S.C. 371 national application of PCT/US07/65682 filed on Mar. 30, 2007, which claims priority from U.S. provisional application Ser. No. 60/788,389 filed on Mar. 30, 2006. The contents of these applications are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to deposits of biological material which have been made at the Northern Regional Research Center (NRRL) under the Budapest Treaty and assigned accession numbers NRRL B-30896, NRRL B-30897, and NRRL B-30899, which microbial deposits are incorporated herein by reference.

BACKGROUND OF THE INVENTION

1. Field of the Invention

The present invention relates to isolated polypeptides having endoglucanase activity and isolated polynucleotides encoding the polypeptides. The invention also relates to nucleic acid constructs, vectors, and host cells comprising the polynucleotides as well as methods for producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiohydrolase I is a 1,4-beta-D-glucan cellobiohydrolase (E.C. 3.2.1.91) activity that catalyzes the hydrolysis of 1,4-beta-D-glucosidic linkages in cellulose, cellotetriose, or any beta-1,4-linked glucose containing polymer, releasing cellobiose from the reducing ends of the chain. Cellobiohydrolase II is a 1,4-beta-D-glucan cellobiohydrolase (E.C. 3.2.1.91) activity that catalyzes the hydrolysis of 1,4-beta-D-glucosidic linkages in cellulose, cellotetriose, or any beta-1,4-linked glucose containing polymer, releasing cellobiose from the non-reducing ends of the chain. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

Kvesitadaze et al., 1995, *Applied Biochemistry and Biotechnology* 50: 137-143, describe the isolation and properties of a thermostable endoglucanase from a thermophilic mutant strain of *Thielavia terrestris*. Gilbert et al., 1992, *Bioresource Technology* 39: 147-154, describe the characterization of the enzymes present in the cellulose system of *Thielavia terrestris* 255B. Breuil et al., 1986, *Biotechnology Letters* 8: 673-676, describe production and localization of cellulases and beta-glucosidases from *Thielavia terrestris* strains C464 and NRRL 8126. Kumar et al., 2000, *Bioresource Technology* 75: 95-97, disclose the production of endo-1,4-beta-glucanase by a *Cladorrhinum foecundissimum*.

It would be an advantage in the art to identify new endoglucanases having improved properties, such as improved hydrolysis rate, better thermal stability, reduced adsorption to lignin, and ability to hydrolyze non-cellulosic components of biomass, such as hemicellulose, in addition to hydrolyzing cellulose. Endoglucanases with a broad range of side activities on hemicellulose can be especially beneficial for improving the overall hydrolysis yield of complex, hemicellulose-rich biomass substrates.

It is an object of the present invention to provide improved polypeptides having endoglucanase activity and polynucleotides encoding the polypeptides.

SUMMARY OF THE INVENTION

The present invention relates to isolated polypeptides having endoglucanase activity selected from the group consisting of:

(a) a polypeptide comprising an amino acid sequence having at least 80% identity with the mature polypeptide of SEQ ID NO: 2, at least 70% identity with the mature polypeptide of SEQ ID NO: 4, or at least 85% identity with the mature polypeptide of SEQ ID NO: 6;

(b) a polypeptide which is encoded by a polynucleotide which hybridizes under at least high stringency conditions with (i) the mature polypeptide coding sequence of SEQ ID NO: 1 or SEQ ID NO: 5, (ii) the cDNA sequence contained in the mature polypeptide coding sequence of SEQ ID NO: 1 or SEQ ID NO: 5, or (iii) a complementary strand of (i) or (ii), or under at least medium-high stringency conditions with (i) the mature polypeptide coding sequence of SEQ ID NO: 3, (ii) the genomic DNA sequence comprising the mature polypeptide coding sequence of SEQ ID NO: 3, or (iii) a complementary strand of (i) or (ii);

(c) a polypeptide which is encoded by a polynucleotide comprising a nucleotide sequence having at least 80% identity with the mature polypeptide coding sequence of SEQ ID NO: 1, at least 70% identity with the mature polypeptide coding sequence of SEQ ID NO: 3, or at least 85% identity with the mature polypeptide coding sequence of SEQ ID NO: 5; and (d) a variant comprising a substitution, deletion, and/or insertion of one or more amino acids of the mature polypeptide of SEQ ID NO: 2, SEQ ID NO: 4, or SEQ ID NO: 6.

The present invention also relates to isolated polynucleotides encoding polypeptides having endoglucanase activity, selected from the group consisting of:

(a) a polynucleotide encoding a polypeptide comprising an amino acid sequence having at least 80% identity with the mature polypeptide of SEQ ID NO: 2, at least 70% identity with the mature polypeptide of SEQ ID NO: 4, or at least 85% identity with the mature polypeptide of SEQ ID NO: 6;

(b) a polynucleotide which hybridizes under at least high stringency conditions with (i) the mature polypeptide coding sequence of SEQ ID NO: 1 or SEQ ID NO: 5, (ii) the cDNA sequence contained in the mature polypeptide coding sequence of SEQ ID NO: 1 or SEQ ID NO: 5, or (iii) a complementary strand of (i) or (ii), or under at least medium-high stringency conditions with (i) the mature polypeptide coding sequence of SEQ ID NO: 3, (ii) the genomic DNA sequence comprising the mature polypeptide coding sequence of SEQ ID NO: 3, or (iii) a complementary strand of (i) or (ii);

(c) a polynucleotide comprising a nucleotide sequence having at least 80% identity with the mature polypeptide coding sequence of SEQ ID NO: 1, at least 70% identity with the mature polypeptide coding sequence of SEQ ID NO: 3, or at least 85% identity with the mature polypeptide coding sequence of SEQ ID NO: 5; and (d) a polynucleotide encoding a variant comprising a substitution, deletion, and/or insertion of one or more amino acids of the mature polypeptide of SEQ ID NO: 2, SEQ ID NO: 4, or SEQ ID NO: 6.

In a preferred aspect, the mature polypeptide is amino acids 23 to 464 of SEQ ID NO: 2. In another preferred aspect, the mature polypeptide is amino acids 20 to 423 of SEQ ID NO: 4. In another preferred aspect, the mature polypeptide is amino acids 19 to 440 of SEQ ID NO: 6. In another preferred aspect, the mature polypeptide coding sequence is nucleotides 79 to 1461 of SEQ ID NO: 1. In another preferred aspect, the mature polypeptide coding sequence is nucleotides 74 to 1349 of SEQ ID NO: 3. In another preferred aspect, the mature polypeptide coding sequence is nucleotides 107 to 1372 of SEQ ID NO: 5.

The present invention also relates to nucleic acid constructs, recombinant expression vectors, recombinant host cells comprising the polynucleotides, and methods of producing a polypeptide having endoglucanase activity.

The present invention also relates to methods of inhibiting the expression of a polypeptide in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is an siRNA or an miRNA molecule.

The present invention also relates to methods of using the polypeptides having endoglucanase activity in the conversion of cellulose to glucose and various substances.

The present invention also relates to plants comprising an isolated polynucleotide encoding such a polypeptide having endoglucanase activity.

The present invention also relates to methods for producing such a polypeptide having endoglucanase activity, comprising: (a) cultivating a transgenic plant or a plant cell comprising a polynucleotide encoding such a polypeptide having endoglucanase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 22 of SEQ ID NO: 2, amino acids 1 to 19 SEQ ID NO: 4, or amino acids 1 to 18 of SEQ ID NO: 6, wherein the gene is foreign to the nucleotide sequence, wherein the gene is foreign to the nucleotide sequence.

BRIEF DESCRIPTION OF THE FIGURES

FIGS. 5A and 5B show the genomic DNA sequence and the deduced amino acid sequence of a *Thielavia terrestris* NRRL 8126 CEL7C endoglucanase (SEQ ID NOs: 1 and 2, respectively).
FIGS. 6A and 6B show the genomic sequence and the deduced amino acid sequence of a *Thielavia terrestris* NRRL 8126 CEL7E endoglucanase (SEQ ID NOs: 3 and 4, respectively).
FIGS. 13A and 13B show the cDNA sequence and the deduced amino acid sequence of a *Cladorrhinum foecundissimum* ATCC 62373 CEL7A endoglucanase (SEQ ID NOs: 5 and 6, respectively).

DEFINITIONS

Figure 1:
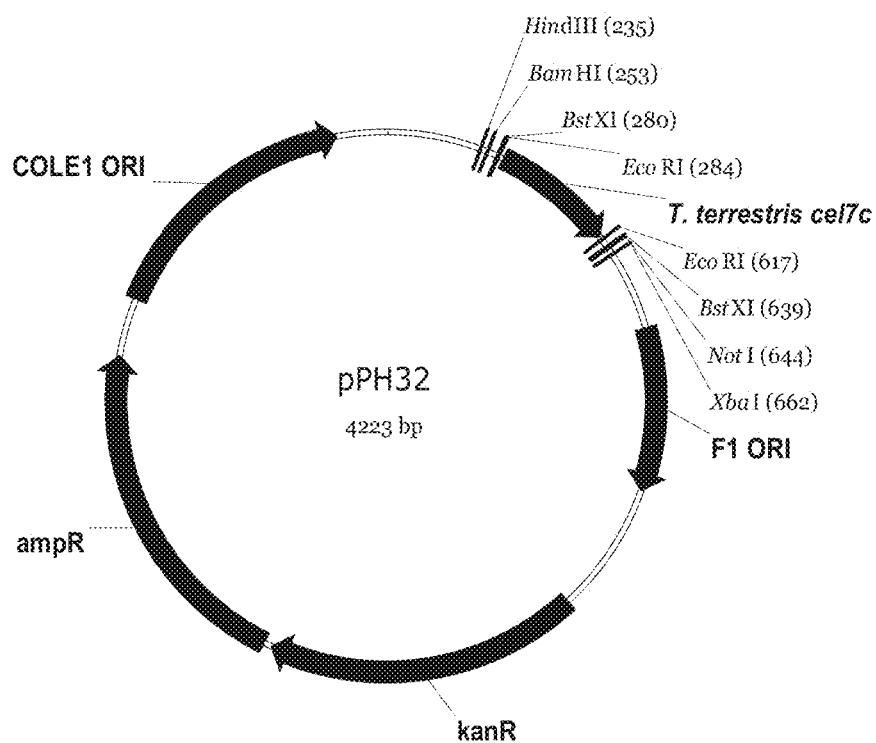
FIG. 1 shows a restriction map of pPH32.

Endoglucanase activity: The term "endoglucanase activity" is defined herein as an endo-1,4-beta-D-glucan 4-glucanohydrolase (E.C. No. 3.2.1.4) that catalyses the endohydrolysis of 1,4-beta-D-glycosidic linkages in cellulose, cellulose derivatives (such as carboxymethyl cellulose and hydroxyethyl cellulose), lignocellulose, lignocellulose derivatives, lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, *Pure and Appl. Chem.* 59: 257-268. One unit of endoglucanase activity is defined as 1.0 µmole of reducing sugars produced per minute at 50° C., pH 5.0.

In a preferred aspect, the polypeptides of the present invention having endoglucanase activity further have enzyme activity toward one or more substrates selected from the group consisting of xylan, xyloglucan, arabinoxylan, 1,4-beta-D-mannan, and galactomannan. The activity of the polypeptides having endoglucanase activity on these polysaccharide substrates is determined as percent of the substrate hydrolyzed to reducing sugars after incubating the substrate (5 mg per ml) with a polypeptide having endoglucanase activity of the present invention (5 mg protein per g of substrate) for 24 hours with intermittent stirring at pH 5.0 (50 mM sodium acetate) and 50° C. Reducing sugars in hydrolysis mixtures are determined by the p-hydroxybenzoic acid hydrazide (PHBAH) assay.

In a more preferred aspect, the polypeptides of the present invention having endoglucanase activity further have enzyme activity toward xylan. In another more preferred aspect, the polypeptides of the present invention having endoglucanase activity further have enzyme activity toward xyloglucan. In another more preferred aspect, the polypeptides of the present invention having endoglucanase activity further have enzyme activity toward arabinoxylan. In another more preferred aspect, the polypeptides of the present invention having endoglucanase activity further have enzyme activity toward 1,4-beta-D-mannan. In another more preferred aspect, the polypeptides of the present invention having endoglucanase activity further have enzyme activity toward galactomannan. In another more preferred aspect, the polypeptides of the present invention having endoglucanase activity further have enzyme activity toward xylan, xyloglucan, arabinoxylan, 1,4-beta-D-mannan, and/or galactomannan.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the endoglucanase activity of mature polypeptide of SEQ ID NO: 2, SEQ ID NO: 4, or SEQ ID NO: 6.

Family 7 Glycoside Hydrolase or Family GH7: The term "Family 7 glycoside hydrolase" or "Family GH7" is defined herein as a polypeptide falling into the glycoside hydrolase Family 7 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively or recombinantly associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having endoglucanase activity that is in its final form following translation and any post-translational modifications, such as N-terminal processing, C-terminal truncation, glycosylation, etc.

Mature polypeptide coding sequence: The term "mature polypeptide coding sequence" is defined herein as a nucleotide sequence that encodes a mature polypeptide having endoglucanase activity.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The output of Needle labeled "longest identity" is used as the percent identity and is calculated as follows:

(Identical Residues×100)/(Length of Alignment−
Number of Gaps in Alignment)

For purposes of the present invention, the degree of identity between two nucleotide sequences is determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EDNAFULL matrix. The output of Needle labeled "longest identity" is used as the percent identity and is calculated as follows:

(Identical Residues×100)/(Length of Alignment−
Number of Gaps in Alignment)

Homologous sequence: The term "homologous sequence" is defined herein as a predicted protein which gives an E value (or expectancy score) of less than 0.001 in a fasta search (Pearson, W. R., 1999, in *Bioinformatics Methods and Protocols*, S. Misener and S. A. Krawetz, ed., pp. 185-219) with the *Thielavia terrestris* CEL7C or CEL7E endoglucanase (SEQ ID NO: 2 or SEQ ID NO: 4, respectively) or the *Cladorrhinum foecundissimum* CEL7A endoglucanase (SEQ ID NO: 6) as query sequence.

Polypeptide fragment: The term "polypeptide fragment" is defined herein as a polypeptide having one or more amino acids deleted from the amino and/or carboxyl terminus of the mature polypeptide of SEQ ID NO: 2, SEQ ID NO: 4, or SEQ ID NO: 6; or a homologous sequence thereof; wherein the fragment has endoglucanase activity. In a preferred aspect, a fragment contains at least 380 amino acid residues, more preferably at least 400 amino acid residues, and most preferably at least 420 amino acid residues of the mature polypeptide of SEQ ID NO: 2 or a homologous sequence thereof. In another preferred aspect, a fragment contains at least 340 amino acid residues, more preferably at least 360 amino acid residues, and most preferably at least 380 amino acid residues of the mature polypeptide of SEQ ID NO: 4 or a homologous sequence thereof. In another preferred aspect, a fragment contains at least 360 amino acid residues, more preferably at least 380 amino acid residues, and most preferably at least 400 amino acid residues of the mature polypeptide of SEQ ID NO: 6 or a homologous sequence thereof.

Subsequence: The term "subsequence" is defined herein as a nucleotide sequence having one or more nucleotides deleted from the 5' and/or 3' end of the mature polypeptide coding sequence of SEQ ID NO: 1, SEQ ID NO: 3, or SEQ ID NO: 5; or a homologous sequence thereof; wherein the subsequence encodes a polypeptide fragment having endoglucanase activity. In a preferred aspect, a subsequence contains at least 1140 nucleotides, more preferably at least 1200 nucleotides, and most preferably at least 1260 nucleotides of the mature polypeptide coding sequence of SEQ ID NO: 1 or a homologous sequence thereof. In another preferred aspect, a subsequence contains at least 1020 nucleotides, more preferably at least 1080 nucleotides, and most preferably at least 1140 nucleotides of the mature polypeptide coding sequence of SEQ ID NO: 3 or a homologous sequence thereof. In another preferred aspect, a subsequence contains at least 1080 nucleotides, more preferably at least 1140 nucleotides, and most preferably at least 1200 nucleotides of the mature polypeptide coding sequence of SEQ ID NO: 5 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively or recombinantly associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, or recombinant nucleotide sequence.

Mature polypeptide coding sequence: The term "mature polypeptide coding sequence" is defined herein as a nucleotide sequence that encodes a mature polypeptide having endoglucanase activity.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2, SEQ ID NO: 4, or SEQ ID NO: 6; or a homologous sequence thereof; as well as genetic manipulation of the DNA encoding such a polypeptide. The modification can be substitutions, deletions and/or insertions of one or more amino acids as well as replacements of one or more amino acid side chains.

Artificial variant: When used herein, the term "artificial variant" means a polypeptide having endoglucanase activity produced by an organism expressing a modified nucleotide sequence of the mature polypeptide coding sequence of SEQ ID NO: 1, SEQ ID NO: 3, or SEQ ID NO: 5; or a homologous sequence thereof. The modified nucleotide sequence is obtained through human intervention by modification of the nucleotide sequence disclosed in SEQ ID NO: 1, SEQ ID NO: 3, or SEQ ID NO: 5; or a homologous sequence thereof.

DETAILED DESCRIPTION OF THE INVENTION

Polypeptides Having Endoglucanase Activity

In a first aspect, the present invention relates to isolated polypeptides comprising an amino acid sequence having a degree of identity to the mature polypeptide of SEQ ID NO: 2, SEQ ID NO: 4, or SEQ ID NO: 6 of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, or 99%, which have endoglucanase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from the mature polypeptide of SEQ ID NO: 2, SEQ ID NO: 4, or SEQ ID NO: 6.

A polypeptide of the present invention preferably comprises the amino acid sequence of SEQ ID NO: 2 or an allelic variant thereof; or a fragment thereof that has endoglucanase activity. In a preferred aspect, a polypeptide comprises the amino acid sequence of SEQ ID NO: 2. In another preferred aspect, a polypeptide comprises the mature polypeptide of SEQ ID NO: 2. In another preferred aspect, a polypeptide comprises amino acids 23 to 464 of SEQ ID NO: 2, or an allelic variant thereof; or a fragment thereof that has endoglucanase activity. In another preferred aspect, a polypeptide comprises amino acids 23 to 464 of SEQ ID NO: 2. In another preferred aspect, a polypeptide consists of the amino acid sequence of SEQ ID NO: 2 or an allelic variant thereof; or a fragment thereof that has endoglucanase activity. In another preferred aspect, a polypeptide consists of the amino acid sequence of SEQ ID NO: 2. In another preferred aspect, a polypeptide consists of the mature polypeptide of SEQ ID NO: 2. In another preferred aspect, a polypeptide consists of amino acids 23 to 464 of SEQ ID NO: 2 or an allelic variant thereof; or a fragment thereof that has endoglucanase activity. In another preferred aspect, a polypeptide consists of amino acids 23 to 464 of SEQ ID NO: 2.

A polypeptide of the present invention preferably also comprises the amino acid sequence of SEQ ID NO: 4 or an allelic variant thereof; or a fragment thereof that has endoglucanase activity. In a preferred aspect, a polypeptide comprises the amino acid sequence of SEQ ID NO: 4. In another preferred aspect, a polypeptide comprises the mature polypeptide of SEQ ID NO: 4. In another preferred aspect, a polypeptide comprises amino acids 20 to 423 of SEQ ID NO: 4, or an allelic variant thereof; or a fragment thereof that has endoglucanase activity. In another preferred aspect, a polypeptide comprises amino acids 20 to 423 of SEQ ID NO: 4. In another preferred aspect, a polypeptide consists of the amino acid sequence of SEQ ID NO: 4 or an allelic variant thereof; or a fragment thereof that has endoglucanase activity. In another preferred aspect, a polypeptide consists of the amino acid sequence of SEQ ID NO: 4. In another preferred aspect, a polypeptide consists of the mature polypeptide of SEQ ID NO: 4. In another preferred aspect, a polypeptide consists of amino acids 20 to 423 of SEQ ID NO: 4 or an allelic variant thereof; or a fragment thereof that has endoglucanase activity. In another preferred aspect, a polypeptide consists of amino acids 20 to 423 of SEQ ID NO: 4.

A polypeptide of the present invention preferably also comprises the amino acid sequence of SEQ ID NO: 6 or an allelic variant thereof; or a fragment thereof that has endoglucanase activity. In a preferred aspect, a polypeptide comprises the amino acid sequence of SEQ ID NO: 6. In another preferred aspect, a polypeptide comprises the mature polypeptide of SEQ ID NO: 6. In another preferred aspect, a polypeptide comprises amino acids 19 to 440 of SEQ ID NO: 6, or an allelic variant thereof; or a fragment thereof that has endoglucanase activity. In another preferred aspect, a polypeptide comprises amino acids 19 to 440 of SEQ ID NO: 6. In another preferred aspect, a polypeptide consists of the amino acid sequence of SEQ ID NO: 6 or an allelic variant thereof; or a fragment thereof that has endoglucanase activity. In another preferred aspect, a polypeptide consists of the amino acid sequence of SEQ ID NO: 6. In another preferred aspect, a polypeptide consists of the mature polypeptide of SEQ ID NO: 6. In another preferred aspect, a polypeptide consists of amino acids 19 to 440 of SEQ ID NO: 6 or an allelic variant thereof; or a fragment thereof that has endoglucanase activity. In another preferred aspect, a polypeptide consists of amino acids 19 to 440 of SEQ ID NO: 6.

In a second aspect, the present invention relates to isolated polypeptides having endoglucanase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 5 or the genomic DNA sequence comprising the mature polypeptide coding sequence of SEQ ID NO: 1, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual,* 2d edition, Cold Spring Harbor, N.Y.). A subsequence of the mature polypeptide coding sequence of SEQ ID NO: 1, SEQ ID NO: 3, or SEQ ID NO: 5 contains at least 100 contiguous nucleotides or preferably at least 200 contiguous nucleotides. Moreover, the subsequence may encode a polypeptide fragment which has endoglucanase activity. In a preferred aspect, the mature polypeptide coding sequence is nucleotides 79 to 1461 of SEQ ID NO: 1. In another preferred aspect, the mature polypeptide coding sequence is nucleotides 74 to 1349 of SEQ ID NO: 3. In another preferred aspect, the mature polypeptide coding sequence is nucleotides 107 to 1372 of SEQ ID NO: 5. In another preferred aspect, the complementary strand is the full-length complementary strand of the mature polypeptide coding sequence of SEQ ID NO: 1, SEQ ID NO: 3, or SEQ ID NO: 5.

The nucleotide sequence of SEQ ID NO: 1, SEQ ID NO: 3, or SEQ ID NO: 5; or a subsequence thereof; as well as the amino acid sequence of SEQ ID NO: 2, SEQ ID NO: 4, or SEQ ID NO: 6; or a fragment thereof; may be used to design a nucleic acid probe to identify and clone DNA encoding polypeptides having endoglucanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA which hybridizes with the probes described above and which encodes a polypeptide having endoglucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, SEQ ID NO: 3, or SEQ ID NO: 5; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, or SEQ ID NO: 5; the cDNA sequence contained in the mature polypeptide coding sequence of SEQ ID NO: 1 or SEQ ID NO: 5 or the genomic DNA sequence comprising the mature polypeptide coding sequence of SEQ ID NO: 3; its complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 79 to 1461 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pPH50 which is contained in E. coli NRRL B-30899, wherein the polynucleotide sequence thereof encodes a polypeptide having endoglucanase activity. In another preferred aspect, the nucleic acid probe is the mature polypeptide coding region contained in plasmid pPH50 which is contained in E. coli NRRL B-30899.

In another preferred aspect, the nucleic acid probe is the mature polypeptide coding sequence of SEQ ID NO: 3. In another preferred aspect, the nucleic acid probe is nucleotides 74 to 1349 of SEQ ID NO: 3. In another preferred aspect, the nucleic acid probe is a polynucleotide sequence which encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pPH38 which is contained in E. coli NRRL B-30896, wherein the polynucleotide sequence thereof encodes a polypeptide having endoglucanase activity. In another preferred aspect, the nucleic acid probe is the mature polypeptide coding region contained in plasmid pPH38 which is contained in E. coli NRRL B-30896.

In another preferred aspect, the nucleic acid probe is the mature polypeptide coding sequence of SEQ ID NO: 5. In another preferred aspect, the nucleic acid probe is nucleotides 107 to 1372 of SEQ ID NO: 5. In another preferred aspect, the nucleic acid probe is a polynucleotide sequence which encodes the polypeptide of SEQ ID NO: 6, or a subsequence thereof. In another preferred aspect, the nucleic acid probe is SEQ ID NO: 5. In another preferred aspect, the nucleic acid probe is the polynucleotide sequence contained in plasmid pPH46 which is contained in E. coli NRRL B-30897, wherein the polynucleotide sequence thereof encodes a polypeptide having endoglucanase activity. In another preferred aspect, the nucleic acid probe is the mature polypeptide coding region contained in plasmid pPH46 which is contained in E. coli NRRL B-30897.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides encoded by polynucleotides comprising or consisting of nucleotide sequences which have a degree of identity to the mature polypeptide coding sequence of SEQ ID NO: 1, SEQ ID NO: 3, or SEQ ID NO: 5 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide.

In a preferred aspect, the mature polypeptide coding sequence is nucleotides 79 to 1461 of SEQ ID NO: 1. In another preferred aspect, the mature polypeptide coding sequence is nucleotides 74 to 1349 of SEQ ID NO: 3. In another preferred aspect, the mature polypeptide coding sequence is nucleotides 107 to 1372 of SEQ ID NO: 5. See polynucleotide section herein.

In a fourth aspect, the present invention relates to artificial variants comprising a substitution, deletion, and/or insertion of one or more (or several) amino acids of the mature polypeptide of SEQ ID NO: 2, SEQ ID NO: 4, or SEQ ID NO: 6; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., endoglucanase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, SEQ ID NO: 4, or SEQ ID NO: 6, such as amino acids 23 to 464 of SEQ ID NO: 2, amino acids 20 to 423 of SEQ ID NO: 4, or amino acids 19 to 440 of SEQ ID NO: 6, is 10, preferably 9, more preferably 8, more preferably 7, more preferably at most 6, more preferably 5, more preferably 4, even more preferably 3, most preferably 2, and even most preferably 1.

Sources of Polypeptides Having Endoglucanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having endoglucanase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having endoglucanase activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having endoglucanase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having endoglucanase activity.

In another preferred aspect, the polypeptide is a *Streptococcus equisimilis, Streptococcus pyogenes, Streptococcus* uberis, or *Streptococcus equi* subsp. *Zooepidemicus* polypeptide having endoglucanase activity.

In another preferred aspect, the polypeptide is a *Streptomyces achromogenes, Streptomyces avermitilis, Streptomyces coelicolor, Streptomyces griseus*, or *Streptomyces lividans* polypeptide having endoglucanase activity.

A polypeptide having endoglucanase activity of the present invention may also be a fungal polypeptide, and more preferably a yeast polypeptide such as a *Candida, Kluyveromyces, Pichia, Saccharomyces, Schizosaccharomyces*, or *Yarrowia* polypeptide having endoglucanase activity; or more preferably a filamentous fungal polypeptide such as an *Acremonium, Aspergillus, Aureobasidium, Chrysosporium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide having endoglucanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having endoglucanase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium brasilianum, Penicillium camembertii, Penicillium capsulatum, Penicillium chrysogenum, Penicillium citreonigrum, Penicillium citrinum, Penicilliumclaviforme, Penicillium corylophilum, Penicillium crustosum, Penicillium digitatum, Penicillium expansum, Penicillium funiculosum, Penicillium glabrum, Penicillium granulatum, Penicillium griseofulvum, Penicillium islandicum, Penicillium italicum, Penicillium janthinellum, Penicillium lividum, Penicillium megasporum, Penicillium melinfi, Penicillium notatum, Penicillium oxalicum, Penicillium puberulum, Penicillium purpurescens, Penicillium purpurogenum, Penicillium roquefortii, Penicillium rugulosum, Penicillium spinulosum, Penicillium waksmanfi, Trichoderma harzianum, Trichoderma koningii, Trichoderma longibrachiatum, Trichoderma reesei*, or *Trichoderma viride* polypeptide having endoglucanase activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Thielavia terricola, Thielavia thermophila, Thielavia variospora*, or *Thielavia wareingii* polypeptide having endoglucanase activity.

In a more preferred aspect, the polypeptide is a *Thielavia terrestris* polypeptide, and most preferably a *Thielavia terrestris* NRRL 8126 polypeptide, e.g., the polypeptide of SEQ ID NO: 2 or SEQ ID NO: 4, or the mature polypeptide thereof.

In another more preferred aspect, the polypeptide is a *Cladorrhinum foecundissimum* polypeptide, and most preferably a *Cladorrhinum foecundissimum* ATCC 62373 polypeptide, e.g., the polypeptide of SEQ ID NO: 6 or the mature polypeptide thereof.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having endoglucanase activity from the fusion protein.

Examples of cleavage sites include, but are not limited to, a Kex2 site which encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to an isolated polynucleotide comprising or consisting of a nucleotide sequence which encodes a polypeptide of the present invention having endoglucanase activity.

In a preferred aspect, the nucleotide sequence comprises or consists of SEQ ID NO: 1. In another more preferred aspect, the nucleotide sequence comprises or consists of the sequence contained in plasmid pPH50 which is contained in E. coli NRRL B-30899. In another preferred aspect, the nucleotide sequence comprises or consists of the mature polypeptide coding region of SEQ ID NO: 1. In another preferred aspect, the nucleotide sequence comprises or consists of nucleotides 79 to 1461 of SEQ ID NO: 1. In another more preferred aspect, the nucleotide sequence comprises or consists of the mature polypeptide coding region contained in plasmid pPH50 which is contained in E. coli NRRL B-30899. The present invention also encompasses nucleotide sequences which encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 which encode fragments of SEQ ID NO: 2 that have endoglucanase activity.

In another preferred aspect, the nucleotide sequence comprises or consists of SEQ ID NO: 3. In another more preferred aspect, the nucleotide sequence comprises or consists of the sequence contained in plasmid pPH38 which is contained in E. coli NRRL B-30896. In another preferred aspect, the nucleotide sequence comprises or consists of the mature polypeptide coding region of SEQ ID NO: 3. In another preferred aspect, the nucleotide sequence comprises or consists of nucleotides 74 to 1349 of SEQ ID NO: 3. In another more preferred aspect, the nucleotide sequence comprises or consists of the mature polypeptide coding region contained in plasmid pPH38 which is contained in E. coli NRRL B-30896. The present invention also encompasses nucleotide sequences which encode polypeptides comprising or consisting of the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 which encode fragments of SEQ ID NO: 4 that have endoglucanase activity.

In another preferred aspect, the nucleotide sequence comprises or consists of SEQ ID NO: 5. In another more preferred aspect, the nucleotide sequence comprises or consists of the sequence contained in plasmid pPH46 which is contained in E. coli NRRL B-30897. In another preferred aspect, the nucleotide sequence comprises or consists of the mature polypeptide coding region of SEQ ID NO: 5. In another preferred aspect, the nucleotide sequence comprises or consists of nucleotides 107 to 1372 of SEQ ID NO: 5. In another more preferred aspect, the nucleotide sequence comprises or consists of the mature polypeptide coding region contained in plasmid pPH46 which is contained in E. coli NRRL B-30897. The present invention also encompasses nucleotide sequences which encode polypeptides comprising or consisting of the amino acid sequence of SEQ ID NO: 6 or the mature polypeptide thereof, which differ from SEQ ID NO: 5 or the mature polypeptide coding sequence thereof by virtue of the degeneracy of the genetic code. The present invention also relates to subsequences of SEQ ID NO: 5 which encode fragments of SEQ ID NO: 6 that have endoglucanase activity.

The present invention also relates to mutant polynucleotides comprising or consisting of at least one mutation in the mature polypeptide coding sequence of SEQ ID NO: 1, SEQ ID NO: 3, or SEQ ID NO: 5, in which the mutant nucleotide sequence encodes the mature polypeptide of SEQ ID NO: 2, SEQ ID NO: 4, or SEQ ID NO: 6. In a preferred aspect, the mature polypeptide is amino acids 23 to 464 of SEQ ID NO: 2. In another preferred aspect, the mature polypeptide is amino acids 20 to 423 of SEQ ID NO: 4. In another preferred aspect, the mature polypeptide is amino acids 19 to 440 of SEQ ID NO: 6.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of Myceliophthora thermophila CBS 117.65, basidiomycete CBS 494.95, or basidiomycete CBS 495.95, or another or related organism and thus, for example, may be an allelic or species variant of the polypeptide encoding region of the nucleotide sequence.

The present invention also relates to isolated polynucleotides comprising or consisting of nucleotide sequences which have a degree of identity to the mature polypeptide coding sequence of SEQ ID NO: 1, SEQ ID NO: 3, or SEQ ID NO: 5 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 79 to 1461 of SEQ ID NO: 1. In another preferred aspect, the mature polypeptide coding sequence is nucleotides 74 to 1349 of SEQ ID NO: 3. In another preferred aspect, the mature polypeptide coding sequence is nucleotides 107 to 1372 of SEQ ID NO: 5.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, SEQ ID NO: 3, or SEQ ID NO: 5, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, Protein Expression and Purification 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for endoglucanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding a polypeptide of the present invention, which hybridize under very low conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 5 or the genomic DNA sequence comprising the mature polypeptide coding sequence of SEQ ID NO: 3, or (iii) a complementary strand of (i) or (ii); or allelic variants and subsequences thereof (Sambrook et al., 1989, supra), as defined herein. In a preferred aspect, the mature polypeptide coding sequence is nucleotides 79 to 1461 of SEQ ID NO: 1. In another preferred aspect, the mature polypeptide coding sequence is nucleotides 74 to 1349 of SEQ ID NO: 3. In another preferred aspect, the mature polypeptide coding sequence is nucleotides 107 to 1372 of SEQ ID NO: 5. In another preferred aspect, the complementary strand is the full-length complementary strand of the mature polypeptide coding sequence of SEQ ID NO: 1, SEQ ID NO: 3, or SEQ ID NO: 5.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, SEQ ID NO: 3, or SEQ ID NO: 5, (ii) the cDNA sequence contained in the mature polypeptide coding sequence of SEQ ID NO: 1 or SEQ ID NO: 5 or the genomic DNA sequence comprising the mature polypeptide coding sequence of SEQ ID NO: 3, or (iii) a complementary strand of (i) or (ii); and (b) isolating the hybridizing polynucleotide, which encodes a polypeptide having endoglucanase activity. In a preferred aspect, the mature polypeptide coding sequence is nucleotides 79 to 1461 of SEQ ID NO: 1. In another preferred aspect, the mature polypeptide coding sequence is nucleotides 74 to 1349 of SEQ ID NO: 3. In another preferred aspect, the mature polypeptide coding sequence is nucleotides 107 to 1372 of SEQ ID NO: 5. In another preferred aspect, the complementary strand is the full-length complementary strand of the mature polypeptide coding sequence of SEQ ID NO: 1, SEQ ID NO: 3, or SEQ ID NO: 5.

Nucleic Acid Constructs

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI),

*Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

In a preferred aspect, the signal peptide is amino acids 1 to 22 of SEQ ID NO: 2. In another preferred aspect, the signal peptide coding region is nucleotides 13 to 79 of SEQ ID NO: 1.

In another preferred aspect, the signal peptide is amino acids 1 to 19 of SEQ ID NO: 4. In another preferred aspect, the signal peptide coding region is nucleotides 17 to 73 of SEQ ID NO: 3.

In another preferred aspect, the signal peptide is amino acids 1 to 18 of SEQ ID NO: 6. In another preferred aspect, the signal peptide coding region is nucleotides 53 to 106 of SEQ ID NO: 5.

The control sequence may also be a propeptide coding region that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but are not limited to, *Bacillus, Streptococcus, Strepto-* myces, *Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus*.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans*.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98:6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57).

The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crook-*

*wellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium brasilianum, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Thielavia*. In another preferred aspect, the cell is of the genus *Cladorrhinum*. In a more preferred aspect, the cell is *Thielavia terrestris*. In another more preferred aspect, the cell is *Cladorrhinum foecundissimum*. In a most preferred aspect, the cell is *Thielavia terrestris* NRRL 8126. In another most preferred aspect, the cell is *Cladorrhinum foecundissimum* ATCC 62373.

The present invention also relates to methods for producing a polypeptide of the present invention, comprising: (a) cultivating a host cell under conditions conducive for production of the polypeptide; and (b) recovering the polypeptide.

The present invention also relates to methods for producing a polypeptide of the present invention, comprising: (a) cultivating a host cell under conditions conducive for production of the polypeptide, wherein the host cell comprises a mutant nucleotide sequence having at least one mutation in the mature polypeptide coding sequence of SEQ ID NO: 1, SEQ ID NO: 3, or SEQ ID NO: 5, wherein the mutant nucleotide sequence encodes a polypeptide which comprises or consists of the mature polypeptide of SEQ ID NO: 2, SEQ ID NO: 4, or SEQ ID NO: 6, and (b) recovering the polypeptide.

In a preferred aspect, the mature polypeptide is amino acids 23 to 464 of SEQ ID NO: 2. In another preferred aspect, the mature polypeptide is amino acids 20 to 423 of SEQ ID NO: 4. In another preferred aspect, the mature polypeptide is amino acids 19 to 440 of SEQ ID NO: 6. In another preferred aspect, the mature polypeptide coding sequence is nucleotides 79 to 1461 of SEQ ID NO: 1. In another preferred aspect, the mature polypeptide coding sequence is nucleotides 74 to 1349 of SEQ ID NO: 3. In another preferred aspect, the mature polypeptide coding sequence is nucleotides 107 to 1372 of SEQ ID NO: 5.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having endoglucanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding the polypeptide having endoglucanase activity of the present invention under conditions conducive for production of the polypeptide; and (b) recovering the polypeptide.

Removal or Reduction of Endoglucanase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising: (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of endoglucanase activity by fermentation of a cell which produces both a polypeptide of the present invention as well as the protein product of interest by adding an effective amount of an agent capable of inhibiting endoglucanase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of endoglucanase activity by cultivating the cell under conditions permitting the expression of the product, subjecting the resultant culture broth to a combined pH and temperature treatment so as to reduce the endoglucanase activity substantially, and recovering the product from the culture broth. Alternatively, the combined pH and temperature treatment may be performed on an enzyme preparation recovered from the culture broth. The combined pH and temperature treatment may optionally be used in combination with a treatment with an endoglucanase inhibitor.

In accordance with this aspect of the invention, it is possible to remove at least 60%, preferably at least 75%, more preferably at least 85%, still more preferably at least 95%, and most preferably at least 99% of the endoglucanase activity. Complete removal of endoglucanase activity may be obtained by use of this method.

The combined pH and temperature treatment is preferably carried out at a pH in the range of 2-3 or 10-11 and a temperature in the range of at least 75-85° C. for a sufficient period of time to attain the desired effect, where typically, 1 to 3 hours is sufficient.

The methods used for cultivation and purification of the product of interest may be performed by methods known in the art.

The methods of the present invention for producing an essentially endoglucanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The endoglucanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from endoglucanase activity which is produced by a method of the present invention.

Methods of Inhibiting Expression of a Polypeptide

The present invention also relates to methods of inhibiting expression of a polypeptide in a cell, comprising administering to the cell or expressing in the cell a double-stranded RNA (dsRNA) molecule, wherein the dsRNA comprises a subsequence or portion of a polynucleotide of the present invention. In a preferred aspect, the dsRNA is about 15, 16, 17, 18, 19, 20, 21, 22, 23, 24, 25 or more duplex nucleotides in length. In another preferred aspect, the polypeptide has endoglucanase activity.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules for inhibiting expression of a polypeptide in a cell, wherein the dsRNA comprises a subsequence or portion of a polynucleotide encoding the mature polypeptide of SEQ ID NO: 2, SEQ ID NO: 4, or SEQ ID NO: 6. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention also relates to methods for degrading or converting a cellulosic material, comprising: treating the cellulosic material with a composition comprising an effective amount of a polypeptide having endoglucanase activity of the present invention. In a preferred aspect, the method further comprises recovering the degraded or converted cellulosic material.

The polypeptides and host cells of the present invention may be used in the production of monosaccharides, disaccharides, and polysaccharides as chemical or fermentation feedstocks from cellulosic biomass for the production of ethanol, plastics, other products or intermediates. The composition comprising the polypeptide having endoglucanase activity may be in the form of a crude fermentation broth with or without the cells removed or in the form of a semi-purified or purified enzyme preparation. Alternatively, the composition may comprise a host cell of the present invention as a source of the polypeptide having endoglucanase activity in a fermentation process with the biomass. The host cell may also contain native or heterologous genes that encode other proteins and enzymes, mentioned above, useful in the processing of biomass. In particular, the polypeptides and host cells of the present invention may be used to increase the value of processing residues (dried distillers grain, spent grains from brewing, sugarcane bagasse, etc.) by partial or complete degradation of cellulose or hemicellulose. The compositions can also comprise other proteins and enzymes useful in the processing of biomass, e.g., cellobiohydrolase, beta-glucosidase, hemicellulolytic enzymes, enhancers (WO 2005/074647, WO 2005/074656), etc.

In the methods of the present invention, any cellulosic material, such as biomass, can be used. It is understood herein that the term "cellulosic material" encompasses lignocellulose. Biomass can include, but is not limited to, wood resources, municipal solid waste, wastepaper, crops, and crop residues (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Three major classes of enzymes are used to breakdown cellulosic biomass:
(1) The "endo-1,4-beta-glucanases" or 1,4-beta-D-glucan-4-glucanohydrolases (EC 3.2.1.4), which act randomly on soluble and insoluble 1,4-beta-glucan substrates.
(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.
(3) The "beta-D-glucosidases" or beta-D-glucoside glucohydrolases (EC 3.2.1.21), which act to release D-glucose units from cellobiose and soluble cellodextrins, as well as an array of glycosides.

The polypeptides having endoglucanase activity of the present invention are preferably used in conjunction with other cellulolytic proteins, e.g., exo-1,4-beta-D-glucanases and beta-D-glucosidases, to degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24). The term "cellulolytic proteins" is defined herein as those proteins or mixtures of proteins shown as being capable of hydrolyzing or converting or degrading cellulose under the conditions tested.

The exo-1,4-beta-D-glucanases and beta-D-glucosidases may be produced by any known method known in the art (see, e.g., Bennett, J. W. and LaSure, L. (eds.), *More Gene Manipulations in Fungi*, Academic Press, CA, 1991).

The optimum amounts of a polypeptide having endoglucanase activity and other cellulolytic proteins depends on several factors including, but not limited to, the mixture of component cellulolytic proteins, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, the amount of polypeptide having endoglucanase activity per g of cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of cellulosic material.

In another preferred aspect, the amount of cellulolytic proteins per g of cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 2.5 to about 10 mg per g of cellulosic material.

In the methods of the present invention, the composition may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

The enzymes may be derived or obtained from any suitable origin, including, bacterial, fungal, yeast or mammalian origin. The term "obtained" means herein that the enzyme may have been isolated from an organism which naturally produces the enzyme as a native enzyme. The term "obtained" also means herein that the enzyme may have been produced recombinantly in a host organism, wherein the recombinantly produced enzyme is either native or foreign to the host organism or has a modified amino acid sequence, e.g., having one or more amino acids which are deleted, inserted and/or substituted, i.e., a recombinantly produced enzyme which is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes may also be purified. The term "purified" as used herein covers enzymes free from other components from the organism from which it is derived. The term "purified" also covers enzymes free from components from the native organism from which it is obtained. The enzymes may be purified, with only minor amounts of other proteins being present. The expression "other proteins" relate in particular to other enzymes. The term "purified" as used herein also refers to removal of other components, particularly other proteins and most particularly other enzymes present in the cell of origin of the enzyme of the invention. The enzyme may be "substantially pure," that is, free from other components from the organism in which it is produced, that is, for example, a host organism for recombinantly produced enzymes. In a preferred aspect, the enzymes are at least 75% (w/w), preferably at least 80%, more preferably at least 85%, more preferably at least 90%, more preferably at least 95%, more preferably at least 96%, more preferably at least 97%, even more preferably at least 98%, or most preferably at least 99% pure. In another preferred aspect, the enzyme is 100% pure.

The enzymes used in the present invention may be in any form suitable for use in the processes described herein, such as, for example, a crude fermentation broth with or without cells, a dry powder or granulate, a non-dusting granulate, a liquid, a stabilized liquid, or a protected enzyme. Granulates may be produced, e.g., as disclosed in U.S. Pat. Nos. 4,106,991 and 4,661,452, and may optionally be coated by process known in the art. Liquid enzyme preparations may, for instance, be stabilized by adding stabilizers such as a sugar, a sugar alcohol or another polyol, and/or lactic acid or another organic acid according to established process. Protected enzymes may be prepared according to the process disclosed in EP 238,216.

The methods of the present invention may be used to process a cellulosic material to many useful organic products, chemicals and fuels. In addition to ethanol, some commodity and specialty chemicals that can be produced from cellulose include xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd, L. R., Wyman, C. E., and Gerngross, T. U., 1999, *Biocommodity Engineering*, *Biotechnol. Prog.*, 15: 777-793; Philippidis, G. P., 1996, Cellulose bioconversion technology, in *Handbook on Bioethanol: Production and Utilization*, Wyman, C. E., ed., Taylor & Francis, Washington, D.C., 179-212; and Ryu, D. D. Y., and Mandels, M., 1980, Cellulases: biosynthesis and applications, *Enz. Microb. Technol.*, 2: 91-102). Potential coproduction benefits extend beyond the synthesis of multiple organic products from fermentable carbohydrate. Lignin-rich residues remaining after biological processing can be converted to lignin-derived chemicals, or used for power production.

Conventional methods used to process the cellulosic material in accordance with the methods of the present invention are well understood to those skilled in the art. The methods of the present invention may be implemented using any conventional biomass processing apparatus configured to operate in accordance with the invention.

Such an apparatus may include a batch-stirred reactor, a continuous flow stirred reactor with ultrafiltration, a continuous plug-flow column reactor (Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153).

The conventional methods include, but are not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to glucose and then ferment glucose to ethanol. In SSF, the enzymatic hydrolysis of cellulose and the fermentation of glucose to ethanol is combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF includes the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577).

"Fermentation" or "fermentation process" refers to any fermentation process or any process comprising a fermentation step. A fermentation process includes, without limitation, fermentation processes used to produce fermentation products including alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)). Fermentation processes also include fermentation processes used in the consumable alcohol industry (e.g., beer and wine), dairy industry (e.g., fermented dairy products), leather industry, and tobacco industry.

The present invention further relates to methods of producing a substance, comprising: (a) saccharifying a cellulosic material with a composition comprising an effective amount of a polypeptide having endoglucanase activity; (b) fermenting the saccharified cellulosic material of step (a) with one or more fermentating microorganisms; and (c) recovering the substance from the fermentation. The composition comprising the polypeptide having endoglucanase activity may be in the form of a crude fermentation broth with or without the cells removed or in the form of a semi-purified or purified enzyme preparation or the composition may comprise a host cell of the present invention as a source of the polypeptide having endoglucanase activity in a fermentation process with the biomass.

The substance can be any substance derived from the fermentation. In a preferred embodiment, the substance is an alcohol. It will be understood that the term "alcohol" encompasses a substance that contains one or more hydroxyl moieties. In a more preferred embodiment, the alcohol is arabinitol. In another more preferred embodiment, the alcohol is butanol. In another more preferred embodiment, the alcohol is ethanol. In another more preferred embodiment, the alcohol is glycerol. In another more preferred embodiment, the alcohol is methanol. In another more preferred embodiment, the alcohol is 1,3-propanediol. In another more preferred embodiment, the alcohol is sorbitol. In another more preferred embodiment, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred embodiment, the substance is an organic acid. In another more preferred embodiment, the organic acid is acetic acid. In another more preferred embodiment, the organic acid is acetonic acid. In another more preferred embodiment, the organic acid is adipic acid. In another more preferred embodiment, the organic acid is ascorbic acid. In another more preferred embodiment, the organic acid is citric acid. In another more preferred embodiment, the organic acid is 2,5-diketo-D-gluconic acid. In another more preferred embodiment, the organic acid is formic acid. In another more preferred embodiment, the organic acid is fumaric acid. In another more preferred embodiment, the organic acid is glucaric acid. In another more preferred embodiment, the organic acid is gluconic acid. In another more preferred embodiment, the organic acid is glucuronic acid. In another more preferred embodiment, the organic acid is glutaric acid. In another preferred embodiment, the organic acid is 3-hydroxypropionic acid. In another more preferred embodiment, the organic acid is itaconic acid. In another more preferred embodiment, the organic acid is lactic acid. In another more preferred embodiment, the organic acid is malic acid. In another more preferred embodiment, the organic acid is malonic acid. In another more preferred embodiment, the organic acid is oxalic acid. In another more preferred embodiment, the organic acid is propionic acid. In another more preferred embodiment, the organic acid is succinic acid. In another more preferred embodiment, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred embodiment, the substance is a ketone. It will be understood that the term "ketone" encompasses a substance that contains one or more ketone moieties. In another more preferred embodiment, the ketone is acetone. See, for example, Qureshi and Blaschek, 2003, supra.

In another preferred embodiment, the substance is an amino acid. In another more preferred embodiment, the organic acid is aspartic acid. In another more preferred embodiment, the amino acid is glutamic acid. In another more preferred embodiment, the amino acid is glycine. In another more preferred embodiment, the amino acid is lysine. In another more preferred embodiment, the amino acid is serine. In another more preferred embodiment, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred embodiment, the substance is a gas. In another more preferred embodiment, the gas is methane. In another more preferred embodiment, the gas is $H_2$. In another more preferred embodiment, the gas is $CO_2$. In another more preferred embodiment, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Production of a substance from cellulosic material typically requires four major steps. These four steps are pretreatment, enzymatic hydrolysis, fermentation, and recovery. Exemplified below is a process for producing ethanol, but it will be understood that similar processes can be used to produce other substances, for example, the substances described above.

Pretreatment.

In the pretreatment or pre-hydrolysis step, the cellulosic material is heated to break down the lignin and carbohydrate structure, solubilize most of the hemicellulose, and make the cellulose fraction accessible to cellulolytic enzymes. The heating is performed either directly with steam or in slurry where a catalyst may also be added to the material to speed up the reactions. Catalysts include strong acids, such as sulfuric acid and $SO_2$, or alkali, such as sodium hydroxide. The purpose of the pre-treatment stage is to facilitate the penetration of the enzymes and microorganisms. Cellulosic biomass may also be subject to a hydrothermal steam explosion pre-treatment (See U.S. Patent Application No. 20020164730).

Saccharification.

In the enzymatic hydrolysis step, also known as saccharification, enzymes as described herein are added to the pretreated material to convert the cellulose fraction to glucose and/or other sugars. The saccharification is generally performed in stirred-tank reactors or fermentors under controlled pH, temperature, and mixing conditions. A saccharification step may last up to 200 hours. Saccharification may be carried out at temperatures from about 30° C. to about 65° C., in particular around 50° C., and at a pH in the range between about 4 and about 5, especially around pH 4.5. To produce glucose that can be metabolized by yeast, the hydrolysis is typically performed in the presence of a beta-glucosidase.

Fermentation.

In the fermentation step, sugars, released from the cellulosic material as a result of the pretreatment and enzymatic hydrolysis steps, are fermented to ethanol by a fermenting organism, such as yeast. The fermentation can also be carried out simultaneously with the enzymatic hydrolysis in the same vessel, again under controlled pH, temperature, and mixing conditions. When saccharification and fermentation are performed simultaneously in the same vessel, the process is generally termed simultaneous saccharification and fermentation or SSF.

Any suitable cellulosic substrate or raw material may be used in a fermentation process of the present invention. The substrate is generally selected based on the desired fermentation product, i.e., the substance to be obtained from the fermentation, and the process employed, as is well known in the art. Examples of substrates suitable for use in the methods of present invention include cellulose-containing materials, such as wood or plant residues or low molecular sugars DP1-3 obtained from processed cellulosic material that can be metabolized by the fermenting microorganism, and which may be supplied by direct addition to the fermentation medium.

The term "fermentation medium" will be understood to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism suitable for use in a desired fermentation process. Suitable fermenting microorganisms according to the invention are able to ferment, i.e., convert, sugars, such as glucose, xylose, arabinose, mannose, galactose, or oligosaccharides directly or indirectly into the desired fermentation product. Examples of fermenting microorganisms include fungal organisms, such as yeast. Preferred yeast includes strains of the *Saccharomyces* spp., and in particular, *Saccharomyces cerevisiae*. Commercially available yeast include, e.g., Red Star®/™/ Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

In a preferred embodiment, the yeast is a *Saccharomyces* spp. In a more preferred embodiment, the yeast is *Saccharomyces cerevisiae*. In another more preferred embodiment, the yeast is *Saccharomyces distaticus*. In another more preferred embodiment, the yeast is *Saccharomyces uvarum*. In another preferred embodiment, the yeast is a *Kluyveromyces*. In another more preferred embodiment, the yeast is *Kluyveromyces marxianus*. In another more preferred embodiment, the yeast is *Kluyveromyces fragilis*. In another preferred embodiment, the yeast is a *Candida*. In another more preferred embodiment, the yeast is *Candida pseudotropicalis*. In another more preferred embodiment, the yeast is *Candida brassicae*. In another preferred embodiment, the yeast is a *Clavispora*. In another more preferred embodiment, the yeast is *Clavispora lusitaniae*. In another more preferred embodiment, the yeast is *Clavispora opuntiae*. In another preferred embodiment, the yeast is a *Pachysolen*. In another more preferred embodiment, the yeast is *Pachysolen tannophilus*. In another preferred embodiment, the yeast is a *Bretannomyces*. In another more preferred embodiment, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment glucose to ethanol include, for example, *Zymomonas mobilis* and *Clostridium thermocellum* (Philippidis, 1996, supra).

It is well known in the art that the organisms described above can also be used to produce other substances, as described herein.

The cloning of heterologous genes in *Saccharomyces cerevisiae* (Chen, Z., Ho, N. W. Y., 1993, Cloning and improving the expression of *Pichia stipitis* xylose reductase gene in *Saccharomyces cerevisiae*, *Appl. Biochem. Biotechnol.* 39-40: 135-147; Ho, N. W. Y., Chen, Z, Brainard, A. P., 1998, Genetically engineered *Saccharomyces* yeast capable of effectively cofermenting glucose and xylose, *Appl. Environ. Microbiol.* 64: 1852-1859), or in bacteria such as *Escherichia coli* (Beall, D. S., Ohta, K., Ingram, L. O., 1991, Parametric studies of ethanol production from xylose and other sugars by recombinant *Escherichia coli*, *Biotech. Bioeng.* 38: 296-303), *Klebsiella oxytoca* (Ingram, L. O., Gomes, P. F., Lai, X., Moniruzzaman, M., Wood, B. E., Yomano, L. P., York, S. W., 1998, Metabolic engineering of bacteria for ethanol production, *Biotechnol. Bioeng.* 58: 204-214), and *Zymomonas mobilis* (Zhang, M., Eddy, C., Deanda, K., Finkelstein, M., and Picataggio, S., 1995, Metabolic engineering of a pentose metabolism pathway in ethanologenic *Zymomonas mobilis*, *Science* 267: 240-243; Deanda, K., Zhang, M., Eddy, C., and Picataggio, S., 1996, Development of an arabinose-fermenting *Zymomonas mobilis* strain by metabolic pathway engineering, *Appl. Environ. Microbiol.* 62: 4465-4470) has led to the construction of organisms capable of converting hexoses and pentoses to ethanol (cofermentation).

Yeast or another microorganism typically is added to the degraded cellulose or hydrolysate and the fermentation is ongoing for about 24 to about 96 hours, such as about 35 to about 60 hours. The temperature is typically between about 26° C. to about 40° C., in particular at about 32° C., and at about pH 3 to about pH 6, in particular around pH 4-5.

In a preferred embodiment, yeast or another microorganism is applied to the degraded cellulose or hydrolysate and the fermentation is ongoing for about 24 to about 96 hours, such as typically 35-60 hours. In a preferred embodiments, the temperature is generally between about 26 to about 40° C., in particular about 32° C., and the pH is generally from about pH 3 to about pH 6, preferably around pH 4-5. Yeast or another microorganism is preferably applied in amounts of approximately $10^5$ to $10^{12}$, preferably from approximately $10^7$ to $10^{10}$, especially approximately $5 \times 10^7$ viable count per ml of fermentation broth. During an ethanol producing phase the yeast cell count should preferably be in the range from approximately $10^7$ to $10^{10}$, especially around approximately $2 \times 10^8$. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the mash is distilled to extract the ethanol. The ethanol obtained according to the process of the invention may be used as, e.g., fuel ethanol; drinking ethanol, i.e., potable neutral spirits, or industrial ethanol.

A fermentation stimulator may be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, e.g., Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Recovery.

The alcohol is separated from the fermented cellulosic material and purified by conventional methods of distillation. Ethanol with a purity of up to about 96 vol. % ethanol can be obtained, which can be used as, for example, fuel ethanol, drinking ethanol, i.e., potable neutral spirits, or industrial ethanol.

For other substances, any method known in the art can be used including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, distillation, or extraction.

In the methods of the present invention, the polypeptide having endoglucanase activity and other cellulolytic protein (s) may be supplemented by one or more additional enzyme activities to improve the degradation of the cellulosic material. Preferred additional enzymes are hemicellulases, esterases (e.g., lipases, phospholipases, and/or cutinases), proteases, laccases, peroxidases, or mixtures thereof.

In the methods of the present invention, the additional enzyme(s) may be added prior to or during fermentation, including during or after the propagation of the fermenting microorganism(s).

Signal Peptides

The present invention also relates to nucleic acid constructs comprising a gene encoding a protein, wherein the gene is operably linked to a nucleotide sequence encoding a signal peptide comprising or consisting of amino acids 1 to 22 of SEQ ID NO: 4, amino acids 1 to 19 of SEQ ID NO: 6, or amino acids 1 to 18 of SEQ ID NO: 8, wherein the gene is foreign to the nucleotide sequence.

In a preferred aspect, the nucleotide sequence comprises or consists of nucleotides 13 to 79 of SEQ ID NO: 1. In another preferred aspect, the nucleotide sequence comprises or consists of nucleotides 17 to 73 of SEQ ID NO: 3. In another preferred aspect, the nucleotide sequence comprises or consists of nucleotides 53 to 106 of SEQ ID NO: 5.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Thielavia terrestris* NRRL 8126 and *Cladorrhinum foecundissimum* ATCC 62373 were used as the source of the glycosyl hydrolase Family 7 (CEL7) polypeptides having endoglucanase activity. *Aspergillus oryzae* JaL250 strain (WO 99/61651) was used for expression of the CEL7 polypeptides from *Thielavia terrestris*, and *Aspergillus oryzae* strain HowB104 (alpha-amylase negative) was used for expression of the CEL7 polypeptide from *Cladorrhinum foecundissimum*.

Media

YEG medium was composed of 0.5% yeast extract and 2% glucose.

Potato dextrose medium was composed per liter of 39 grams of potato dextrose (Difco).

PDA plates were composed per liter of 39 grams of potato dextrose agar.

M400 medium was composed per liter of 50 g maltodextrin, 2 g of $MgSO_4.7H_2O$, 2 g of $KH_2PO_4$, 4 g of citric acid, 8 g of yeast extract, 2 g of urea, 0.5 ml of AMG trace metals solution, and 0.5 g of calcium chloride.

MDU2BP medium was composed per liter of 45 g of maltose, 1 g of $MgSO_4.7H_2O$, 1 g of NaCl, 2 g of $K_2SO_4$, 12 g of $KH_2PO_4$, 7 g of yeast extract, 2 g of urea, and 0.5 ml of AMG trace metals solution, pH adjusted to 5.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

NNCYPmod medium was composed per liter of 1.0 g of NaCl, 5.0 g of $NH_4NO_3$, 0.2 g of $MgSO_4.7H_2O$, 0.2 g of $CaCl_2$, 2.0 g of citric acid, 1.0 g of Bacto Peptone, 5.0 g of yeast extract, COVE trace metals solution, and sufficient $K_2HPO_4$ to achieve a final pH of approximately 5.4.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

LB medium was composed per liter of 10 g of tryptone, 5 g of yeast extract, and 5 g of sodium chloride.

LB plates were composed per liter of 10 g of tryptone, 5 g of yeast extract, 5 g of sodium chloride, and 15 g of Bacto Agar.

SOC medium was composed of 2% tryptone, 0.5% yeast extract, 10 mM NaCl, 2.5 mM KCl, 10 mM $MgCl_2$, 10 mM $MgSO_4$, and filter-sterilized glucose to 20 mM, added after autoclaving.

Freezing medium was composed of 60% SOC medium and 40% glycerol.

2×YT medium was composed per liter of 16 g of tryptone, 10 g of yeast extract, 5 g of NaCl, and 15 g of Bacto agar.

PD medium with cellulose was composed per liter of 24 grams potato dextrose (Difco) and 30 grams of Solcafloc (Diacel available from Dicalie-Europe-Nord, Gent, Belgium).

SC-agar was composed per liter of SC-URA medium (with glucose or galactose as indicated) and 20 g of agar.

0.1% AZCL HE cellulose SC agar plates with galactose were composed per liter of SC-URA medium with galactose, 20 g of agar, and 0.1% AZCL HE cellulose (Megazyme, Wicklow, Ireland).

Example 1

Identification of CEL7C Endoglucanase from *Thielavia terrestris* NRRL 8126

An agarose plug from a fresh plate of *Thielavia terrestris* NRRL 8126 grown on NNCYPmod medium supplemented with 1% Sigmacell (Sigma Chemical Co., St. Louis, Mo., USA) was inoculated into 50 ml of NNCYPmod medium supplemented with 1% glucose and incubated at 45° C. and 200 rpm for 25 hours. Two ml of this culture was used to inoculate 15×100 ml (500 ml flask) and 2×50 ml (250 ml flask) of NNCYPmod medium supplemented with 2% Sigmacell-20 and was incubated at 45° C., 200 rpm for 4 days. The cultures were pooled and centrifuged at 3000×g for 10 minutes and the supernatant was filtered through a Nalgene 281-5000 glass fiber prefilter (Nalge Nunc Intl, Rochester, N.Y., USA). The filtrate was cooled to 4° C. for storage.

The filtrate was then further filtered (GP Express membrane, polyethersulfone, 0.22 μm, Millipore, Bedford, Mass., USA), buffer exchanged with 50 mM sodium acetate pH 5.0 (Pall Filtron, North Borough, Mass., 10 kDa polyethersulfone membrane, approximately 10-20 psi), and concentrated using an Amicon ultrafiltration device (Millipore, Bedford, Mass., 10 kDa membrane, 40 psi, 4° C.). The concentrated sample was desalted and buffer exchanged by passing over a 10DG EconoPAC column (Bio-Rad, Hercules, Calif., USA) equilibrated and run with 20 mM Tris-HCl pH 8.2. Protein concentrations were determined using a BCA Protein Assay Kit (Pierce, Rockford, Ill., USA) in which bovine serum albumin was used as a protein standard. Fractions containing protein were loaded onto a 5-ml Hi Trap Q Sepharose™ Fast Flow column (Amersham Pharmacia, Uppsala Sweden) equilibrated with 20 mM Tris-HCl, pH 8.2 on an AKTA FPLC System (Amersham Pharmacia, Uppsala Sweden) run at a flow rate of 2 ml per minute. Prior to elution the column was washed with five column volumes of starting buffer. Bound material was eluted with a linear gradient of 0 to 1.0 M NaCl (20 column volumes; 2 ml fractions) in 20 mM Tris-HCl pH 8.2. Based on the UV profile at 280 nm, individual fractions were pooled for further analysis. The pooled fractions eluting between approximately 10 and 210 mM NaCl were concentrated using an Amicon apparatus, as described above. An aliquot of this material was electrophoresed on an 8-16% Tris-Glycine SDS-PAGE gel (BioRad Laboratories, Hercules, Calif., USA) and electrophoresed at 200 V for 1 hour. Precision molecular weight standards (BioRad, Hercules, Calif., USA) were included and used for molecular weight determination. Gels were stained for protein using Biosafe Coomassie Stain (BioRad, Hercules, Calif., USA) according to the manufacturer's suggested protocol.

A band migrating at approximately 61 kDa was excised from the gel and subjected to in-gel digestion and de novo sequencing using tandem mass spectrometry.

In-Gel Digestion of Polypeptides for Peptide Sequencing.

A MultiPROBE® II Liquid Handling Robot (PerkinElmer Life and Analytical Sciences, Boston, Mass., USA) was used to perform the in-gel digestions. Two dimensional gel spots containing polypeptides of interest were reduced with 50 μl of 10 mM dithiothreitol (DTT) in 100 mM ammonium bicarbonate pH 8.0 for 30 minutes at room temperature. Following reduction, the gel pieces were alkylated with 50 μl of 55 mM iodoacetamide in 100 mM ammonium bicarbonate pH 8.0 for 20 minutes. The dried gel pieces were allowed to swell in a trypsin digestion solution (6 ng/μl sequencing grade trypsin (Promega, Madison, Wis., USA) in 50 mM ammonium bicarbonate pH 8) for 30 minutes at room temperature, followed by an 8 hour digestion at 40° C. Each of the reaction steps described was followed by numerous washes and pre-washes with the appropriate solutions following the manufacturer's standard protocol. Fifty μl of acetonitrile was used to dehydrate the gel between reactions and gel pieces were air dried between steps. Peptides were extracted twice with 1% formic acid/2% acetonitrile in HPLC grade water for 30 minutes. Peptide extraction solutions were transferred to a 96 well skirted PCR type plate (ABGene, Rochester, N.Y., USA) that had been cooled to 10-15° C. and covered with a 96-well plate lid (PerkinElmer Life and Analytical Sciences, Boston, Mass., USA) to prevent evaporation. Plates were further stored at 4° C. until mass spectrometry analysis could be performed.

Peptide Sequencing by Tandem Mass Spectrometry.

For peptide sequencing by tandem mass spectrometry, a Q-T of Micro™ hybrid orthogonal quadrupole time-of-flight mass spectrometer (Waters Micromass® MS Technologies, Milford, Mass., USA) was used for LC-MS/MS analysis. The Q-T of Micro™ mass spectrometer was fitted with an Ultimate™ capillary and nano-flow HPLC system (Dionex, Sunnyvale, Calif., USA) which had been coupled with a FAMOS micro autosampler (Dionex, Sunnyvale, Calif., USA) and a Switchos II column switching device (Dionex, Sunnyvale, Calif., USA) for concentrating and desalting samples. Six μl of the recovered peptide solution from the in-gel digestion was loaded onto a guard column (300 μm ID×5 cm, C18 PepMap™) (Dionex, Sunnyvale, Calif., USA) fitted in the injection loop and washed with 0.1% formic acid in water at 40 μl/minute for 2 minutes using a Switchos II pump (Dionex, Sunnyvale, Calif., USA). Peptides were separated on a 75 μm ID×15 cm, C18, 3 μm, 100 Å PepMap™ nanoflow fused capillary column (Dionex, Sunnyvale, Calif., USA) at a flow rate of 175 nl/minute from a split flow of 175 μl/minute using a NAN-75 calibrator (Dionex, Sunnyvale, Calif., USA). The linear elution gradient was 5% to 60% acetonitrile in 0.1% formic acid applied over a 45 minute period. The column eluent was monitored at 215 nm and introduced into the Q-T of Micro™ mass spectrometer through an electrospray ion source fitted with the nanospray interface. The Q-T of Micro™ mass spectrometer was fully microprocessor controlled using MassLynx™ software version 3.5 (Waters Micromass® MS Technologies, Milford, Mass., USA). Data was acquired in survey scan mode and from a mass range of 50 to 2000 m/z with switching criteria for MS to MS/MS to include an ion intensity of greater than 10.0 counts/second and charge states of +2, +3, and +4. Analysis spectra of up to 4 co-eluting species with a scan time of 1.9 seconds and inter-scan time of 0.1 seconds could be obtained. A cone voltage of 65 volts was typically used and the collision energy was programmed to be varied according to the mass and charge state of the eluting peptide and in the range of 10-60 volts. The acquired spectra were combined, smoothed, and centered in an automated fashion and a peak list generated. The generated peak list was searched against selected databases using ProteinLynx™ Global Server 1.1 software (Waters Micromass® MS Technologies, Milford, Mass., USA). Results from the ProteinLynx™ searches were evaluated and un-identified proteins were analyzed further by evaluating the MS/MS spectrums of each ion of interest and de novo sequence determined by identifying the y and b ion series and matching mass differences to the appropriate amino acid.

Peptide sequences of the *Thielavia terrestris* CEL7C endoglucanase from de novo sequencing by mass spectrometry were obtained from several multiply charged ions for the approximately 61 kDa polypeptide gel band. A doubly charged tryptic peptide ion of 933.49 m/z was determined to be Phe-[Ile or Leu]-Thr-Asp-Asp-Gly-Thr-Thr-Ser-Gly-Thr-[Ile-Leu]-Asn-[Gln-Lys]-[Ile-Leu]-[Gln-Lys]-Arg (amino acids 256 to 272 of SEQ ID NO: 2). A second doubly charged tryptic peptide ion of 1108.58 was also de novo sequenced and a partial sequence was determined to be Tyr-Gly-Pro-Gly-[Ile-Leu]-Thr-Val-Asp-Thr-Ser-[Lys-Gln] (amino acids 238 to 248 of SEQ ID NO: 2).

Example 2

*Thielavia terrestris* NRRL 8126 Genomic DNA Extraction

*Thielavia terrestris* NRRL 8126 was grown in 25 ml of YEG medium at 37° C. and 250 rpm for 24 hours. Mycelia were then collected by filtration through Miracloth™ (Calbiochem, La Jolla, Calif., USA) and washed once with 25 ml of 10 mM Tris-1 mM EDTA (TE) buffer. Excess buffer was drained from the mycelia preparation, which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 µg per ml and the mixture was then incubated at 37° C. for 30 minutes. Proteinase K (200 µg/ml) was added and the tube was incubated an additional one hour at 37° C. Finally, the sample was centrifuged at 12,000×g for 15 minutes, and the supernatant was applied to a Qiaprep® 8 manifold (QIAGEN Inc., Valencia, Calif., USA). The columns were washed twice with 1 ml of PB (QIAGEN Inc., Valencia, Calif., USA) and 1 ml of PE (QIAGEN Inc., Valencia, Calif., USA) under vacuum. The isolated DNA was eluted with 100 µl of TE buffer, precipitated with ethanol, washed with 70% ethanol, dried under vacuum, resuspended in TE buffer, and stored at 4° C.

To generate genomic DNA for PCR amplification, *Thielavia terrestris* NRRL 8126 was grown in 50 ml of NNCYP medium supplemented with 1% glucose in a baffled shake flask at 42° C. and 200 rpm for 24 hours. Mycelia were harvested by filtration, washed twice in TE buffer, and frozen under liquid nitrogen. A pea-size piece of frozen mycelia was suspended in 0.7 ml of 1% lithium dodecyl sulfate in TE buffer and disrupted by agitation with an equal volume of 0.1 mm zirconia/silica beads (Biospec Products, Inc., Bartlesville, Okla., USA) for 45 seconds in a FastPrep FP120 (ThermoSavant, Holbrook, N.Y., USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 µl of 0.1×TE buffer and incubated with 1 µl of DNase-free RNase A at 37° C. for 20 minutes. Ammonium acetate was added to 2.5 M and the DNA was precipitated with 2 volumes of ethanol. The pellet was washed in 70% ethanol, air dried, and resuspended in TE buffer.

Example 3

Cloning of a Gene Encoding a CEL7C Endoglucanase from *Thielavia terrestris* NRRL 8126

Mass spectrometry, as described in Example 1, revealed a partial sequence of a doubly charged peptide of mass 933.49 to be TDDGTTSGT[I/L]NQ[I/L]QR (amino acids 258 to 272 of SEQ ID NO: 2). An antisense strand oligonucleotide CODEHOP primer (Rose et al., 1998, *Nucleic Acids Res.* 26: 1628-35) was designed to the portion of the sequence shown above in bold (amino acids 259 to 267 of SEQ ID NO: 2). The primer sequence is shown below.

(SEQ ID NO: 7)
5'-AGGGTGCCGCTGGTNGTNCCRTCRTC-3'

A second CODEHOP sense strand primer was designed based on conserved sequences present in many glycosyl hydrolases of Family 7, specifically AGAKYGTGYCD (amino acids 164 to 173 of SEQ ID NO: 2; residues shown in bold were found to be conserved in CEL7C). The primer sequence is shown below.

(SEQ ID NO: 8)
5'-AGCTGGTGCTAAATATGGTACTGGNTAYTGYGA-3'

PCR amplification was performed in a volume of 30 µl containing 1× AmpliTaq buffer (Applied Biosystems, Inc., Foster City, Calif., USA), 1.5 units of AmpliTaq DNA polymerase (Applied Biosystems, Inc., Foster City, Calif., USA), 1 µM each of the sense and antisense primers, and approximately 1 µg of genomic DNA from *Thielavia terrestris* NRRL 8126. Amplification was performed in a RoboCycler® (Stratagene, La Jolla, Calif., USA) programmed for 1 cycle at 96° C. for 3 minutes and at 72° C. for 3 minutes (during which DNA polymerase was added); and 35 cycles each at 94° C. for 45 seconds, 52° C., 55° C., or 58° C. for 45 seconds, and 72° C. for 1 minute, followed by a final extension of 7 minutes at 72° C.

The reaction products were fractionated by 3% agarose gel electrophoresis using 40 mM Tris base-20 mM sodium acetate-1 mM disodium EDTA (TAE) buffer and a band of approximately 300 bp was excised, purified using a QIAEX® II Gel Extraction Kit (QIAGEN Inc., Valencia, Calif., USA), and subcloned using a TOPO TA Kit (Invitrogen, Carlsbad, Calif., USA). The plasmid from one *E. coli* transformant was sequenced and found to contain an insert of 315 bp coding for a predicted glycosyl hydrolase Family 7 protein (CEL7C). This plasmid was designated pPH32 (FIG. 1).

Example 4

Identification of CEL7E Endoglucanase from *Thielavia terrestris* NRRL 8126

An agarose plug from a fresh plate of *Thielavia terrestris* NRRL 8126 grown on NNCYPmod medium supplemented with 1% Sigmacell was inoculated into 25 ml of NNCYPmod medium supplemented with 2% Sigmacell and incubated at 42° C. and 150 rpm for 3 days. The broth was filtered through a Nalgene 281-5000 glass fiber prefilter. The filtrate was cooled to 4° C. for storage.

Two-Dimensional Polyacrylamide Gel Electrophoresis.

Three ml of filtrate from the pooled cultures described in Example 1 was precipitated by adding 30 µl of beta-mercaptoethanol and 300 µl of saturated trichloroacetic acid (saturated solution in water at 4° C.), and incubating for 10 minutes on ice followed by addition of 30 ml of ice-cold acetone and further incubation on ice for 30 minutes. The precipitated solution was centrifuged at 10,000×g for 10 minutes at 4° C., the supernatant decanted, and the pellet rinsed twice with ice-cold acetone and air dried. The dried pellet was dissolved in 0.2 ml of isoelectric focusing (IEF) sample buffer (9.0 M urea, 3.0% (wt/v) 3-[(3-cholamidopropyl) dimethyl-ammonium]-1-propanesulfonate (CHAPS, Pierce Chemical Co. Rockford, Ill., USA), 1% (v/v) pH 4-7 ampholytes, 1% beta-mercaptoethanol, and 0.005% bromophenol blue in distilled water). Urea stock solution was de-ionized using AG 501-X8 (D), 20-5-mesh, mixed bed resin from BioRad Laboratories (Hercules, Calif., USA). The de-ionized solution was stored at −20° C. The resulting mixture was allowed to solubilize for several hours with gentle mixing on a LabQuake™ Shaker (Lab Industries, Berkeley, Calif., USA). The sample buffer-protein mixture was applied to an 11 cm IPG strip (BioRad Laboratories, Hercules, Calif., USA) in an IPG rehydration tray (Amersham Biosciences, Piscataway, N.J., USA). A 750 µl aliquot of dry-strip cover fluid (Amersham Biosciences, Piscataway, N.J., USA) was layered over the IPG strips to prevent evaporation and allowed to rehydrate for 12 hours while applying 30 volts using an IPGPhor Isoelectric Focusing Unit (Amersham Biosciences, Piscataway, N.J., USA) at 20° C. The IPGPhor Unit was programmed for constant voltage but with a maximum current of 50 µA per strip. After 12 hours of rehydration, the isoelectric focusing conditions were as follows: 1 hour at 200 volts, 1 hour at 500 volts, and 1 hour at 1000 volts. Then a gradient was applied from 1000 volts to 8000 volts for 30 minutes and isoelectric focusing was programmed to run at 8000 volts and was complete when >30,000 volt hours was achieved. IPG gel strips were reduced and alkylated before the second dimension analysis by first reducing for 15 minutes in 100 mg of dithiothreitol per 10 ml of SDS-equilibration buffer (50 mM Tris HCl pH 8.8, 6.0 M urea, 2% (w/v) sodium dodecylsulfate (SDS), 30% glycerol, and 0.002% (w/v) bromophenol blue) followed by 15 minutes of alkylation in 250 mg iodoacetamide per 10 ml of equilibration buffer in the dark. The IPG strips were rinsed quickly in SDS-PAGE running buffer (Invitrogen/Novex, Carlsbad, Calif., USA) and placed on an 11 cm, 1 well 8-16% Tris-Glycine SDS-PAGE gel (BioRad Laboratories, Hercules, Calif., USA) and electrophoresed using a Criterion electrophoresis unit (BioRad Laboratories, Hercules, Calif., USA) at 50 volts until the sample entered the gel and then the voltage was increased to 200 volts and allowed to run until the bromophenol blue dye reached the bottom of the gel.

Polypeptide Detection.

The two dimensional gel was stained with a fluorescent SYPRO Orange Protein Stain (Molecular Probes, Eugene, Oreg., USA). Fluorescent staining methods were optimized and adapted from Malone et al., 2001, *Electrophoresis*, 22, 919-932. SDS-PAGE gels were fixed in 40% ethanol, 2% acetic acid, and 0.0005% SDS on a platform rocker for 1 hour to overnight. Fixing solution was removed and replaced with three repeated wash steps consisting of 2% acetic acid and 0.0005% SDS for 30 minutes each. Gels were stained for 1.5 hours to overnight in the dark with 2% acetic acid, 0.0005% SDS, and 0.02% SYPRO Orange Protein Stain. Staining and de-staining was further optimized to improve reproducibility and automation on a Hoefer Processor Plus Staining Unit (Amersham Biosciences, Piscataway, N.J., USA). Images of the fluorescent stained SDS-PAGE gels were obtained by scanning on a Molecular Dynamics STORM 860 Imaging System (Amersham Biosciences, Piscataway, N.J., USA) using blue fluorescence and 200 µm pixel sizes and a photomultiplier tube gain of 800 V. Images were viewed and adjusted using ImageQuant software version 5.0 (Amersham Biosciences, Piscataway, N.J., USA). Gels were further visualized on a Dark Reader Blue transilluminator with an orange filter (Clare Chemical Co, Denver, Colo., USA). Observed protein gel spots were excised using a 2 mm Acu-Punch Biopsy Punch (Acuderm Inc., Ft. Lauderdale, Fla., USA) and stored in ninety-six well plates that were pre-washed with 0.1% trifluoroacetic acid (TFA) in 60% acetonitrile followed by two additional washes with HPLC grade water. The stained two-dimensional gel spots were stored in 25-50 µl of water in the pre-washed plates at −20° C. until digested.

A 2D gel spot corresponding to an approximate molecular weight of 50 kDa and an approximate isoelectric point of 5.0 was in-gel digested with trypsin and subjected to de novo sequencing as described in Example 1. A doubly charged tryptic peptide ion of 1114.516 m/z was determined to be Ser-Pro-Leu-Asn-Pro-Ala-Gly-Ala-Thr-Tyr-Gly-Thr-Gly-Tyr-Cam-Asp-Ala-Gln-Cam-Pro-Lys (amino acids 156 to 176 of SEQ ID NO: 5 where Cam is carboxyamidomethyl-cysteine).

A sense strand oligonucleotide CODEHOP primer was designed to a portion of the sequence shown in bold above (168 to 176 of SEQ ID NO: 4). The primer sequence is shown below.

```
                                            (SEQ ID NO: 9)
   5'-GGCTACTGCGACGCCCARTGYCNAA-3'
```

A second CODEHOP antisense strand primer was designed based on conserved sequences present in many glycosyl hydrolases of Family 7, specifically CCNEMDIWEAN (all amino acids were subsequently found to be conserved in CEL7E at 193 to 203 of SEQ ID NO: 4). The primer sequence was:

```
                                           (SEQ ID NO: 10)
   5'-CCTCCCAGATRTCCATYTCGTTRCARCA-3'
```

PCR was performed in a volume of 30 µl containing 1× AmpliTaq buffer, 1.5 units of Taq DNA polymerase (New England Biolabs, Ipswich, Mass., USA), 1 µM each of the sense and antisense primers, and approximately 1 µg of genomic DNA from *Thielavia terrestris* NRRL 8126 (prepared as described in Example 2). Amplification was performed in a Stratagene Robocycler® programmed for 1 cycle at 96° C. for 3 minutes and 72° C. for 3 minutes (during which DNA polymerase was added), 35 cycles each at 94° C. for 45 seconds, 53° C., 56° C., or 59° C. for 45 seconds, and 72° C. for 1 minute, followed by a final extension of 7 minutes at 72° C.

Figure 2:
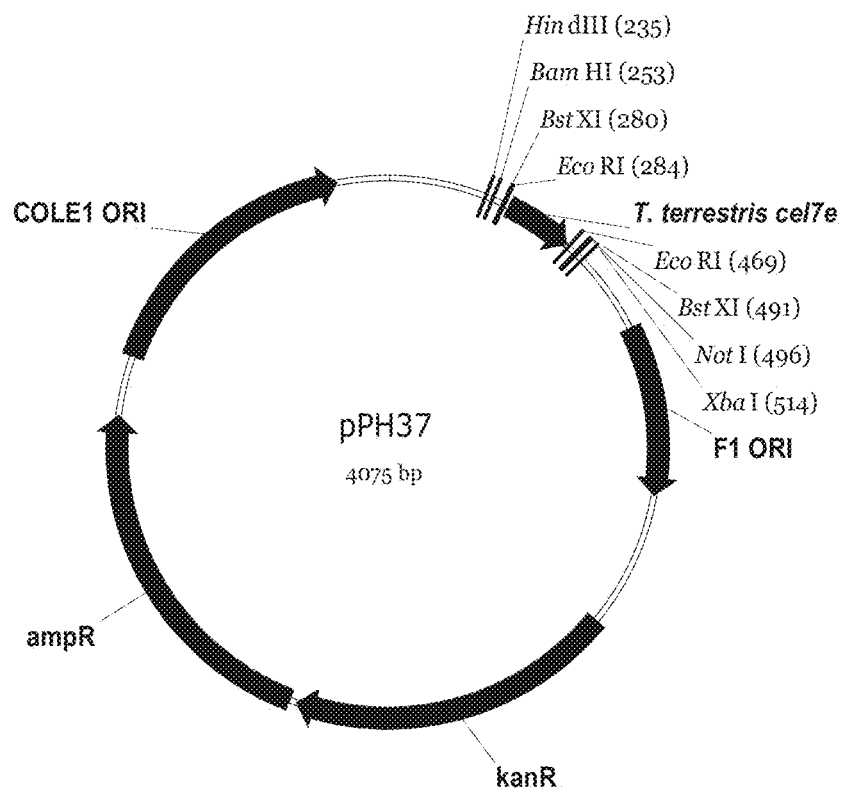
FIG. 2 shows a restriction map of pPH37.

The reaction products were fractionated on a 3% agarose gel using TAE buffer and a band of approximately 180 bp was excised, purified using a QIAEX® II Gel Extraction Kit (QIAGEN Inc., Valencia, Calif., USA), and subcloned using a TOPO TA Kit (Invitrogen, Carlsbad, Calif., USA). The plasmid from one *E. coli* transformant was sequenced and found to contain an insert of 169 bp coding for a predicted glycosyl hydrolase Family 7 protein (CEL7E). This plasmid was designated pPH37 (FIG. 2).

Example 5

Thielavia terrestris NRRL 8126 Genomic DNA Library Construction

Genomic DNA libraries were constructed using the bacteriophage cloning vector λZipLox (Life Technologies, Gaithersburg, Md., USA) with E. coli Y1090ZL cells (Life Technologies, Gaithersburg, Md., USA) as a host for plating and purification of recombinant bacteriophage and E. coli DH10Bzip (Life Technologies, Gaithersburg, Md., USA) for excision of individual pZL1 clones containing the GH61B gene.

Thielavia terrestris NRRL 8126 genomic DNA, prepared as described in Example 2 was partially digested with Tsp 509I and size-fractionated on 1% agarose gels using TAE buffer. DNA fragments migrating in the size range 3-7 kb were excised and eluted from the gel using Prep-a-Gene reagents (BioRad Laboratories, Hercules, Calif., USA). The eluted DNA fragments were ligated with Eco RI-cleaved and dephosphorylated λZipLox vector arms (Life Technologies, Gaithersburg, Md., USA), and the ligation mixtures were packaged using commercial packaging extracts (Stratagene, La Jolla, Calif., USA). The packaged DNA libraries were plated and amplified in E. coli Y1090ZL cells. The unamplified genomic DNA library contained $3.1 \times 10^6$ pfu/ml (background titers with no DNA were $2.0 \times 10^4$ pfu/ml.

Example 6

Identification of Thielavia terrestris NRRL 8126 cel7c and cel7e Clones

Thielavia terrestris cel7c and cel7e gene probe fragments were amplified from pPH32 and pPH37, respectively, using primers homologous to the TOPO vector and Herculase® DNA Polymerase (Stratagene, La Jolla, Calif., USA), as shown below.

```
                               (SEQ ID NO: 11)
5'-CTTGGTACCGAGCTCGGATCCACTA-3'

(SEQ ID NO: 12)
5'-ATAGGGCGAATTGGGCCCTCTAGAT-3'
```

Fifty picomoles of each of the primers were used in a PCR reaction containing 10 ng of pPH32 or pPH37, 1× Herculase® Amplification Buffer (Stratagene, La Jolla, Calif., USA), 1 µl of 10 mM blend of dATP, dTTP, dGTP, and dCTP, and 2.5 units of Herculase® DNA Polymerase in a final volume of 50 µl. Amplification was performed in a Stratagene Robocycler® programmed for 1 cycle at 94° C. for 1 minute; and 20 cycles each at 94° C. for 30 seconds, 55° C. for 30 seconds, and 72° C. for 1 minute. The heat block then went to a 4° C. soak cycle. The reaction products were isolated on a 1.0% agarose gel using TAE buffer where three <400 bp product bands were excised from the gel and purified using a QIAquick® Gel Extraction Kit (QIAGEN Inc., Valencia, Calif., USA) according to the manufacturer's instructions. Twenty five ng of each fragment was radiolabeled with $^{32}$P using a Prime-It® II Kit (Stratagene, La Jolla, Calif., USA).

Approximately 90,000 plaques from the library described in Example 5 were screened by plaque-hybridization using the two labeled PCR fragments as the probes. The DNA was cross-linked onto membranes (Hybond N+, Amersham, Arlington Heights, Ill., USA) using a UV Stratalinker (Stratagene, La Jolla, Calif., USA). Each $^{32}$P-radiolabeled gene fragment was denatured by adding sodium hydroxide to a final concentration of 0.1 M, and added to a hybridization solution containing 6×SSPE, 7% SDS at an activity of approximately $1 \times 10^6$ cpm per ml of hybridization solution. Each of the mixtures was incubated overnight at 55° C. in a shaking water bath. Following incubation, the membranes were washed 3 times for 15 minutes in 0.2×SSC with 0.1% SDS at 65° C. The membranes were dried on blotting paper for 15 minutes, wrapped in SaranWrap™, and exposed to X-ray film overnight at 70° C. with intensifying screens (Kodak, Rochester, N.Y., USA).

Figure 3:
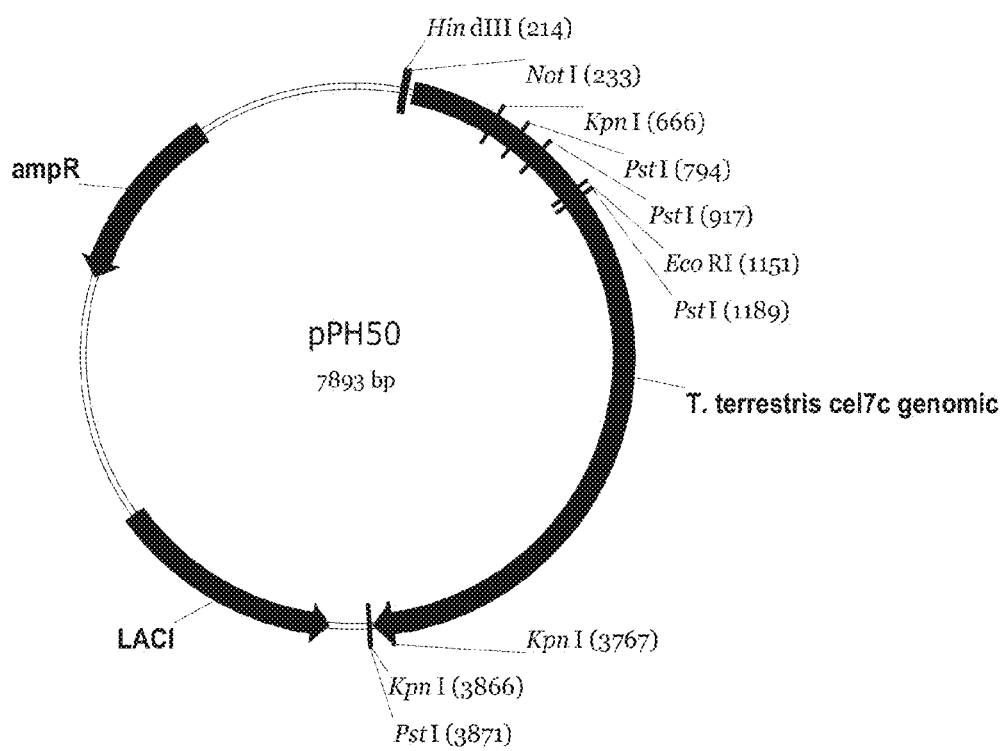
FIG. 3 shows a restriction map of pPH50.
Figure 4:
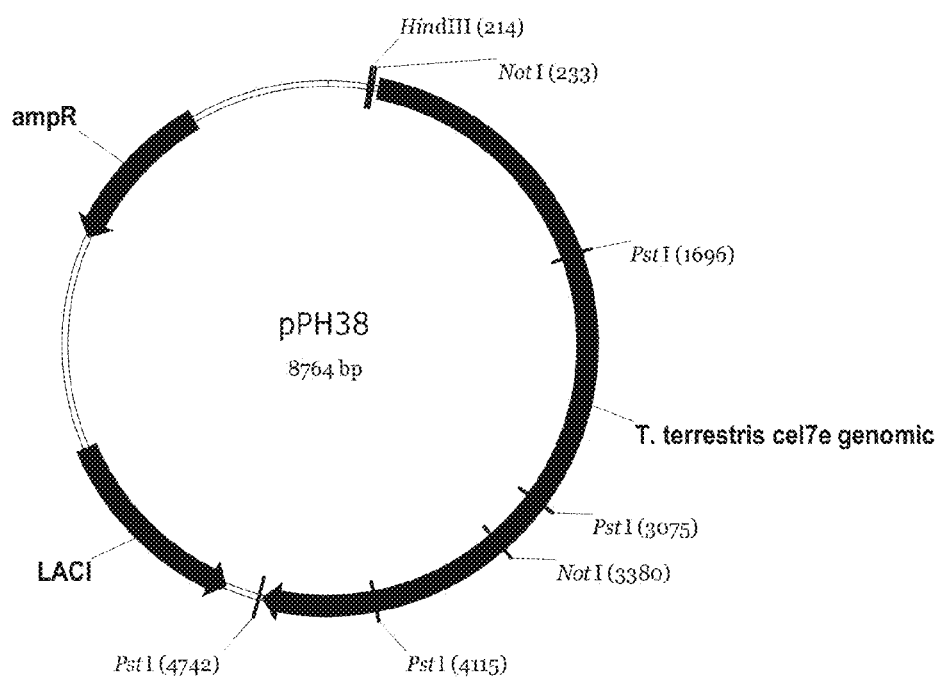
FIG. 4 shows a restriction map of pPH38.

Based on the production of strong hybridization signals with the probes described above, several plaques were chosen for further study. The plaques were purified twice in E. coli Y1090ZL cells and the inserted genes and pZL1 plasmid were subsequently excised from the λZipLox vector as pZL1-derivatives (D'Alessio et al., 1992, Focus® 14:76) using in vivo excision by infection of E. coli DH10BZL cells (Life Technologies, Gaithersburg, Md., USA). The colonies were inoculated into three ml of LB medium supplemented with 50 µg of ampicillin per ml and grown overnight at 37° C. Miniprep DNA was prepared from each of these cultures using a BioRobot 9600 (QIAGEN Inc., Valencia, Calif., USA). A clone designated pPH50 (FIG. 3) was shown by DNA sequencing to contain the full-length genomic gene for cel7c and a clone designated pPH38 (FIG. 4) was shown by DNA sequencing to contain the full-length gene for cel7e.

E. coli PaHa50 containing plasmid pPH50 (FIG. 3) and E. coli PaHa38 containing plasmid pPH38 (FIG. 4) were deposited with the Agricultural Research Service Patent Culture Collection, Northern Regional Research Center, 1815 University Street, Peoria, Ill., 61604, as NRRL B-30899 and NRRL B-30896, respectively, with a deposit date of Feb. 23, 2006.

Example 7

Characterization of the Thielavia terrestris Genomic Sequences Encoding CEL7C and CEL7E Endoglucanases DNA sequencing of the Thielavia terrestris cel7c and cel7e genomic clones was performed with an Applied Biosystems Model 3700 Automated DNA Sequencer using version 3.1 BigDye™ terminator chemistry and dGTP chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

Gene models for the Thielavia terrestris cel7c and cel7e genomic DNA sequences were constructed based on similarity to homologous genes from Trichoderma reesei (accession number Q5BMS5) and Fusarium oxysporum (accession number P46237).

The nucleotide sequence (SEQ ID NO: 1) and deduced amino acid sequence (SEQ ID NO: 2) of the Thielavia terrestris cel7C gene are shown in FIGS. 5A and 5B. The coding sequence is 1452 bp including the stop codon and is interrupted by an intron of 57 bp. The encoded predicted protein is 464 amino acids. The % G+C of the coding sequence of the gene is 63.7% and the mature polypeptide coding sequence is 63.8%. Using the SignalP program (Nielsen et al., 1997, Protein Engineering 10:1-6), a signal peptide of 22 residues was predicted. The predicted mature protein contains 442 amino acids with a molecular mass of 46.5 kDa. Analysis of the deduced amino acid sequence of the cel7c gene with the InterProScan program (Zdobnov and Apweiler, 2001, *Bioinformatics* 17: 847-848) showed that the CEL7C polypeptide contained the domain signature of glycoside hydrolase Family 7 (InterPro accession number IPR001722) from approximately amino acids 2 to 376 of the mature polypeptide. CEL7C also contained the sequence signature of the fungal cellulose binding domain. This sequence signature known as Prosite pattern PS00562 (Sigrist et al., 2002, *Brief Bioinform.* 3: 265-274) was found from approximately amino acids 414 to 441 of the mature polypeptide.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the CEL7C mature polypeptide having endoglucanase activity shares 76% and 70% identity (excluding gaps) to the deduced amino acid sequences of two glycosyl hydrolase Family 7 proteins from *Aspergillus fumigatus* and *Trichoderma reesei*, respectively (accession numbers Q4WCM9 and P07981, respectively).

Figure 6A:
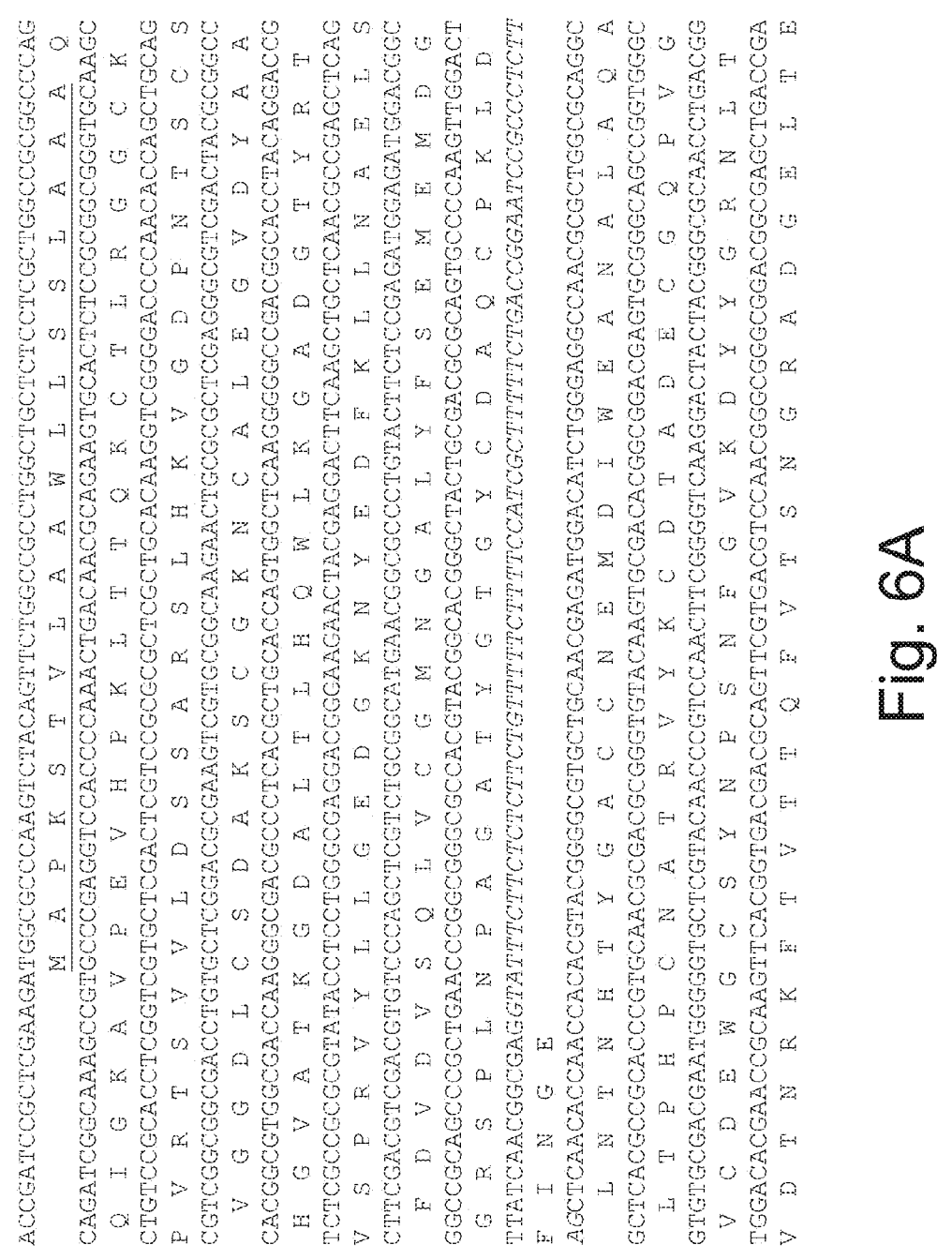

The nucleotide sequence (SEQ ID NO: 3) and deduced amino acid sequence (SEQ ID NO: 4) of the *Thielavia terrestris* cel7e gene are shown in FIGS. 6A and 6B. The coding sequence is 1336 bp including the stop codon and is interrupted by an intron of 64 bp. The encoded predicted protein is 423 amino acids. The % G+C of the coding sequence of the gene is 66.6% and the mature polypeptide coding sequence is 66.5%. Using the SignalP program (Nielsen et al., 1997, supra), a signal peptide of 19 residues was predicted. The predicted mature protein contains 404 amino acids with a molecular mass of 43.4 kDa. Analysis of the deduced amino acid sequence of the cel7e gene with the InterProScan program (Zdobnov and Apweiler, 2001, supra) showed that the CEL7E polypeptide contained the domain signature of glycoside hydrolase Family 7 (InterPro accession number IPR001722) from approximately amino acids 2 to 400 of the mature polypeptide.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Thielavia terrestris* gene encoding the CEL7E mature polypeptide having endoglucanase activity shares 65%, 63%, and 59% identity (excluding gaps) to the deduced amino acid sequences of three glycosyl hydrolase Family 7 proteins from *Neurospora crassa*, *Talaromyces emersonii* and *Aspergillus oryzae*, respectively (accession numbers Q7RXC7, CAC94521.1 and O13455, respectively).

Example 8

Construction of pAILo2 Expression Vector

Expression vector pAILo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using Big-Dye™ terminator chemistry (Applied Biosystems, Inc., Foster City, Calif., USA). Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor™ in vitro Site-Directed Mutagenesis Kit (Promega, Madison, Wis., USA) according to the manufacturer's instructions using the following primers (underlined nucleotide represents the changed base):

```
AMDS3NcoMut (2050):
                                (SEQ ID NO: 13)
5'-GTGCCCCATGATACGCCTCCGG-3'

AMDS2NcoMut (2721):
                                (SEQ ID NO: 14)
5'-GAGTCGTATTTCCAAGGCTCCTGACC-3'

AMDS1 NcoMut (3396):
                                (SEQ ID NO: 15)
5'-GGAGGCCATGAAGTGGACCAACGG-3'
```

A plasmid comprising all three expected sequence changes was then submitted to site-directed mutagenesis, using a QuickChange™ Site-Directed Mutagenesis Kit (Stratagene, La Jolla, Calif., USA), to eliminate the Nco I restriction site at the end of the AMG terminator at position 1643. The following primers (underlined nucleotide represents the changed base) were used for mutagenesis:

```
Upper Primer to mutagenize the AMG terminator
sequence:
                                (SEQ ID NO: 16)
5'-CACCGTGAAAGCCATGCTCTTTCCTTCGTGTAGAAGACCAGAC
AG-3'

Lower Primer to mutagenize the AMG terminator
sequence:
                                (SEQ ID NO: 17)
5'-CTGGTCTTCTACACGAAGGAAAGAGCATGGCTTTCACGGTGTC
TG-3'
```

Figure 7:
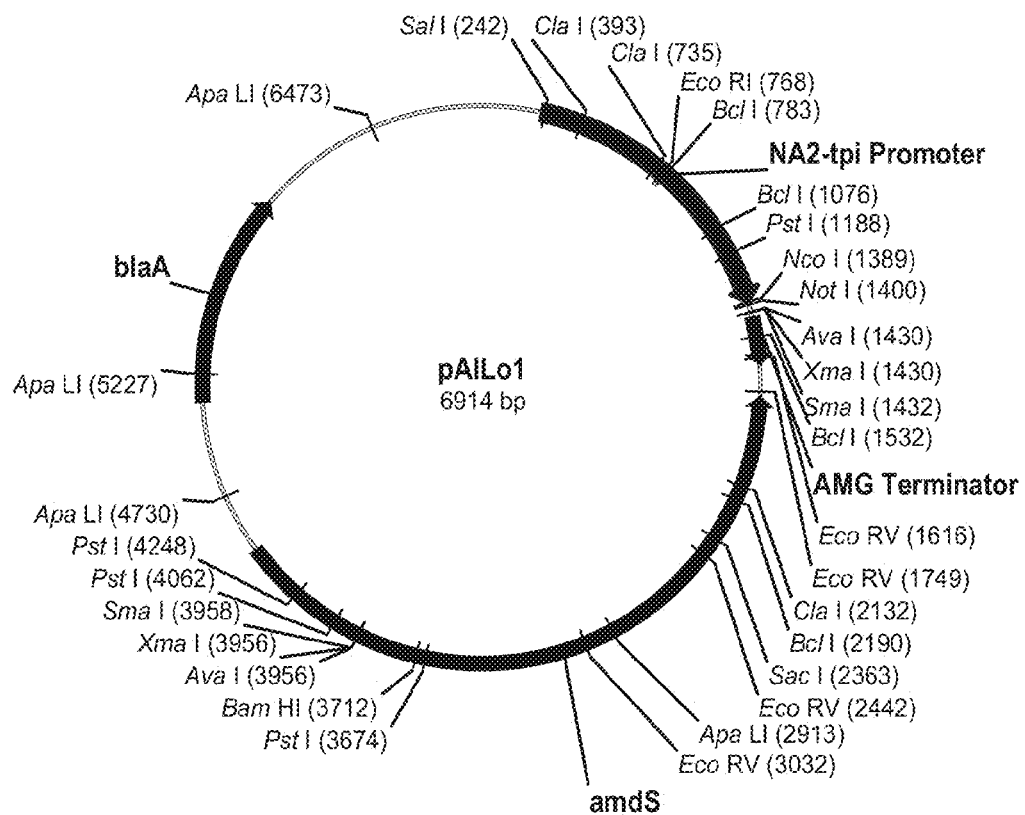
FIG. 7 shows a restriction map of pAILo1.

The last step in the modification of pBANe6 was the addition of a new Nco I restriction site at the beginning of the polylinker using a QuickChange™ Site-Directed Mutagenesis Kit and the following primers (underlined nucleotides represent the changed bases) to yield pAILo1 (FIG. 7).

```
Upper Primer to mutagenize the NA2-tpi promoter:
                                (SEQ ID NO: 18)
5'-CTATATACACAACTGGATTTACCATGGGCCCGCGGCCGCAGA
TC-3'

Lower Primer to mutagenize the NA2-tpi promoter:
                                (SEQ ID NO: 19)
5'-GATCTGCGGCCGCGGGCCCATGGTAAATCCAGTTGTGTATATA
G-3'
```

Figure 8:
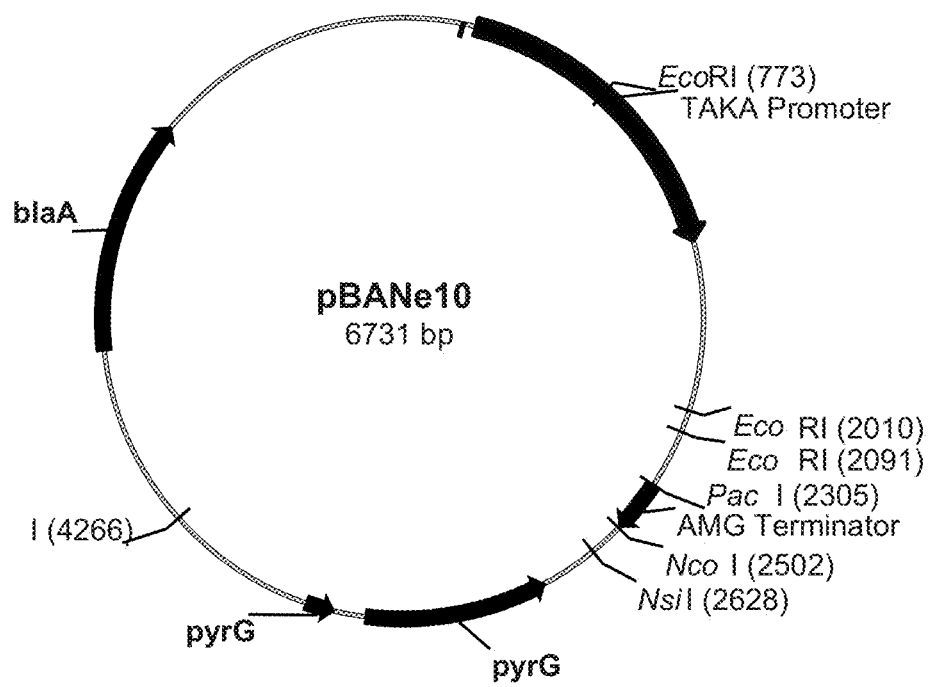
FIG. 8 shows a restriction map of pBANe10.
Figure 9:
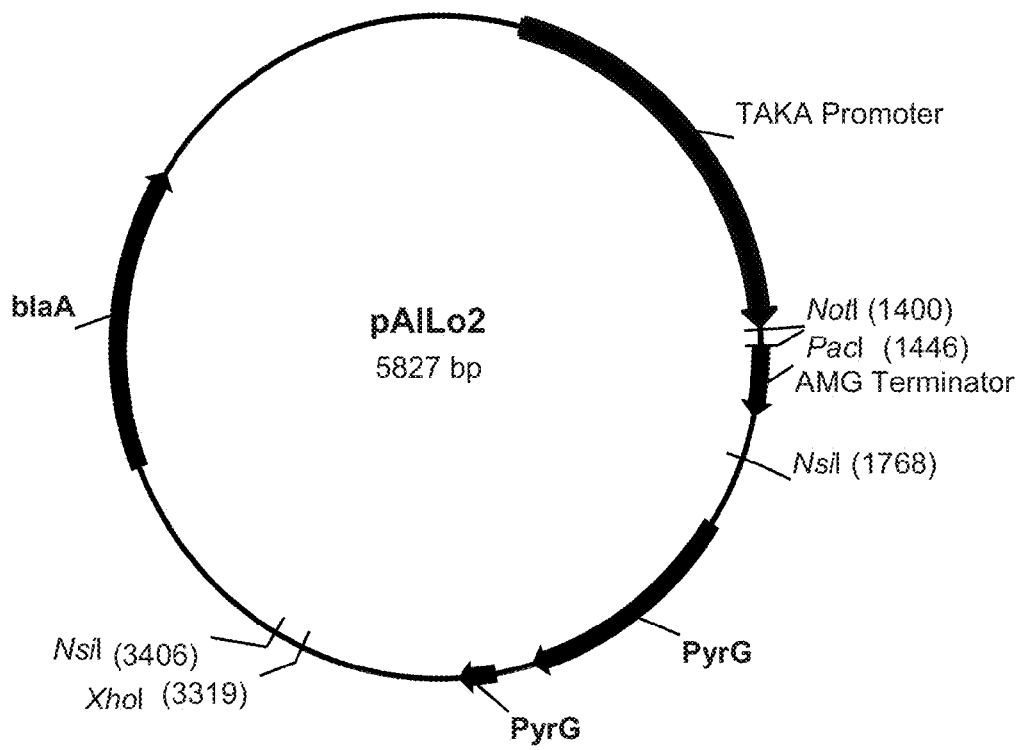
FIG. 9 shows a restriction map of pAILo2.

The amdS gene of pAILo1 was swapped with the *Aspergillus nidulans* pyrG gene. Plasmid pBANe10 (FIG. 8) was used as a source for the pyrG gene as a selection marker. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAILo1 and pBANe10 were digested with the restriction enzyme Nsi I and the products purified by agarose gel electrophoresis. The Nsi I fragment from pBANe10 containing the pyrG gene was ligated to the backbone of pAILo1 to replace the original Nsi I DNA fragment containing the amdS gene. Recombinant clones were analyzed by restriction enzyme digestion to determine that they had the correct insert and also its orientation. A clone with the pyrG gene transcribed in the counterclockwise direction was selected. The new plasmid was designated pAILo2 (FIG. 9).

Example 9

Construction of *Aspergillus oryzae* Expression Vectors for the *Thielavia terrestris* NRRL 8126 cel7c and cel7e Genes Two synthetic oligonucleotide primers shown below were designed to PCR amplify the *Thielavia terrestris* NRRL 8126 cel7c gene from the genomic clone. An InFusion Cloning Kit (BD Biosciences, Palo Alto, Calif., USA) was used to clone the fragment directly into the expression vector pAILo2 without the need for restriction digests and ligation.

```
Forward primer:
                                          (SEQ ID NO: 20)
5'-ACTGGATTACCATGGGCCAGAAGACGCTG-3'

Reverse primer:
                                          (SEQ ID NO: 21)
5'-AGTCACCTCTAGTTAGAGGCACTGGTAGTAC-3'
```

Bold letters represent coding sequence. The remaining sequence is homologous to the insertion sites of pAILo2.

Fifty picomoles of each of the primers above were used in a PCR reaction containing 100 ng of *Thielavia terrestris* genomic DNA (prepared as described in Example 2), 1× Pfx Amplification Buffer, 1.5 µl of 10 mM blend of dATP, dTTP, dGTP, and dCTP, 2.5 units of Platinum Pfx DNA Polymerase (Invitrogen, Carlsbad, Calif., USA), 1 µl of 50 mM $MgSO_4$ and 5 µl of 10× pCRX Enhancer Solution (Invitrogen, Carlsbad, Calif., USA) in a final volume of 50 µl. Amplification was performed in a Stratagene Robocycler® programmed for 1 cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where an approximately 3 kb product band was excised from the gel and purified using a QIAquick Gel Extraction Kit according to the manufacturer's instructions.

Figure 10:
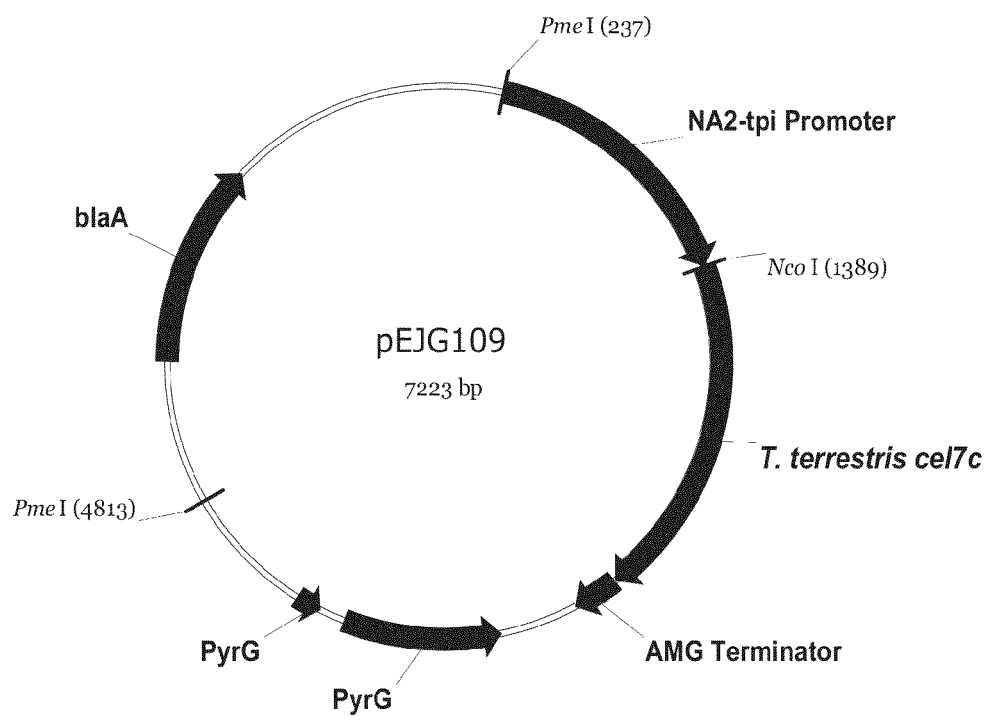
FIG. 10 shows a restriction map of pEJG109.

The fragment was then cloned into pAILo2 using an InFusion Cloning Kit. The vector was digested with Nco I and Pac I (using conditions specified by the manufacturer). The fragment was purified by 1% agarose gel electrophoresis using TAE buffer and a QIAquick Gel Purification Kit. The gene fragment and the digested vector were ligated together in a reaction resulting in the expression plasmid pEJG109 (FIG. 10) in which transcription of the cel7c gene was under the control of the NA2-tpi promoter. The ligation reaction (20 µl) was composed of 1× InFusion Buffer (BD Biosciences, Palo Alto, Calif., USA), 1×BSA (BD Biosciences, Palo Alto, Calif., USA), 1 µl of InFusion enzyme (diluted 1:10) (BD Biosciences, Palo Alto, Calif.), 100 ng of pAILo2 digested with Nco I and Pac I, and 100 ng of the *Thielavia terrestris* cel7c purified PCR product. The reaction was incubated at room temperature for 30 minutes. One µl of the reaction was used to transform *E. coli* XL10 Solopac Gold cells (Stratagene, La Jolla, Calif., USA). An *E. coli* transformant containing pEJG109 (cel7c gene) was detected by restriction enzyme digestion with Xho I and plasmid DNA was prepared using a QIAGEN BioRobot 9600.

An expression construct for the *Thielavia terrestris* cel7e gene was generated in the same manner as described above using the following primers.

```
In-Fusion Forward primer:
                                          (SEQ ID NO: 22)
5'-ACTGGATTACCATGGCGCCCAAGTCTACAGTTCTGG-3'

In-Fusion Reverse primer:
                                          (SEQ ID NO: 23)
5'-TCACCTCTAGTTAATTAACTAGTGGCTGCACTCGCTCT-3'
```

Bold letters represent coding sequence. The remaining sequence is homologous to the insertion sites of pAILo2.

Figure 11:
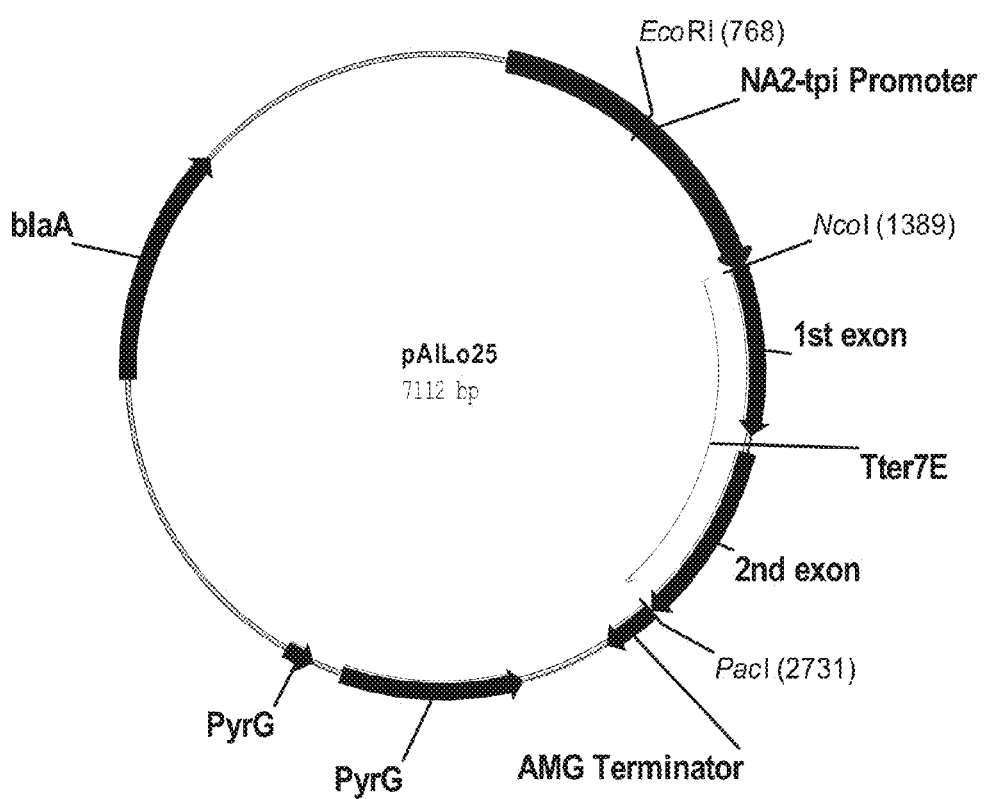
FIG. 11 shows a restriction map of pAILo25.

A 1.3 kb PCR reaction product was isolated on a 0.8% GTG-agarose gel (Cambrex Bioproducts One Meadowlands Plaza East Rutherford, N.J. 07073) using TAE buffer and 0.1 µg of ethidium bromide per ml. The DNA band was visualized with the aid of a Dark Reader™ (Clare Chemical Research, Dolores, Colo.) to avoid UV-induced mutations. The 1.3 kb DNA band was excised with a disposable razor blade and purified with an Ultrafree-DA spin cup (Millipore, Billerica, Mass.) according to the manufacturer's instructions. Cloning of the purified PCR fragment into the linearized and purified pAILo2 vector was performed as described above with an In-Fusion Cloning Kit (BD Biosciences, Palo Alto, Calif.) to generate pAILo25 (FIG. 11).

*E. coli* transformants containing pAILo25 were identified by restriction enzyme digestion analysis and plasmid DNA was prepared using a QIAGEN BioRobot 9600.

Example 10

Expression of *Thielavia terrestris* NRRL 8126 Genes Encoding CEL7C and CEL7E Endoglucanases in *Aspergillus oryzae* JaL250

*Aspergillus oryzae* JaL250 protoplasts were prepared according to the method of Christensen et al., 1988, *Bio/Technology* 6: 1419-1422. Five µg of pEJG109 (as well as pAILo2 as a vector control) was used to transform *Aspergillus oryzae* JaL250 (WO 99/61651).

The transformation of *Aspergillus oryzae* JaL250 with pEJG109 (cel7c gene) yielded about 100 transformants. Ten transformants were isolated to individual PDA plates.

Confluent PDA plates of 5 transformants were washed with 5 ml of 0.01% Tween 80 and inoculated separately into 25 ml of MDU2BP medium in 125 ml glass shake flasks and incubated at 34° C., 200 rpm. Five days after incubation, a 5 µl sample of supernatant from each culture was analyzed using 8-16% Tris-Glycine SDS-PAGE gels (Invitrogen, Carlsbad, Calif., USA) according to the manufacturer's instructions. SDS-PAGE profiles of the culture supernatants showed that 5 of the 5 transformants had a new major band of approximately 74 kDa.

A confluent plate of transformant 10 (grown on PDA) was washed with 10 ml of 0.01% Tween 20 and inoculated into a 2 liter Fernbach containing 500 ml of MDU2BP medium to generate broth for characterization of the enzyme. The flask was harvested on day 5 and filtered using a 0.22 µm GP Express plus Membrane (Millipore, Bedford, Mass., USA).

Plasmid pAILo25 (cel7e gene) was expressed in *Aspergillus oryzae* JaL250 using the same protocol described above. Transformation of *Aspergillus oryzae* Jal250 yielded about 35 transformants. Eight transformants were isolated to individual PDA plates and incubated for five days at 34° C. SDS-PAGE profiles of the culture supernatants showed that eight out of eight pAILo25 transformants had a new diffuse protein band of approximately 55 kDa. Transformant #4 was selected for further studies and designated *Aspergillus oryzae* JaL250 pAILo25.

Example 11

Cloning and Expression of the *Cladorrhinum foecundissimum* ATCC 62373 cDNA Encoding a CEL7A Endoglucanase

*Cladorrhinum foecundissimum* ATCC 62373 was cultivated in 200 ml of PD medium with cellulose at 30° C. for five days at 200 rpm. Mycelia from the shake flask culture were harvested by filtering the contents through a funnel lined with Miracloth™ The mycelia were then sandwiched between two Miracloth™ pieces and blotted dry with absorbent paper towels. The mycelial mass was then transferred to Falcon® 1059 plastic centrifuge tubes (BD Biosciences, Palo Alto, Calif., USA) and frozen in liquid nitrogen. Frozen mycelia were stored in a –80° C. freezer until use.

The extraction of total RNA was performed with guanidinium thiocyanate followed by ultracentrifugation through a 5.7 M CsCl cushion, and isolation of poly(A)+RNA was carried out by oligo(dT)-cellulose affinity chromatography, using the procedures described in WO 94/14953.

Double-stranded cDNA was synthesized from 5 µg of poly (A)+RNA by the RNase H method (Gubler and Hoffman, 1983, *Gene* 25: 263-269, Sambrook et al., 1989, *Molecular cloning: A laboratory manual*, Cold Spring Harbor lab., Cold Spring Harbor, N.Y.). The poly(A)$^+$ RNA (5 µg in 5 µl of DEPC (0.1% diethylpyrocarbonate)-treated water) was heated at 70° C. for 8 minutes in a pre-siliconized, RNase-free Eppendorf® tube, quenched on ice, and combined in a final volume of 50 µl with reverse transcriptase buffer composed of 50 mM Tris-HCl, pH 8.3, 75 mM KCl, 3 mM MgCl$_2$, 10 mM dithiothreitol (DTT) (Bethesda Research Laboratories, Bethesda, Md., USA), 1 mM of dATP, dGTP and dTTP, and 0.5 mM 5-methyl-dCTP (Pharmacia, Uppsala, Sweden), 40 units of human placental ribonuclease inhibitor (RNasin, Promega, Madison, Wis., USA), 1.45 µg of oligo(dT)$_{18}$-Not I primer (Pharmacia, Uppsala, Sweden), and 1000 units of SuperScript® II RNase H reverse transcriptase (Bethesda Research Laboratories, Bethesda, Md., USA). First-strand cDNA was synthesized by incubating the reaction mixture at 45° C. for 1 hour. After synthesis, the mRNA:cDNA hybrid mixture was gel filtrated through a MicroSpin S-400 HR spin column (Pharmacia, Uppsala, Sweden) according to the manufacturer's instructions.

After gel filtration, the hybrids were diluted in 250 µl of second strand buffer (20 mM Tris-HCl, pH 7.4, 90 mM KCl, 4.6 mM MgCl$_2$, 10 mM (NH$_4$)$_2$SO$_4$, 0.16 mM NAD) containing 200 µM of each dNTP, 60 units of *E. coli* DNA polymerase I (Pharmacia, Uppsala, Sweden), 5.25 units of RNase H (Promega, Madison, Wis., USA), and 15 units of *E. coli* DNA ligase (Boehringer Mannheim, Manheim, Germany). Second strand cDNA synthesis was performed by incubating the reaction tube at 16° C. for 2 hours and an additional 15 minutes at 25° C. The reaction was stopped by addition of EDTA to a final concentration of 20 mM followed by phenol and chloroform extractions.

The double-stranded cDNA was precipitated at –20° C. for 12 hours by addition of 2 volumes of 96% ethanol and 0.2 volume of 10 M ammonium acetate, recovered by centrifugation at 13,000×g, washed in 70% ethanol, dried, and resuspended in 30 µl of Mung bean nuclease buffer (30 mM sodium acetate pH 4.6, 300 mM NaCl, 1 mM ZnSO$_4$, 0.35 mM DTT, 2% glycerol) containing 25 units of Mung bean nuclease (Pharmacia, Uppsala, Sweden). The single-stranded hair-pin DNA was clipped by incubating the reaction at 30° C. for 30 minutes, followed by addition of 70 µl of 10 mM Tris-HCl-1 mM EDTA pH 7.5, phenol extraction, and precipitation with 2 volumes of 96% ethanol and 0.1 volume of 3 M sodium acetate pH 5.2 on ice for 30 minutes.

The double-stranded cDNAs were recovered by centrifugation at 13,000×g and blunt-ended in 30 µl of T4 DNA polymerase buffer (20 mM Tris-acetate, pH 7.9, 10 mM magnesium acetate, 50 mM potassium acetate, 1 mM DTT) containing 0.5 mM of each dNTP and 5 units of T4 DNA polymerase (New England Biolabs, Ipswich, Mass., USA) by incubating the reaction mixture at 16° C. for 1 hour. The reaction was stopped by addition of EDTA to a final concentration of 20 mM, followed by phenol and chloroform extractions, and precipitation for 12 hours at –20° C. by adding 2 volumes of 96% ethanol and 0.1 volume of 3 M sodium acetate pH 5.2.

After the fill-in reaction the cDNAs were recovered by centrifugation at 13,000×g, washed in 70% ethanol, and dried. The cDNA pellet was resuspended in 25 µl of ligation buffer (30 mM Tris-HCl, pH 7.8, 10 mM MgCl$_2$, 10 mM DTT, 0.5 mM ATP) containing 2.5 µg of non-palindromic Bst XI adaptors (Invitrogen, Carlsbad, Calif., USA), shown below, and 30 units of T4 ligase (Promega, Madison, Wis., USA), and then incubated at 16° C. for 12 hours. The reaction was stopped by heating at 65° C. for 20 minutes and then cooled on ice for 5 minutes.

```
                    (SEQ ID NO: 24)
       5'-CTTTCCAGCACA-3'

3'-GAAAGGTC-5'
```

The adapted cDNA was digested with Not I, followed by incubation for 2.5 hours at 37° C. The reaction was stopped by heating at 65° C. for 10 minutes. The cDNAs were size-fractionated by gel electrophoresis on a 0.8% SeaPlaque® GTG low melting temperature agarose gel (Cambrex Corporation, East Rutherford, N.J., USA) in 44 mM Tris Base, 44 mM boric acid, 0.5 mM EDTA (TBE) buffer to separate unligated adaptors and small cDNAs. The cDNA was size-selected with a cut-off at 0.7 kb and rescued from the gel by use of beta-agarase (New England Biolabs, Ipswich, Mass., USA Biolabs) according to the manufacturer's instructions and precipitated for 12 hours at –20° C. by adding two volumes of 96% ethanol and 0.1 volume of 3 M sodium acetate pH 5.2.

The directional, size-selected cDNA was recovered by centrifugation at 13,000×g, washed in 70% ethanol, dried, and then resuspended in 30 µl of 10 mM Tris-HCl-1 mM EDTA pH 7.5. The cDNAs were desalted by gel filtration through a MicroSpin S-300 HR spin column according to the manufacturer's instructions. Three test ligations were carried out in 10 µl of ligation buffer (30 mM Tris-HCl, pH 7.8, 10 mM MgCl$_2$, 10 mM DTT, 0.5 mM ATP) containing 5 µl of double-stranded cDNA (reaction tubes #1 and #2), 15 units of T4 ligase, and 30 ng (tube #1), 40 ng (tube #2), and 40 ng (tube #3, the vector background control) of Bst XI-Not I cleaved pYES2.0 vector (Invitrogen, Carlsbad, Calif., USA). The ligation reactions were performed by incubation at 16° C. for 12 hours, then heating at 70° C. for 20 minutes, and finally adding 10 µl of water to each tube. One µl of each ligation mixture was electroporated into 40 µl of electrocompetent *E.* coli DH10B cells (Bethesda Research Laboratories, Bethesda, Md., USA) as described by Sambrook et al., 1989, supra.

The *Cladorrhinum foecundissimum* ATCC 62373 cDNA library was established as pools in *E. coli* DH10B. Each pool was made by spreading transformed *E. coli* on LB plates supplemented with 100 μg of ampicillin per ml, yielding 15,000-30,000 colonies/plate after incubation at 37° C. for 24 hours. Twenty ml of LB medium supplemented with 100 μg of ampicillin per ml was added to the plate and the cells were suspended therein. The cell suspension was shaken at 100 rpm in a 50 ml tube for 1 hour at 37° C.

The resulting *Cladorrhinum foecundissimum* ATCC 62373 cDNA library consisted of approximately $10^6$ individual clones, with a vector background of 1%. Plasmid DNA from some of the library pools was isolated using a Plasmid Midi Kit (QIAGEN Inc., Valencia, Calif., USA), according to the manufacturer's instructions, and stored at −20° C.

One ml aliquots of purified plasmid DNA (100 ng/ml) from some of the library pools (Example 1) were transformed into *Saccharomyces cerevisiae* W3124 by electroporation (Becker and Guarante, 1991, *Methods Enzymol.* 194: 182-187) and the transformants were plated on SC agar containing 2% glucose and incubated at 30° C. In total, 50-100 plates containing 250-400 yeast colonies were obtained from each pool.

After 3-5 days of incubation, the SC agar plates were replica plated onto a set of 0.1% AZCL HE cellulose SC URA agar plates with galactose. The plates were incubated for 2-4 days at 30° C. and endoglucanase positive colonies were identified as colonies surrounded by a blue halo.

Endoglucanase-expressing yeast colonies were inoculated into 20 ml of YPD medium in 50 ml glass test tubes. The tubes were shaken at 200 rpm for 2 days at 30° C. The cells were harvested by centrifugation for 10 minutes at 3000 rpm in a Heraeus Megafuge 1.0R centrifuge with a 75002252 rotor (Hanau, Germany).

DNA was isolated according to WO 94/14953 and dissolved in 50 μl of deionized water. The DNA was transformed into *E. coli* DH10B cells by standard procedures according to Sambrook et al., 1989, supra. One *E. coli* transformant was subsequently shown to contain the *Cladorrhinum foecundissimum* ATCC 62373 cel7a gene, and the plasmid in this strain was designated pCIC521.

Example 12

Expression of *Cladorrhinum foecundissimum* ATCC 62373 cel7a Gene in *Aspergillus oryzae*

The *Cladorrhinum foecundissiumum* ATCC 62373 cel7a gene was excised from pC10521 using Bam HI and Xba I, and ligated into the *Aspergillus* expression vector pHD464 (Dalboge and Heldt-Hansen, 1994, *Molecular and General Genetics* 243: 253-260) using standard methods (Sambrook et al., 1989, supra). The resulting plasmid was designated pA2CIC521.

Protoplasts of *Aspergillus oryzae* HowB104 were prepared as described in WO 95/02043. One hundred microliters of protoplast suspension was mixed with 5-25 μg of the *Aspergillus* expression vector pA2CIC521 in 10 μl of STC composed of 1.2 M sorbitol, 10 mM Tris-HCl, pH 7.5, 10 mM $CaCl_2$) and further mixed with 5-25 μg of p3SR2, an *Aspergillus nidulans* amdS gene carrying plasmid (Christensen et al., 1988, *Bio/Technology* 6: 1419-1422). The mixture was left at room temperature for 25 minutes. Two hundred microliters of 60% PEG 4000 (BDH, Poole, England) (polyethylene glycol, molecular weight 4,000), 10 mM $CaCl_2$, and 10 mM Tris-HCl pH 7.5 was added and gently mixed and finally 0.85 ml of the same solution was added and gently mixed. The mixture was left at room temperature for 25 minutes, centrifuged at 2,500×g for 15 minutes, and the pellet was resuspended in 2 ml of 1.2 M sorbitol. This sedimentation process was repeated, and the protoplasts were spread on COVE plates. After incubation for 4-7 days at 37° C. spores were picked and spread in order to isolate single colonies. This procedure was repeated and spores of a single colony after the second reisolation were stored.

Each of the transformants was inoculated in 10 ml of YPM medium. After 2-5 days of incubation at 30° C., 200 rpm, the supernatant was removed. Endoglucanase activity was identified by applying 20 μl of culture broth to 4 mm diameter holes punched out in a 0.1% AZCL HE cellulose SC-agar plate and incubation overnight at 30° C. The presence of endoglucanase activity produced a blue halo around a colony. Several transformant broths had endoglucanase activity that was significantly greater than broth from an untransformed *Aspergillus oryzae* background control, which demonstrated efficient expression of the CEL7A endoglucanase from *Cladorrhinum foecundissimum* ATCC 62373 in *Aspergillus oryzae*. One *Aspergillus oryzae* transformant was designated A2.110521 4/3.

Example 13

*Aspergillus oryzae* A2.110521 4/3 Genomic DNA Extraction

*Aspergillus oryzae* strain A2.110521 4/3 expressing the CEL7A protein of *Cladorrhinum foecundissimum* was grown in M400 medium, in 300 ml culture volume, using baffled shake flasks for 7 days, 34° C., at 200 rpm. Biomass was frozen in liquid nitrogen and ground to a powder with a mortar and pestle. The powder was suspended in 15 ml of 0.1 M CAPS-NaOH pH 11.0, 1 mM EDTA, 0.5% lithium dodecyl sulfate and incubated for 60 minutes at 60° C. with periodic mixing by inversion. An equal volume of neutralized phenol was added and the tube was shaken gently for 1 hr at 37° C. Five ml of chloroform was added and the tube was agitated vigorously for 1 minute. After centrifugation at 1300×g for 10 minutes, the top aqueous phase was re-extracted with an equal volume of phenol:chloroform (1:1) by agitation for 5 minutes. Centrifugation was repeated and the aqueous phase was brought to 2.5 M ammonium acetate and stored at −20° C. for 20 minutes. After centrifugation at 17,000×g for 20 minutes at 4° C., the supernatant nucleic acids in the supernatant were precipitated by adding 0.7 volumes of isopropanol. After centrifugation at 17,000×g for 10 minutes, the supernatant was decanted and the pellet was rinsed with 70% ethanol and air dried. The pellet was dissolved in 950 μl of deionized water followed by addition of 50 μl of Promega Cell Resuspension Solution (Promega Corporation, Madison Wis., USA) and incubation for 5 minutes at room temperature. Ammonium acetate was added to 1.0 M and nucleic acids precipitated by addition of 2 volumes of ethanol. After centrifugation at 13,000×g for 10 minutes, the pellet was dissolved in 300 μl of 1 mM Tris-HCl, 0.1 mM EDTA, pH 8.0, and stored at −20° C.

Example 14

PCR Amplification of the *Cladorrhinum foecundissimum* cel7a cDNA from genomic DNA of *Aspergillus oryzae* expression strain A2.110521 4/3

For purposes of sequencing and clone deposit, the cel7a cDNA was amplified from *Aspergillus oryzae* strain A2.110521 4/3 genomic DNA. Two synthetic oligonucleotide primers homologous to pHD464 expression vector were designed to PCR amplify the cel7a gene from *Aspergillus oryzae* strain A2.110521 4/3 genomic DNA.

```
Forward primer:
            (SEQ ID NO: 25)
5'-CCACACTTCTCTTCCTTCCTC-3'

Reverse primer:
            (SEQ ID NO: 26)
5'-CCCCATCCTTTAACTATAGCG-3'
```

Seventeen picomoles of each of the primers above were used in a PCR reaction containing 100 ng of *Aspergillus oryzae* A2.110521 4/3 genomic DNA (prepared as described in Example 13), 1× Pfx Amplification Buffer (Invitrogen, Carlsbad Calif., USA), 1.7 µl of a 10 mM blend of dATP, dTTP, dGTP, and dCTP, 2.5 units of Platinum Pfx DNA Polymerase, and 1 µl of 50 mM MgSO$_4$ in a final volume of 50 µl. Amplification was performed in a Stratagene Robocycler® programmed for 1 cycle at 96° C. for 3 minutes and 72° C. for 3 minutes (during which DNA polymerase was added); and 35 cycles each at 94° C. for 50 seconds, 5° C. for 50 seconds, and 68° C. for 2 minutes, followed by a final extension at 68° C. for 7 minutes.

The reaction products were isolated on a 1.0% agarose gel using TAE buffer where an approximately 1.7 kb product band was excised from the gel and purified using a QIAEX® II Gel Extraction Kit according to the manufacturer's instructions.

Figure 12:
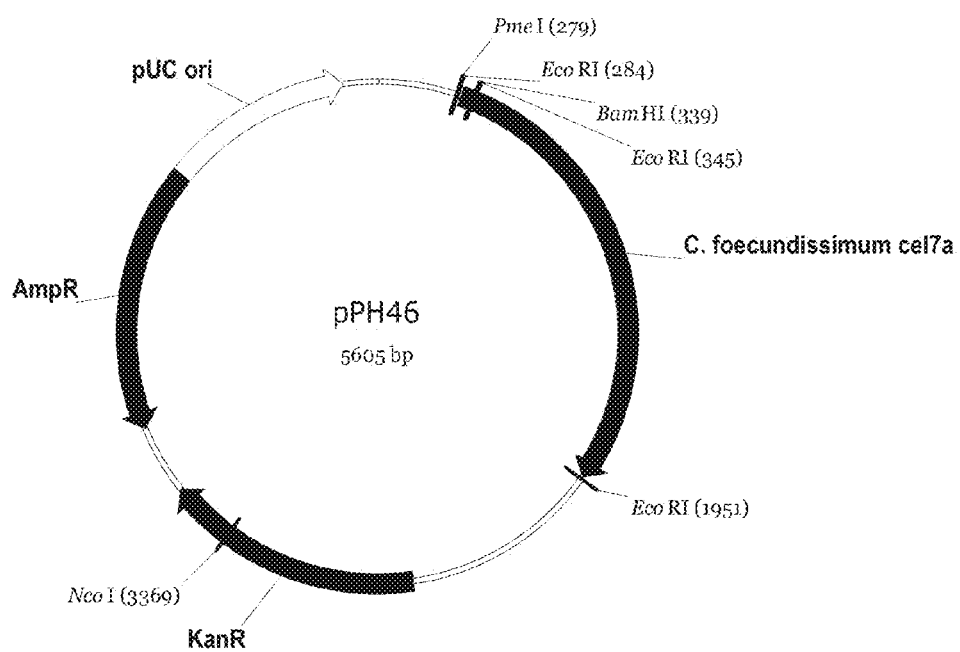
FIG. 12 shows a restriction map of pPH46.

The 1.7 kb fragment was cloned into the pCR-Blunt II-TOPO vector using a Zero Blunt TOPO PCR Cloning Kit and transformed into *E. coli* TOP10 cells according to the manufacturer's instructions (Invitrogen, Carlsbad Calif., USA). Plasmid DNA from several transformants was prepared using a QIAGEN BioRobot 9600. Plasmid from two transformants was sequenced and found to be identical and to contain the cel7a cDNA. One plasmid was designated pPH46 (FIG. 12).

*E. coli* PaHa46 containing plasmid pPH46 (FIG. 12) was deposited with the Agricultural Research Service Patent Culture Collection, Northern Regional Research Center, 1815 University Street, Peoria, Ill., 61604, as NRRL B-30897, with a deposit date of Feb. 23, 2006.

Example 15

Characterization of the *Cladorrhinum foecundissimum* ATCC 62373 cDNA Sequence Encoding the CEL7A Endoglucanase DNA sequencing of the *Cladorrhinum foecundissimum* ATCC 62373 cel7a cDNA in plasmid pPH46 was performed with an Applied Biosystems Model 3700 Automated DNA Sequencer using version 3.1 BigDye™ terminator chemistry and dGTP chemistry and primer walking strategy. Nucleotide sequence data were scrutinized for quality and all sequences were compared to each other with assistance of PHRED/PHRAP software (University of Washington, Seattle, Wash., USA).

Figure 13A:
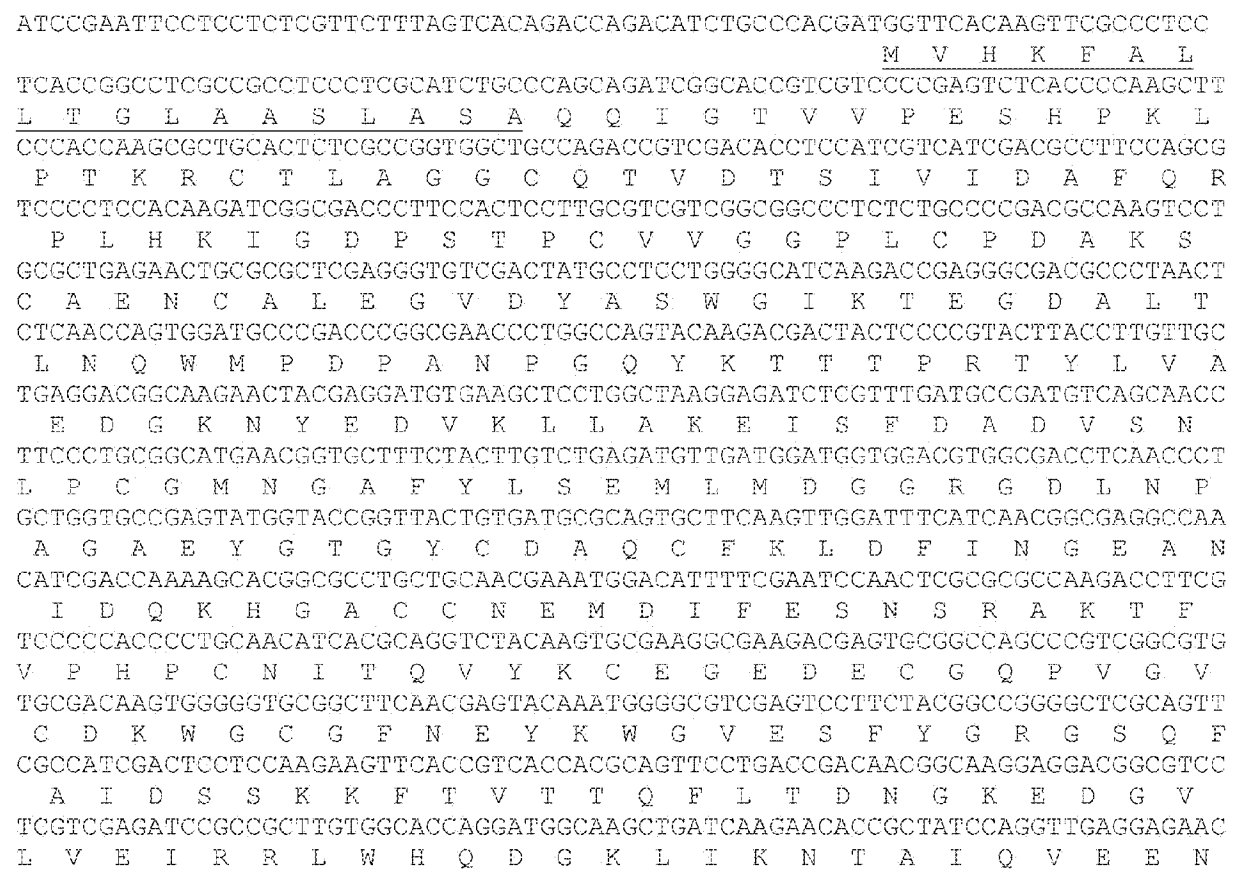

The nucleotide sequence (SEQ ID NO: 5) and deduced amino acid sequence (SEQ ID NO: 6) of the *Cladorrhinum foecundissimum* cel7a cDNA are shown in FIGS. 13A and 13B. The coding sequence is 1323 bp including the stop codon. The encoded predicted protein is 440 amino acids. The % G+C of the coding sequence of the gene is 59.2% and the mature polypeptide coding sequence is 59.0%. Using the SignalP program (Nielsen et al., 1997, supra), a signal peptide of 18 residues was predicted. The predicted mature protein contains 422 amino acids with a molecular mass of 45.7 kDa. Analysis of the deduced amino acid sequence of the cel7a gene with the InterProScan program (Zdobnov and Apweiler, 2001, supra) showed that the CEL7A polypeptide contained the domain signature of glycoside hydrolase Family 7 (InterPro accession number IPR001722) from approximately amino acids 2 to 405 of the mature polypeptide.

A comparative pairwise global alignment of amino acid sequences was determined using the Needleman-Wunsch algorithm (Needleman and Wunsch, 1970, supra) as implemented in the Needle program of EMBOSS with gap open penalty of 10, gap extension penalty of 0.5, and the EBLOSUM62 matrix. The alignment showed that the deduced amino acid sequence of the *Cladorrhinum foecundissimum* cDNA encoding the CEL7A mature polypeptide having endoglucanase activity shares 79% and 55% identity (excluding gaps) to the deduced amino acid sequences of two glycosyl hydrolase Family 7 proteins from *Neurospora crassa* (accession number Q7RXC7) and *Talaromyces emersonii* (accession number CAC94521.1). It also shares 64% and 57% identity with the *Thielavia terrestris* CEL7E and CEL7C mature polypeptides, respectively.

Broth containing the *Cladorrhinum foecundissimum* Family 7A was separated by 10-20% Tris-Glycine SDS-PAGE as described in Example 1. A gel band of approximately 50 kDa was subjected to in-gel digestion and de novo sequenced using tandem mass spectrometry as described in Example 1.

A partial sequence from a doubly charged tryptic peptide ion of 701.85 m/z sequence was determined to be Gly-Thr-Val-Val-Pro-Glu-Ser-His-Pro-Lys, which corresponds to the sequence GTVVPESHPK (amino acids 22 to 31 of SEQ ID NO: 6). A partial sequence from a second doubly charged tryptic peptide ion of 739.35 was determined to be Gly-Glu-Ala-Asn-[Ile or Leu]-Asp-[Gln or Lys]-Lys wherein Xaa is any amino acid, which corresponds to the sequence GEANIDQK (amino acids 202 to 209 of SEQ ID NO: 6). A third doubly charged tryptic peptide ion of 919.83 was determined to be [CAM(carboxyamidomethylcysteine) or Phe]-Glu-Gly-Glu-Asp-Glu-[Cam or Phe]-Gly-[Gln or Lys]-Pro-Val-Gly-Val-[Cam or Phe]-Asp-Lys, which corresponds to the sequence CEGEDECGQPVGVCDK (amino acids 242 to 257 of SEQ ID NO: 6). A fourth doubly charged tryptic peptide ion of 970.45 a partial sequence was determined to be Pro-Ser-Thr-Pro-Cam-Val-Val-Gly-Gly-Pro-[Ile or Leu]-Cam-Pro-Asp-Ala-Lys, which corresponds to the sequence PSTPCVVGGPLCPDAK (amino acids 65 to 80 of SEQ ID NO: 6).

Example 16

Preparation of Recombinant Endoglucanases from *Cladorrhinum foecundissimum* ATCC 62373 and *Thielavia terrestris* NRRL 8126

The *Cladorrhinum foecundissimum* CEL7 endoglucanase produced recombinantly in *Aspergillus oryzae*, as described in Example 12, were purified to homogeneity using a protocol essentially as described by Otzen et al., 1999, *Protein Sci.* 8: 1878-87.

The *Thielavia terrestris* CEL7C and *Thielavia terrestris* CEL7E endoglucanases produced recombinantly in *Aspergillus oryzae*, as described in Example 10, were tested in the form of culture broth from expression host *Aspergillus oryzae*. The broth was concentrated and exchanged to 50 mM sodium acetate buffer pH 5.0 using Centricon Plus-20 centrifugal filter with Biomax-5 polyethersulfone membrane (5000 NMWL) (Millipore, Bedford, Mass., USA).

Protein concentration in the enzyme preparations was determined using the Bicinchoninic Acid (BCA) microplate assay according to the manufacturer's instructions for a BCA Protein Assay Reagent Kit (Pierce Chemical Co., Rockford, Ill., USA).

Enzyme dilutions were prepared fresh before each experiment from stock enzyme solutions, which were stored at −20° C.

Example 17

Preparation of Substrates

Pretreated corn stover (PCS) was prepared by the U.S. Department of Energy National Renewable Energy Laboratory (NREL, Golden, Colo., USA) using dilute sulfuric acid. The following conditions were used for the pretreatment: 1.4 wt % sulfuric acid at 165° C. and 10 psi for 8 minutes. Compositional analysis was performed at NREL. Cellulose and hemicellulose were determined by a two-stage sulfuric acid hydrolysis with subsequent analysis of sugars by high performance liquid chromatography (HPLC) using NREL Standard Analytical Procedure #002. Lignin was determined gravimetrically after hydrolyzing the cellulose and hemicellulose fractions with sulfuric acid (NREL Standard Analytical Procedure #003). Water-insoluble solids in the pretreated corn stover (PCS) were determined to be 56.5% cellulose, 4.6% hemicellulose, and 28.4% lignin.

The PCS was washed with large volume of deionized water on a Kimax funnel with a glass filter of coarse porosity (Fisher Scientific, Pittsburgh, Pa., USA). Water-washed PCS was milled in a coffee grinder and additionally washed with deionized water on a 22 μm Millipore Filter with a 6P Express Membrane (Millipore, Bedford, Mass., USA). Dry weight of the milled PCS was 32.4%.

A 10 mg/ml stock suspension of phosphoric acid-swollen cellulose (PASO) in deionized water was prepared using the following procedure. One hundred and fifty ml of ice-cold 85% o-phosphoric acid was added to 5 g of Avicel PH101 (FMC Corp., Philadelphia, Pa., USA) moistened with water. The suspension was slowly stirred in an ice bath for one hour, and 100 ml of ice-cold acetone was added to the suspension at constant stirring. The slurry was transferred to a Kimax funnel with a glass filter of coarse porosity, washed three times with 100 ml of ice-cold acetone, and drained as completely as possible after each wash. Finally, the slurry was washed twice with 500 ml of water, and again drained as completely as possible after each wash. The PASO was mixed with water to a total volume of 500 ml. Sodium azide was added to a final concentration of 0.02% to prevent microbial growth. The slurry was homogenized using a blender and stored at 4° C. for up to one month.

Carboxymethylcellulose (CMC, sodium salt, type 7L2) with an average degree of substitution (DS) of 0.7 was obtained from Aqualon Division of Hercules Inc., Wilmington, Del., USA. A 6.25 mg/ml solution of CMC in 50 mM sodium acetate pH 5.0 was prepared by slowly adding CMC to the vigorously agitated buffer. The slurry was heated to approximately 60° C. under continuous stirring until the CMC was completely dissolved.

p-Nitrophenyl-beta-D-cellobioside (PNPC) and p-nitrophenyl-beta-D-lactoside (PNPL) were obtained from Sigma, St. Louis, Mo., USA.

Bacterial cellulose (BC) was prepared from Nata de Coco, a food-grade commercial cellulose (Fujicco Co., Kobe, Japan), as described in Boisset et al., 1999, *Biochemical Journal*, 340: 829-835. A 1 mg/ml suspension of bacterial cellulose in deionized water with 0.01% (w/v) sodium azide was stored at 4° C.

Avicel PH101 was obtained from FMC Corporation, Philadelphia, Pa., USA.

Xylan from birchwood was obtained from Sigma, St. Louis, Mo. Xyloglucan from Tamarind seed (amyloid, lot 00401), wheat arabinoxylan (medium viscosity, 27 cSt, lot 90601), 1,4-beta-D-mannan (borohydride reduced, Man: Gal=97:3, degree of polymerization DP~15, lot 90302), and carob galactomannan (low viscosity, borohydride reduced, lot 90301) were obtained from Megazyme, Bray, Ireland.

Example 18 p-Hydroxybenzoic Acid Hydrazide Assay for Determination of Reducing Sugars

Reducing sugars (RS) were determined by a p-hydroxybenzoic acid hydrazide (PHBAH) assay (Lever, 1972, Anal. Biochem. 47, 273-279), which was adapted to a 96-well microplate format.

A 90-μl aliquot of the diluted sample was placed into each well of a 96-well conical-bottomed microplate (Costar, clear polycarbonate, Corning Inc., Acton, Mass.). The assay was initiated by adding 60 μl of 1.25% PHBAH in 2% sodium hydroxide to each well. The uncovered plate was heated on a custom-made heating block for 10 minutes at 95° C. Following heating, the microplate was cooled to room temperature, and 35 μl of deionized water was added to each well. A 100 μl aliquot was removed from each well and transferred to a flat-bottomed 96-well plate (Costar, medium binding polystyrene, Corning Inc., Acton, Mass.). The absorbance at 410 nm ($A_{410}$) was measured using a SpectraMAX Microplate Reader (Molecular Devices, Sunnyvale, Calif.). The $A_{410}$ value was translated into glucose equivalents using a standard curve.

The standard curve was obtained with six glucose standards (0.005, 0.010, 0.025, 0.050, 0.075, and 0.100 mg/ml), which were treated similarly to the samples. Glucose standards were prepared by diluting 10 mg/ml stock glucose solution with deionized water.

For all substrates except for xylan and arabinoxylan, the degree of conversion (%) was calculated using the following equation:

$$\text{Conversion}_{(\%)} = RS_{(mg/ml)} \times 100 \times 162/(\text{Initial substrate concentration}_{(mg/ml)} \times 180) = RS_{(mg/ml)} \times 100/(\text{Initial substrate concentration}_{(mg/ml)} \times 1.111)$$

For xylan and arabinoxylan, percent of substrate hydrolyzed to RS was calculated using the following equation:

$$\text{Conversion}_{(\%)} = RS_{(mg/ml)} \times 100 \times 132/(\text{Initial substrate concentration}_{(mg/ml)} \times 150) = RS_{(mg/ml)} \times 100/(\text{Initial substrate concentration}_{(mg/ml)} \times 1.136)$$

In these equations, RS is the concentration of reducing sugars in solution measured in glucose equivalents (mg/ml), and the factors 1.111 and 1.136 reflect the weight gain in converting corresponding polysaccharides to hexose (MW 180) or pentose (MW 150) sugars.

Example 19

Relative Activity of *Cladorrhinum foecundissimum* ATCC 62373 CEL7A Endoglucanase on Various Substrates Relative activity of *Cladorrhinum foecundissimum* ATCC 62373 CEL7A endoglucanase towards four substrates is shown in Table 1. The relative activity is shown as a percentage of the activity of *Cladorrhinum foecundissimum* CEL7A endoglucanase on carboxymethylcellulose (CMC). The activity was determined by measuring the initial rate of hydrolysis in the range of linear increase of product concentration over time. *Cladorrhinum foecundissimum* CEL7A endoglucanase was diluted so as to give a linear relationship between enzyme concentration and activity measured.

Activity of *Cladorrhinum foecundissimum* CEL7A endoglucanase towards the soluble sodium salt of carboxymethylcellulose (CMC) was determined by measuring the concentration of reducing sugars (RS) produced from CMC (5 mg/ml) after 30 minutes of hydrolysis in 50 mM sodium acetate pH 5.0 at 50° C. Hydrolysis was carried out without stirring in the presence of 0.5 mg/ml bovine serum albumin (BSA). Reducing sugars were determined using p-hydroxybenzoic acid hydrazide (PHBAH) assay described in Example 18.

Activity of *Cladorrhinum foecundissimum* CEL7A endoglucanase on phosphoric acid-swollen cellulose (PASO) was determined by measuring the concentration of reducing sugars (RS) released during initial hydrolysis of PASO (2 mg/ml) in 50 mM sodium acetate pH 5.0 at 50° C. Hydrolysis was carried out without stirring in the presence of 0.5 mg/ml BSA. The enzymes were diluted so that RS concentration would increase linearly during initial 30 to 90 minutes of hydrolysis, and the degree of PASO conversion would not exceed 2% during this time. Reducing sugars were determined using p-hydroxybenzoic acid hydrazide (PHBAH) assay described in Example 18.

Activity of endoglucanases on chromogenic substrates, p-nitrophenyl-beta-D-cellobioside (PNPC) and p-nitrophenyl-beta-D-lactoside (PNPL), was determined using method of Deshpande et al. (Deshpande et al., 1984, *Anal. Biochem.* 138, 481-487) modified to a 96-well microplate format. p-Nitrophenol (PNP) was determined after 30-minute hydrolysis of PNPC (2.5 mM) or PNPL (2.5 mM) in 50 mM sodium acetate pH 5.0 at 40° C. by a spectrophotometric measurement at 405 nm. Prior to hydrolysis, the enzymes were diluted in 50 mM sodium acetate pH 5.0 to give less than 8% conversion of both substrates at the specified conditions.

TABLE 1

Relative activity of *Cladorrhimun foecundissimum* CEL7A cellulase at pH 5.0 and 50° C.

| Substrate | Relative Activity, % |
|---|---|
| Carboxymethylcellulose (CMC) | 100 |
| Phosphoric acid-swollen cellulose (PASC) | 14.5 |
| p-Nitrophenyl-beta-D-cellobioside (PNPC) | 0.58 |
| p-Nitrophenyl-beta-D-Lactoside (PNPL) | 0.77 |

Example 20

Thermal Stability of *Cladorrhinum foecundissimum* ATCC 62373 CEL7A Endoglucanase The thermal stability of the purified *Cladorrhinum foecundissimum* CEL7 endoglucanase was determined by incubating enzyme solutions at five temperatures (40° C., 50° C., 60° C., 70° C., and 80° C.), and measuring the residual activity on carboxymethylcellulose (CMC).

The enzyme was diluted in 50 mM sodium acetate pH 5.0, which contained 3.0 mg/ml BSA, and incubated for 3 hours in 1.1-ml ImmunoWare Microtubes arranged in an 8×12 microplate format (Pierce, Rockford, Ill.). BSA was added in order to prevent possible enzyme adsorption onto the plastic walls of microtubes. The protein concentration in the incubation mixtures was chosen so that less than 1% conversion of CMC would be obtained in subsequent assay for CMCase activity.

After a 3 hour incubation, 15 µl aliquots were removed using an 8-channel pipettor, and added to 75 µl of CMC solution (6 mg/ml in 50 mM sodium acetate pH 5.0) in a 96-well conical-bottomed microplate (Costar, clear polycarbonate, Corning Inc., Acton, Mass.). The residual CMCase activity was then measured as described in Example 19, and expressed as a percentage of the initial CMCase activity (Table 2).

After a 3 hour incubation, *Cladorrhinum foecundissimum* CEL7A endoglucanase retained over 90% of the initial CMCase activity at 40° C. and 50° C., about a third of the initial CMCase activity at 60° C., and 0% of the initial CMCase activity at 70° C. and 80° C.

TABLE 2

Residual CMCase activity of *Cladorrhinum foecundissimum* CEL7 endoglucanase after incubation for three hours at pH 5.0

| Temperature, ° C. | Residual CMCase activity, % of initial activity |
|---|---|
| 40° C. | 95.0 |
| 50° C. | 92.9 |
| 60° C. | 29.2 |
| 70° C. | 0.0 |
| 80° C. | 0.0 |

Example 21

Characterization of *Cladorrhinum foecundissimum* ATCC 62373 and *Thielavia terrestris* NRRL 8126 Endoglucanases on Various Polysaccharide Substrates

*Cladorrhinum foecundissimum* ATCC 62373 CEL7 and *Thielavia terrestris* NRR 8126 CEL7C endoglucanases were evaluated in the hydrolysis of various polysaccharides at pH 5.0 (50 mM sodium acetate buffer) and 50° C. The results were compared with those for recombinant *Trichoderma reesei* CEL7B (EGI) endoglucanase. Recombinant *Trichoderma reesei* CEL7B (EGI) endoglucanase can be prepared according to (include reference here).

The polysaccharides included preteated corn stover (PCS), phosphoric acid-swollen cellulose (PASC), carboxymethylcellulose (CMC), bacterial cellulose (BC), Avicel, xylan, xyloglucan, arabinoxylan, mannan and galactomannan. All substrates were used at 5 mg/ml, with the exception of bacterial cellulose, which was used at 0.9 mg/ml.

Reactions with an initial volume of 1 ml were carried out for 24 hours with intermittent stirring in Eppendorf® 96 DeepWell Plates (1.2 ml, VWR Scientific, West Chester, Pa., USA) capped with Eppendorf® 96 DeepWell Mats (VWR Scientific, West Chester, Pa., USA). Unless otherwise specified, the enzymes were loaded at 5 mg of protein per g of solids.

After 24 hours, 20 µl aliquots were removed from the hydrolysis reactions using an 8-channel pipettor, and added to 180 µl of 102 mM Na$_2$CO$_3$-58 mM NaHCO$_3$) in a Multi-Screen HV 96-well filtration plate (Millipore, Bedford, Mass., USA) to terminate the hydrolysis. The samples were vacuum-filtered into a flat-bottomed microplate. After appropriate dilution, the filtrates were analyzed for reducing sugars using the p-hydroxybenzoic acid hydrazide (PHBAH) assay as described in Example 18.

Table 3 shows relative conversion of various polysaccharides by the endoglucanases after 24-hour incubation. The relative conversion was calculated as a percentage of conversion obtained after 24-hour hydrolysis of phosphoric acid-swollen cellulose (PASO) by *Thielavia terrestris* CEL7C endoglucanase. The results in Table 3 show that all three endoglucanases had relatively high activity on xylan, xyloglucan and arabinoxylan, but low activity on mannan and galactomannan. The endoglucanases showed better hydrolysis of PASO (insoluble unsubstituted amorphous cellulose) than CMC (soluble substituted cellulose derivative). The endoglucanases had low activity on insoluble substrates with a high degree of crystallinity: bacterial cellulose, Avicel and PCS.

TABLE 3

Relative conversion of various polysaccharide substrates (5 mg/ml) by endoglucanases (5 mg protein per g solids); pH 5.0, 50° C., 24 hours

| Substrate | *Cladorrhinum foecundissimum* CEL7A | *Thielavia terrestris* CEL7C | *Trichoderma reesei* CEL7B |
|---|---|---|---|
| Pretreated corn stover (PCS) | 5.2 | ND | 8.7 |
| Phosphoric acid-swollen cellulose (PASC) | 21.1** | 100.0 | 32.4 |
| Carboxymethylcellulose (CMC) | 13.2** | 22.5 | 11.6 |
| Bacterial cellulose (BC)* | 1.3 | 8.1*** | 3.9 |
| Avicel (microcrystalline cellulose) | 1.4 | 6.4 | 4.2 |
| Birchwood xylan | 14.2 | 35.8 | 42.8 |
| Tamarind xyloglucan | 40.0 | 67.5 | 73.0 |
| Wheat arabinoxylan | 47.5 | 42.5 | 68.2 |
| 1,4-beta-D-Mannan | 0.5 | 1.4 | 1.8 |
| Carob galactomannan | 0.9 | 1.4 | 2.6 |

*Initial concentration of bacterial cellulose was 0.9 mg/ml
**Cladorrhinum foecundissimum* CEL7A was used at 0.25 mg protein per g solids for hydrolysis of PASC and CMC
***Thielavia terrestris* CEL7C was used at 25 mg protein per g solids for hydrolysis of bacterial cellulose Example 22

Hydrolysis of Various Polysaccharides by *Thielavia terrestris* NRRL 8126 CEL7C at 50° C.

Figure 14:
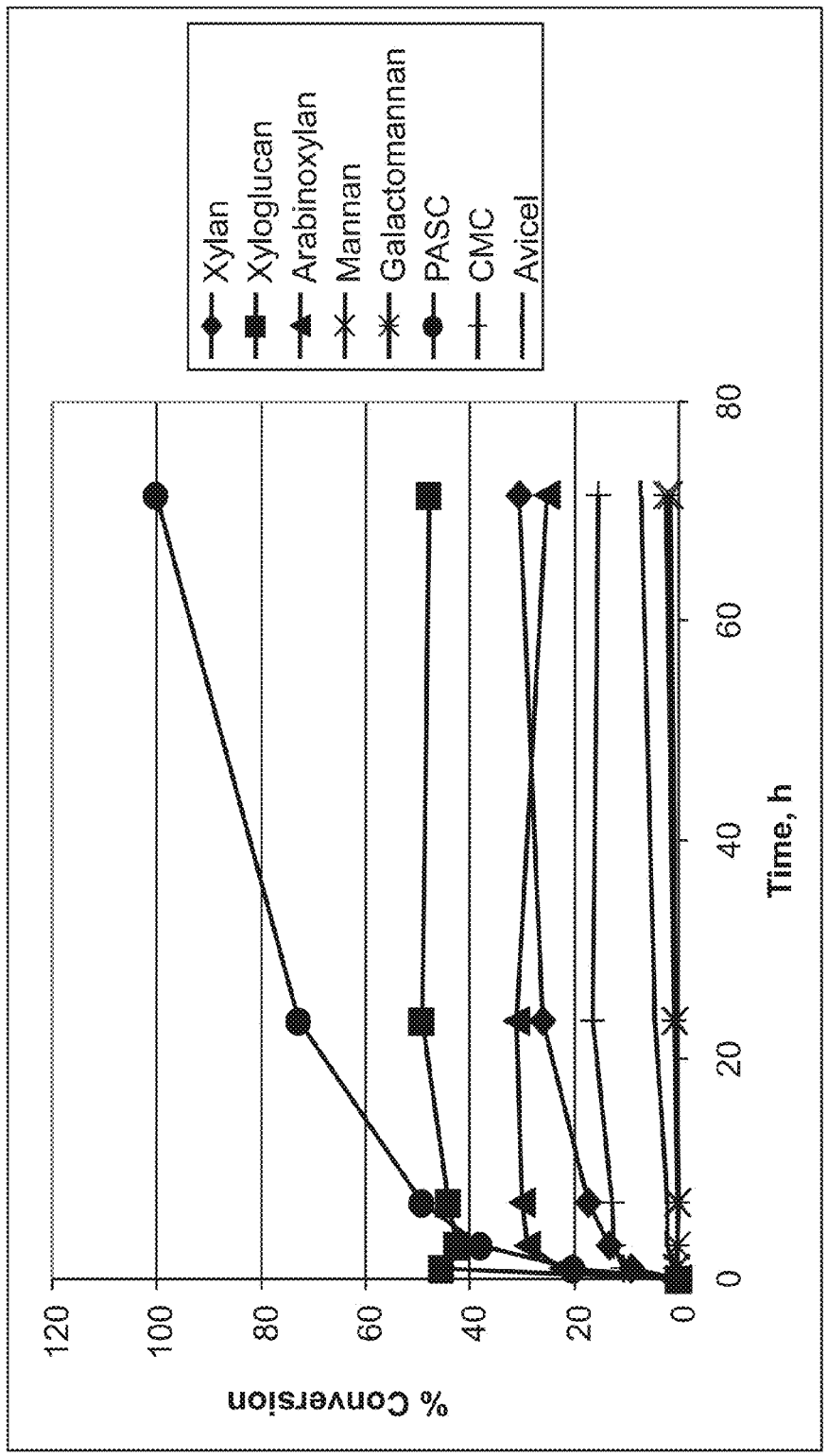
FIG. 14 shows the time course of hydrolysis of various substrates (5 mg/ml) by *T. terrestris* CEL7C endoglucanase (5 mg protein per g solids) at pH 5.0 and 50° C.

Example 21 was repeated except that hydrolysis was run for 71 hours and aliquots from reactions were taken at different time points to follow the time course of hydrolysis. *Thielavia terrestris* NRRL 8126 CEL7C endoglucanase was tested with eight polysaccharides. The relative degree of conversion of the polysaccharides as a function of hydrolysis time is shown in FIG. 14. The relative conversion is shown as a percentage of conversion obtained after 71-hour hydrolysis of phosphoric acid-swollen cellulose (PASO). Substrate concentration in all reactions was 5 mg/ml, and enzyme loading was 5 mg protein per g of solids.

*Thielavia terrestris* CEL7C endoglucanase showed high activity on PASO, xylan, xyloglucan and arabinoxylan, but low activity on mannan and galactomannan. *Thielavia terrestris* CEL7C endoglucanase had much lower activity on soluble substituted cellulose (CMC) than on insoluble unsubstituted cellulose (PASO). Activity on microcrystalline cellulose (Avicel) was significantly lower than activity on amorphous cellulose (PASO).

Example 23

Hydrolysis of Soluble Beta-Glucan from Barley by the *Cladorrhinum foecundissimum* ATCC 62373 *Thielavia terrestris* NRRL 8126 Endoglucanases The activity of the *Cladorrhinum foecundissimum* ATCC 62373 CEL7A and *Thielavia terrestris* NRRL 8126 CEL7C and CEL7E endoglucanases on soluble beta-glucan from barley (medium viscosity, 230 kDa, Megazyme International Ireland Ltd., Bray, Ireland) was determined at pH 5.5 (50 mM sodium acetate with 0.02% sodium azide) and 60° C. The results were compared with those for *Trichoderma reesei* CEL7B (EGI) endoglucanase. Recombinant *Trichoderma reesei* CEL7B (EGI) endoglucanase can be prepared as described in Example 21.

The initial concentration of beta-glucan in the hydrolysis reactions was 1.0% (w/v). One ml reactions were run without stirring in Eppendorf® 96 DeepWell Plates (1.2 ml, VWR Scientific, West Chester, Pa.). The enzymes were used at three protein loadings, 0.05, 0.1, and 0.2 mg per g of glucan. In control reactions, the endoglucanases were substituted with 50 mM sodium acetate pH 5.5 containing 0.02% sodium azide (buffer control) or with concentrated and buffer exchanged *Aspergillus oryzae* Jal250 broth containing no recombinantly expressed enzymes (*Aspergillus oryzae* Jal250 control).

Figure 15:
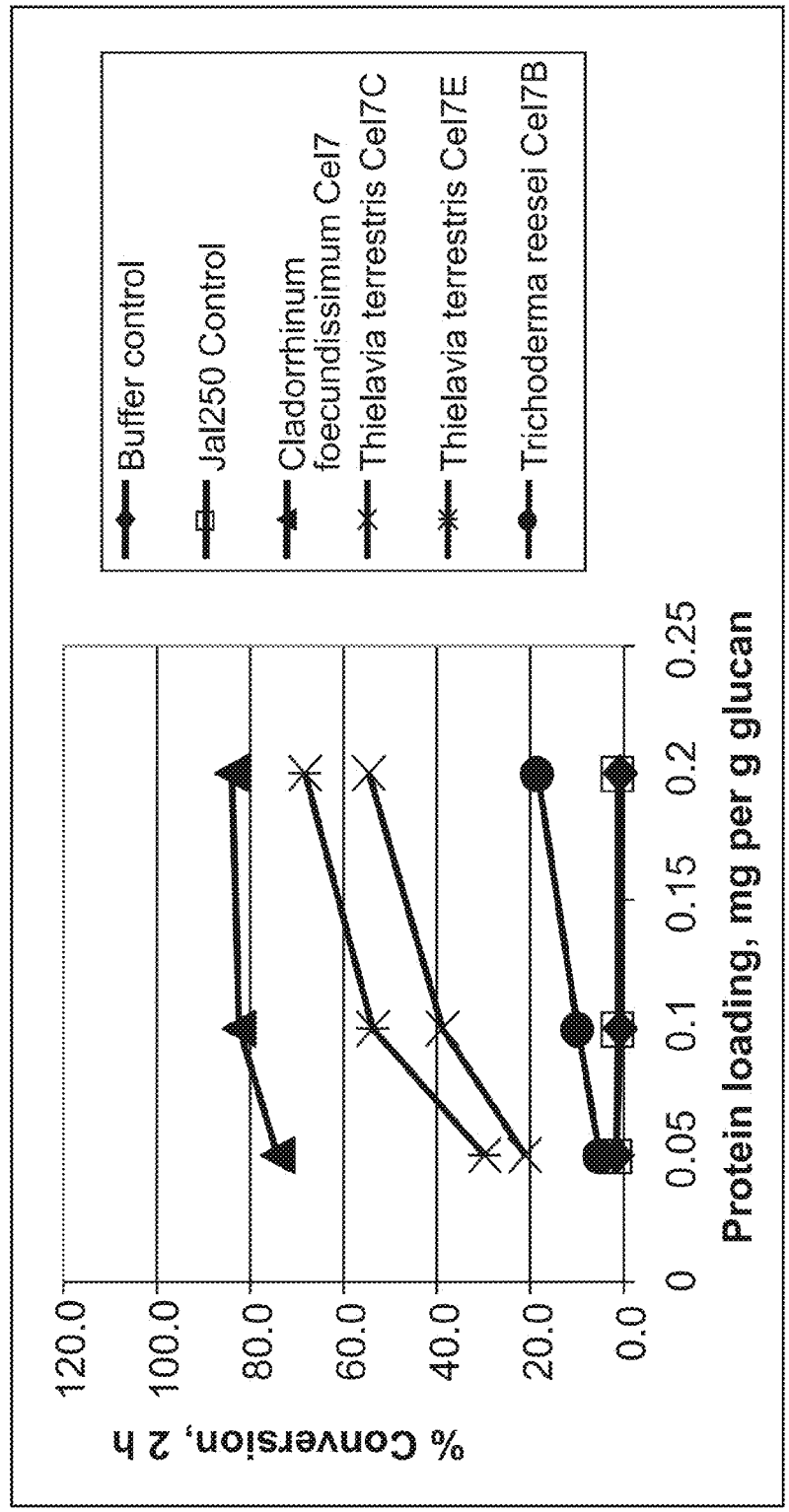
FIG. 15 shows the relative conversion of beta-glucan (1% w/v) after 2 hours of hydrolysis at pH 5.5 and 60° C.
Figure 16:
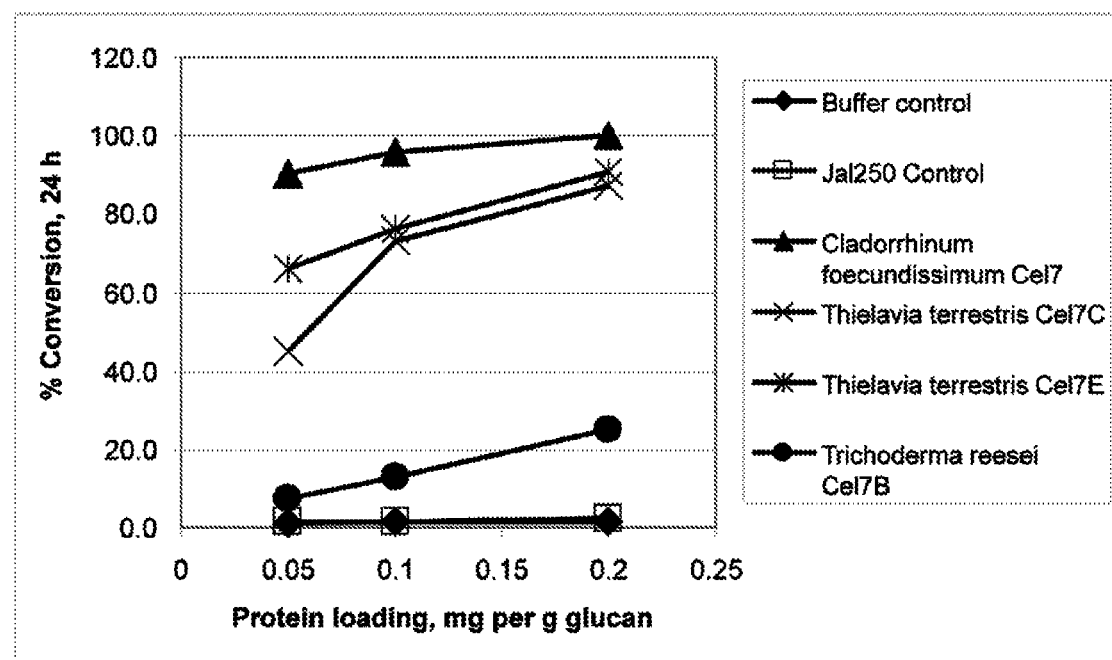
FIG. 16 shows the relative conversion of beta-glucan (1% w/v) after 24 hours of hydrolysis at pH 5.5 and 60° C.

Aliquots were removed from the hydrolysis reactions at 2 hours and 24 hours, diluted with deionized water, and analyzed for reducing sugars using the p-hydroxybenzoic acid hydrazide (PHBAH) assay as described in Example 18. The relative conversion of beta-glucan as a function of protein loading at two incubation times, 2 hours and 24 hours, is shown in FIGS. 15 and 16, respectively. The relative conversion is shown as a percentage of conversion obtained after 24-hour hydrolysis of beta-glucan by *Cladorrhinum foecundissimum* CEL7A endoglucanase (0.2 mg protein per g of glucan).

The *Trichoderma reesei* CEL7B endoglucanase showed lower conversion of beta-glucan than other endoglucanases, and produced almost no additional increase in reducing sugar concentration after 2 hours of hydrolysis. In contrast, the *Cladorrhinum foecundissimum* CEL7A, *Thielavia terrestris* CEL7C, and *Thielavia terrestris* CEL7E endoglucanases continued to produce new reducing end-groups beyond the 2 hour incubation time. The *Cladorrhinum foecundissimum* CEL7A endoglucanase showed better performance in hydrolyzing beta-glucan than the *Thielavia terrestris* CEL7C and *Thielavia terrestris* CEL7E endoglucanases.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* PaHa50 | NRRL B-30899 | Feb. 23, 2006 |
| *E. coli* PaHa38 | NRRL B-30896 | Feb. 23, 2006 |
| *E. coli* PaHa46 | NRRL B-30897 | Feb. 23, 2006 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having endoglucanase activity, selected from the group consisting of:
   (a) a polypeptide comprising an amino acid sequence having at least 95% sequence identity with the mature polypeptide of SEQ ID NO: 6;
   (b) a polypeptide which is encoded by a polynucleotide which hybridizes under at least high stringency conditions with (i) the mature polypeptide coding sequence of SEQ ID NO: 5, (ii) the cDNA sequence contained in the mature polypeptide coding sequence of SEQ ID NO: 5, or (iii) a complementary strand of (i) or (ii); and
   (c) a polypeptide which is encoded by a polynucleotide comprising a nucleotide sequence having at least 95% sequence identity with the mature polypeptide coding sequence of SEQ ID NO: 5.

2. The polypeptide of claim 1, which comprises or consists of the amino acid sequence of SEQ ID NO: 6.

3. The polypeptide of claim 1, which comprises or consists of the mature polypeptide of SEQ ID NO: 6.

4. The polypeptide of claim 1, which is encoded by a polynucleotide comprising or consisting of SEQ ID NO: 5.

5. The polypeptide of claim 1, which is encoded by a polynucleotide comprising or consisting of the mature polypeptide coding sequence of SEQ ID NO: 5.

6. The polypeptide of claim 1, which is encoded by a polynucleotide contained in plasmid pPH46 which is contained in *E. coli* NRRL B-30897.

7. The polypeptide of claim 1, wherein the mature polypeptide is amino acids 19 to 440 of SEQ ID NO: 6.

8. The polypeptide of claim 1, wherein the mature polypeptide coding sequence is nucleotides 107 to 1372 of SEQ ID NO: 5.

9. An isolated polynucleotide comprising a nucleotide sequence which encodes the polypeptide of claim 1, operably linked to one or more heterologous control sequences that direct the production of the polypeptide in an expression host.

10. A nucleic acid construct comprising the polynucleotide of claim 9 operably linked to one or more control sequences that direct the production of the polypeptide in an expression host.

11. A recombinant host cell comprising the nucleic acid construct of claim 10.

12. A method for producing the polypeptide of claim 1, comprising: (a) cultivating an isolated cell, which in its wild-type form produces the polypeptide, under conditions conducive for production of the polypeptide; and (b) recovering the polypeptide.

13. A method for producing the polypeptide of claim 1, comprising: (a) cultivating a recombinant host cell comprising a nucleic acid construct comprising a nucleotide sequence encoding the polypeptide under conditions conducive for production of the polypeptide; and (b) recovering the polypeptide.

14. A method for producing the polypeptide of claim 1, comprising: (a) cultivating a transgenic plant or a plant cell comprising a polynucleotide encoding the polypeptide having endoglucanase activity under conditions conducive for production of the polypeptide; and (b) recovering the polypeptide.

15. A transgenic plant, plant part or plant cell, which has been transformed with a polynucleotide encoding the polypeptide of claim 1.

16. A method of degrading or converting a cellulosic material, comprising: treating the cellulosic material with a composition comprising an effective amount of a polypeptide having endoglucanase activity of claim 1.

17. The method of claim 16, wherein the composition further comprises an effective amount of an endo-1,4-beta-glucanase, exo-1,4-beta-D-glucanase, and/or beta-D-glucosidase.

18. The method of claim 16, further comprising recovering the degraded or converted cellulosic material.

19. A method of producing a substance, comprising: (a) saccharifying a cellulosic material with a composition comprising an effective amount of a polypeptide having endoglucanase activity of claim 1, (b) fermenting the saccharified cellulosic material of step (a) with one or more fermenting microorganisms; and (c) recovering the substance from the fermentation.

20. A composition comprising the polypeptide of claim 1.

21. The polypeptide of claim 1, comprising an amino acid sequence having at least 95% sequence identity to the mature polypeptide of SEQ ID NO: 6.

22. The polypeptide of claim 1, comprising an amino acid sequence having at least 97% sequence identity to the mature polypeptide of SEQ ID NO: 6.

23. The polypeptide of claim 1, comprising an amino acid sequence having at least 98% sequence identity to the mature polypeptide of SEQ ID NO: 6.

24. The polypeptide of claim 1, comprising an amino acid sequence having at least 99% sequence identity to the mature polypeptide of SEQ ID NO: 6.

25. The polypeptide of claim 1, comprising an amino acid sequence having amino acids 19 to 440 of SEQ ID NO: 6.

26. The polypeptide of claim 1, which is encoded by a polynucleotide that hybridizes under at least high stringency conditions with (i) the mature polypeptide coding sequence of SEQ ID NO: 5, (ii) the cDNA sequence contained in the mature polypeptide coding sequence of SEQ ID NO: 5, or (iii) a complementary strand of (i) or (ii).

27. The polypeptide of claim 1, which is encoded by a polynucleotide that hybridizes under at least very high stringency conditions with (i) the mature polypeptide coding sequence of SEQ ID NO: 5, (ii) the cDNA sequence contained in the mature polypeptide coding sequence of SEQ ID NO: 5, or (iii) a complementary strand of (i) or (ii).

28. The polypeptide of claim 1, which is encoded by a polynucleotide that hybridizes under at least very high stringency conditions with the complementary strand of nucleotides 107 to 1372 of SEQ ID NO: 5.

29. The polypeptide of claim 1, which is encoded by a polynucleotide comprising a nucleotide sequence having at least 95% sequence identity to the mature polypeptide coding sequence of SEQ ID NO: 5.

30. The polypeptide of claim 1, which is encoded by a polynucleotide comprising a nucleotide sequence having at least 97% sequence identity to the mature polypeptide coding sequence of SEQ ID NO: 5.

31. The polypeptide of claim 1, which is encoded by a polynucleotide comprising a nucleotide sequence having nucleotides 107 to 1372 of SEQ ID NO: 5.

* * * * *